United States Patent [19]

Lo et al.

[11] Patent Number: 5,273,993

[45] Date of Patent: * Dec. 28, 1993

[54] COMPOUNDS HAVING ONE OR MORE AMINOSULFONYLOXY RADICALS USEFUL AS PHARMACEUTICALS

[75] Inventors: Young S. Lo, Hockessin, Del.; Joseph C. Nolan, Midlothian; William J. Welstead, Jr., Richmond, both of Va.; David A. Walsh, Augusta, Ga.; Dwight A. Shamblee; Ibrahim M. Uwaydah, both of Richmond, Va.

[73] Assignee: A. H. Robins Company, Incorporated, Richmond, Va.

[*] Notice: The portion of the term of this patent subsequent to Mar. 9, 2010 has been disclaimed.

[21] Appl. No.: 965,140

[22] Filed: Nov. 19, 1992

Related U.S. Application Data

[60] Division of Ser. No. 734,846, Jul. 24, 1991, Pat. No. 5,194,446, which is a continuation-in-part of Ser. No. 365,212, Jun. 12, 1989, abandoned.

[51] Int. Cl.$^5$ ............... A61K 31/415; C07D 233/54
[52] U.S. Cl. ........................... 514/400; 514/309; 514/311; 514/312; 514/347; 514/348; 514/415; 514/418; 514/362; 514/369; 514/398; 514/445; 514/457; 514/473; 548/335.5; 558/48
[58] Field of Search ............... 548/335.5; 558/48; 514/309, 311, 312, 347, 348, 415, 418, 362, 369, 398, 445, 457, 473, 397, 394, 400

[56] References Cited

U.S. PATENT DOCUMENTS

| | | | |
|---|---|---|---|
| 2,839,562 | 6/1958 | Wegler et al. | 260/456 |
| 3,082,238 | 3/1963 | Dunbar | 260/456 |
| 3,661,830 | 5/1972 | Hill | 260/30.8 |
| 3,950,380 | 4/1976 | Feit et al. | 548/335.5 X |
| 3,997,585 | 12/1976 | Hirsch | 260/456 A |
| 4,061,663 | 12/1977 | Hirsch | 260/456 |
| 4,075,351 | 2/1978 | Hirsch | 424/303 |
| 4,222,767 | 9/1980 | Gates et al. | 71/103 |
| 4,513,006 | 4/1985 | Maryanoff et al. | 514/23 |
| 4,582,916 | 4/1986 | Maryanoff et al. | 549/387 |
| 4,591,601 | 5/1986 | Maryanoff et al. | 514/462 |
| 4,792,569 | 12/1988 | Maryanoff et al. | 514/517 |
| 4,824,475 | 4/1989 | Markley et al. | 71/103 |
| 5,025,031 | 6/1991 | Lo et al. | 558/48 X |
| 5,192,785 | 3/1993 | Lo et al. | 558/48 X |

FOREIGN PATENT DOCUMENTS

| | | | |
|---|---|---|---|
| 2417764 | 10/1975 | Fed. Rep. of Germany | 558/48 |
| 2531445 | 2/1976 | Fed. Rep. of Germany | 534/856 |
| 2559210 | 7/1976 | Fed. Rep. of Germany | 558/48 |
| 1554976 | 1/1968 | France | 558/48 |

OTHER PUBLICATIONS

Spillane and Burke, Synthesis (12), 1021-1024 (1986).
Spillane et al., J. Chem. Soc. Perk. Trans. I (3), 677-679 (1982).

(List continued on next page.)

*Primary Examiner*—Floyd D. Higel
*Attorney, Agent, or Firm*—R. F. Boswell, Jr.

[57] ABSTRACT

Methods of treating chronic arthritis and osteoporosis which utilize both known and novel compounds which would fall under the general formula:

$$(HO)_p-A-[-OS(O)_2NR^1R^2]_z$$

wherein A encompasses a wide range of values including but not limited to aryl, loweralkyl, cycloalkyl, and carbohydrates including sucrose and fructose; p is equal to the number of unreacted hydroxy groups contained on the molecule and may be zero; z is the number of $-OS(O)_2NR^1R^2$ groups and is always at least one; $R^1$ and $R^2$ are selected from hydrogen, loweralkyl, carboxy and the like; a novel process for preparing the compounds is provided wherein an appropriate sulfamic acid aryl ester is reacted with a hydroxy substituted A radical which may or may not contain thereon protected carboxyl, amino or hydroxy substituents, in an aprotic solvent containing a tertiary amine base. Pharmaceutical compositions for the treatment of chronic arthritis and osteoporosis are also provided.

9 Claims, No Drawings

OTHER PUBLICATIONS

Lohaus, Chem. Ber. 105, 2791–2799 (1972).
Hedayatullah and Guy, Synthesis, 357 (1978) (5).
Weiss and Schulze, Liebigs Ann. Chem. 729, 40–51 (1969).
Maryanoff et al., J. Med. Chem. 30, 880–887 (1987).
Usov, Isv. Akad. Nauk. SSSR, Ser. Khim. 1975, (s), 1084–8 (CA 83:131847t).
Dubois, J. Org. Chem. 45, 5373–75 (1980).
Hedayatallah and Hugeny, Phosphorus and Sulfur, 20, 371–375 (1984).
Walsh, et al., J. Med. Chem. 1990; 33, 2068–2070.

COMPOUNDS HAVING ONE OR MORE AMINOSULFONYLOXY RADICALS USEFUL AS PHARMACEUTICALS

This application is a division of Ser. No. 07/734,846, filed Jul. 24, 1991, now U.S. Pat. No. 5,194,446 (Mar. 16, 1993) which was a continuation-in-part of Ser. No. 07/365,212 filed Jun. 12, 1989, abandoned.

BACKGROUND OF THE INVENTION

1. Field of Invention

The present invention is principally concerned with the use of sulfamic acid derivatives in the treatment of mammals in several therapeutic areas. More particularly the invention is concerned with the pharmaceutical use of compounds and pharmaceutical compositions therefor which compounds carry one or more aminosulfonyloxy radicals or substituted aminosulfonyloxy radicals, especially sulfamate esters prepared from compounds having one or more hydroxyl groups, most notably in the treatment of chronic arthritis and osteoporosis. Certain of the compounds are novel and a certain process for preparing the compounds is also novel.

2. Information Disclosure Statement

Numerous references disclose sulfamate esters derived from a phenol or naphthol. Wegler, U.S. Pat. No. 2,839,562, discloses insecticide sulfamate esters of the formula $ArOSO_2NRR^1$ where Ar is naphthyl, phenyl or phenyl substituted by chlorine, methyl or nitro, and R and $R^1$ are selected from alkyl, cycloalkyl, aryl or form a heterocyclic group with the interposed nitrogen. Dunbar, U.S. Pat. No. 3,082,238, discloses sulfamate esters of the formula $Ar(OSO_2NR_2)_{1-2}$ where Ar is naphthyl, phenyl or phenyl substituted by chlorine, methyl, ethyl, nitro, diloweralkylamino, diloweralkylaminoalkyl, or phenyl and R is loweralkyl useful as a herbicide or fungicide. The French Patent 1,555,976 discloses a phenylsulfate ester of the formula:

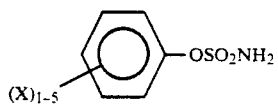

where X is H, OH, methyl, chlorine, bromine, methoxy, methanesulfonyl, methoxycarbonyl or phenyl.

Other references disclosing sulfamate esters derived from phenol, substituted phenol, or other hydroxyaryl compounds are Hedayatullah and Guy, Synthesis (1978), p. 357; G. Lohause, Chem. Ber. 105, 2791-99 (1972); Dubois, J. Org. Chem. 45, 5373-75 (1980) and Spillane, J. Chem. Soc., Perkin. Trans. I, 3, 677-9 (1982). Maryanoff, in U.S. Pat. No. 4,513,006 discloses anticonvulsant sulfamate esters of cyclohexylmethanol, 1,2,3,4-tetrahydronaphthalene-2-methanol, or tetrahydropyranyl-2-methanol monosulfamate derivatives of the formula

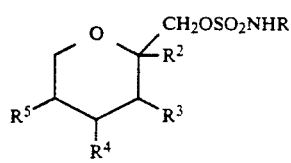

where $R^2$ and $R^3$ and/or $R^4$ and $R^5$ may form a substituted methylenedioxy group. These monosaccharide derivatives are also disclosed to be useful as carbonic anhydrase inhibitors. In U.S. Pat. No. 4,591,601 Maryanoff discloses the sulfamate ester of 2-substituted-4-(1,3-dioxolane) methanols useful as anticonvulsants. Other sulfamate esters of various furanose and pyranose monosaccharide derivatives, cycloalkylmethanol, bi (and tri) cycloalkylmethanol, 2-phenylethanol, 2,2-diphenylethanol, and 4,5-benzoisoxazol-3-methanol are disclosed in J. Med. Chem. 30, 880–887 (1987). Usov, Izv. Akad. Nauk. SSSR. Ser. Khim. 1975 (1084–8), CA 83:131847t, reports mass spectral studies of monosulfamate esters of acetylated monosaccharides. Shuman et al. in J. Amer. Chem. Soc. 91, 3391-2 (1969) describes a sulfamate ester of a fluorinated nucleoside.

N-benzylsulfamate esters of cyclohexanol and n-hexanol are described by Spillane and Burke, Synthesis, 1021–1024 (1986). The German Patent 2,559,210 discloses contraceptive utility for glycol sulfamate esters of the formula $R^2R^3NSO_2OCH_2(CRR^1)_nCH_2OSO_2NR^2R^3$ where $R^2$ and $R^3$ are H, alkyl, aryl or $R^2NR^3$ is pyrrolidine or piperidine; R and $R^1$ are H, alkyl, arylalkyl and n is 0-8. Erucyl sulfamate and oleyl sulfamate are disclosed as slip additives for polyethylene in U.S. Pat. No. 3,661,830. Weiss and Schulze, Liebigs Ann. Chem. 729, 40–51 (1969) disclose the synthesis of sulfamate esters of the formula $R^1OCH_2CH_2OSO_2NHR$ where $R^1$ is loweralkyl or unsubstituted phenyl and R is loweralkyl.

2-(Substitutedphenyl)ethanol esters of sulfamic acid useful in treating convulsions and glaucoma are disclosed by Maryanoff in U.S. Pat. No. 4,792,569.

Markley, U.S. Pat. No. 4,824,475 discloses herbicidal activity of sulfamate esters of the formula:

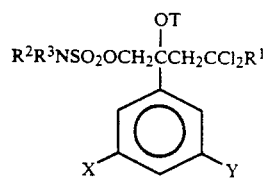

where $R^2$ and $R^3$ are phenyl, loweralkylphenyl, naphthyl, or benzyl and T is H, acetyl, propionyl, or trifluoroacetyl.

Gates and Baldwin, U.S. Pat. No. 4,222,767, disclose herbicidal sulfonates and sulfamates of the formula:

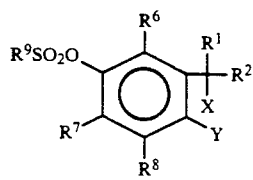

where $R^9$ can be a $C_1-C_4$ loweralkyl (or dialkyl)amino group, X is $-CHR^3OR^4$ and Y is $-OR^5$. Among the definitions for the $R^4$ and $R^5$ groups are $-SO_2R^{11}$ where $R^{11}$ can be $C_1-C_6$ alkyl (or dialkyl)amino. Thus this disclosure encompasses phenyl sulfamate esters and 1,3' (and 6') phenylalkyl sulfamate esters.

An intermediate for azo dye preparation disclosed in German Offen. 2,531,445 has the formula $PhNEtCH_2CH_2OSO_2NMe_2$. Compounds having the formula:

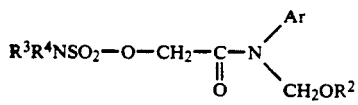

wherein $R^3$ and $R^4$ are hydrogen or loweralkyl and $R^2$ is loweralkyl are disclosed in German Offen. 2,417,764 (CA 84:30709q) as herbicides.

The prior art thus discloses sulfamate esters of phenol, substituted phenol, naphthol, monosaccharides, heterocyclic methanols, pbhenoxyethanol, loweralkoxyethanols, and phenylethanol. No disclosure has been found for alkyl groups substituted by 2-sulfamate groups and further substituted by aryloxy, arylcarbonyl aryloxycarbonyl, or heteroaryl group nor alkyl groups having more than 2 sulfamate ester groups.

Although some of the compounds of the methods of this invention fall within the disclosures of the above references, none of the above references disclose the uses of sulfamate esters in the treatment of chronic arthritis or treating or preventing osteoporosis. Certain compounds of this invention resemble those disclosed in the above references but are not encompassed by the formulas disclosed above and are believed to be novel.

SUMMARY OF THE INVENTION

Compounds of Formula I are useful in the pharmaceutical methods of this invention $(HO)_p$—A—$[-OS(O)_2NR^1R^2]_z$   Formula I wherein A is substituted on one or more carbon atoms by an aminosulfonyloxy radical, i.e., a radical having the formula $-OS(O)_2NR^1R^2$, said A being selected from the group consisting of:
aryl,
alkyl,
cycloalkyl,
aryl-alkyl,
arylalkanoic acid,
haloalkyl,
cycloalkyl-alkyl,
aryloxy-alkyl,
loweralkoxy-alkyl,
(aryl)(loweralkyl)aminoalkyl,
aryl-thio alkyl,
aryl-sulfinyl-alkyl,
aryl-sulfonyl-alkyl,
arylaminocarbonylalkyl,
alkylaminocarbonylalkyl,
aryloxycarbonylalkyl,
loweralkoxycarbonylalkyl,
2-pyrrolidinone-1-alkyl,
alkylcarbonylalkyl,
arylcarbonylalkyl,
arylcarboxyalkyl
arylhalogen substituted alkyl
arylalkyloxyalkyl

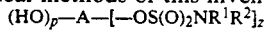

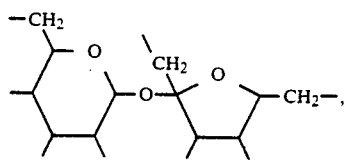

or a (carbohydrate skeleton) $(-)_n$ wherein $(-)_n$ wherein $(-)_n$ represents 1-8 available linkages including skeletons of sucrose, i.e.

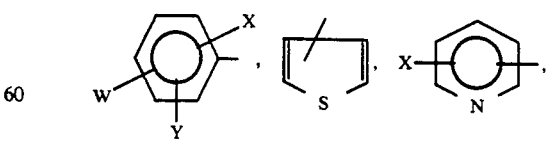

glucose and fructose, and where an alkyl moiety is present in the above definition of A, the alkyl group must be substituted by at least one aminosulfonyloxy group;

Aryl or aryl moieties are selected from:

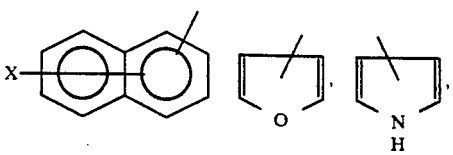

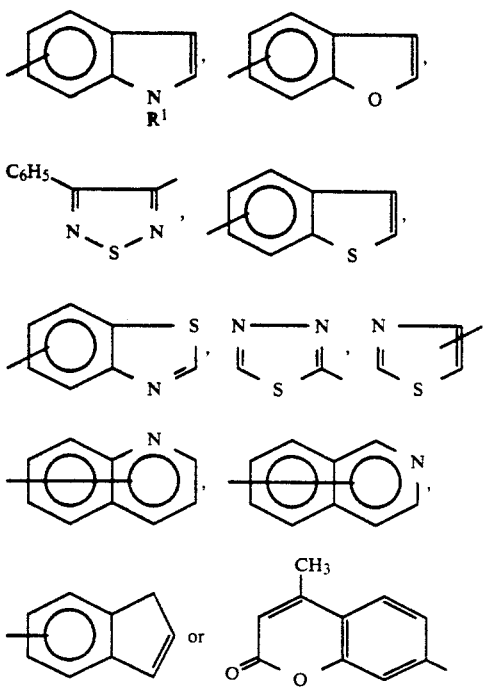

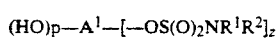

X is selected from hydrogen, halo, CF$_3$, nitro, —SO$_2$NR$^1$R$^2$, —OSO$_2$NR$^1$R$^2$, loweralkoxy, —OCH$_2$CH$_2$OSO$_2$NR$^1$R$^2$, hydroxy, amino, methylcarbonylamino, loweralkyl, methyloxycarbonyl, 1H-imidazol-1-yl, 3-thiazole, 1-pyrrole, phenyl, 1H-triazol-1-yl, loweralkylamino, cyano, 2-(or 4-)loweralkyl-1H-imidazol-1-yl, 4-phenyl-1H-imidazol-1-yl, benzyloxy, diloweralkylamino, —COOH, —COOM wherein M is a pharmaceutically acceptable metal cation, aryloxy or aroyl;

Y is selected from: hydrogen, halo, loweralkoxy, hydroxy or loweralkyl;

W is selected from hydrogen, loweralkoxy or loweralkyl;

p=number of unreacted hydroxyl groups, including zero;

z=number of —OS(O)$_2$NR$^1$R$^2$ groups and is always at least one;

m=0-4;

n=p+z=1-8;

q=1-10

R$^1$=H, loweralkyl;

R$^2$=H, loweralkyl, —CO$_2$R$^1$, or —CO$_2$M+ wherein M is defined above,

R$^3$, R$^4$=H, lower alkyl or R$^3$ and R$^4$ form a heteroalicyclic ring with the interposed nitrogen, and the pharmaceutically acceptable salts thereof, when they can be formed and the optical isomers thereof, when they can be formed;

The compounds of Formula I which are novel are represented by Formula Ia (HO)p—A$^1$—[—OS(O)$_2$NR$^1$R$^2$]$_z$    Formula Ia wherein A$^1$ is substituted on one or more carbon atoms by an aminosulfonyloxy radical as under formula I, said A$^1$ being selected from the group consisting of:

aryloxyalkyl, with a proviso that when aryl is be unsubstituted phenyl, the alkyl moiety is substituted by more than one sulfamoyloxy group, arylalkyl with a proviso that when aryl is

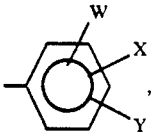

the alkyl moiety is substituted by more than one aminosufonyloxy radical;

alkyl, wherein at least one of the aminosulfonyloxy radicals is on a tertiary carbon atom, aryloxycarbonylalkyl, loweralkoxycarbonylalkyl, alkylcarbonylalkyl, arylcarbonylalkyl, arylalkanoic acid, 4-phenyl-thiadiazole-3-yl, 2-(3-phenoxyphenyl)-4-thiazolidinone-3-ylalkyl 2-pyrrolidone-1-alkyl;

and where an alkyl moiety is present in the above definition of A$^1$, the alkyl group must be substituted by at least one aminosulfonyloxy radical and as further defined above;

and wherein the aryl moieties of aryloxyalkyl, aryloxycarbonyl alkyl, arylcarbonylalkyl are as defined for aryl under Formula I hereinabove and W, X, Y, R$^1$, R$^2$, p and z are as defined under Formula I hereinabove.

In the further definitions of symbols in the formula hereof and terms where they apply elsewhere throughout the specification and the claims, the terms have the following significance.

The term "alkyl" as used herein unless otherwise specified includes straight and branched chain radicals of up to 12 carbons inclusive and is exemplified by such groups as methyl, ethyl, propyl, isopropyl, butyl, sec. butyl, tert. butyl, amyl, isoamyl, hexyl, heptyl, octyl, nonyl, decyl, lauryl and the like and is intended to include methylene chains and branched methylene chains when appropriate under the definitions in the formulas. Loweralkyl radicals have 1-8 carbon atoms. The term loweralkoxy as used herein refers to a —O—loweralkyl group wherein loweralkyl is defined above.

The term "tertiary carbon atom" as used herein refers to a carbon atom attached directly to three other carbon atoms.

The term "cycloalkyl" as used herein includes cyclic alkyl radicals containing 3-9 carbon atoms inclusive and includes such groups as cyclopropyl, cyclobutyl, cyclopentyl, cyclohexyl, methylcyclohexyl, cycloheptyl and the like.

The terms "halo" or "halogen" when referred to herein include, fluorine, chlorine, bromine and iodine unless otherwise stated.

Pharmaceutically acceptable salts of the compounds of the present invention generally form when A is an aryl group having a heterocyclic nitrogen radical or A contains a basic nitrogen component and include salts of either strong or weak acids. Representative of strong acids are hydrochloric, sulfuric and phosphoric acids. Representative of weak acids are fumaric, maleic, succinic, oxalic, citric, tartaric, hexamic and the like.

By "sucrose core or skeleton" in the definition of A is meant:

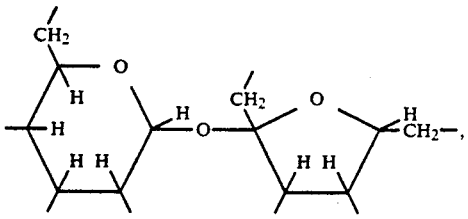

A "fructose or other carbohydrate core or skeleton" will readily be perceived by one skilled in the art in reference to the above definition of sucrose core or other carbohydrate skeleton. In utilization of these cores or skeletons for the invention, available or open bonds indicated by dashes of the cores or skeleton are attached to or substituted by at least one aminosulfonyloxy group and may be completely substituted by aminosulfonyloxy groups. In the instance of incomplete substitution the bonds are attached to the original hydroxy groups of the carbohydrate.

Elaborating further on the use of the term "wherein A (or $A^1$) is substituted on one or more carbon atoms by an aminosulfonyloxy radical", the aminosulfonyloxy radical represented by $-OS(O)_2NR^1R^2$ may be located singly or multiply on aryl (or other cyclic) or alkyl moieties at any site on one or more carbon atoms capable of being hydroxylated and for example in the instance of phenyl moiety up to 5 such aminosulfonyloxy radicals may be present, thereby wholly or partially superseding the values given in the definition for X, Y and W. In the instance wherein A or $A^1$ contain moieties of such as both aryl (or other cyclics) and alkyl, at least one aminosulfonyloxy radical is present on the alkyl moiety.

The term "chronic arthritis" as used herein is meant to include chronic inflammatory arthritic conditions appearing either singularly or in combination. Exemplary of the group but not meant to be limiting are the following arthritic conditions: osteoarthritis, rheumatoid arthritis, acromegalic arthritis, bacterial arthritis, gonococcal arthritis, chronic inflammatory arthritis, exudative arthritis, palindromic arthritis, and viral arthritis.

The term "osteoporosis" as used herein refers to conditions in which deossification, or rarefraction of bone occurs. The condition is marked by an absolute decrease in bone tissue, resulting in enlargement of marrow and havian spaces, decreased thickness of cortex trabeculea, and structural weakness. Exemplary of the group of osteoporotic conditions but not meant to be limiting are the following: neurogenic osteoporosis, osteoporosis circumscripta cranii, senile osteoporosis, osteoporosis of disuse, postmenopausal osteoporosis, and post-traumatic osteoporosis.

The term "aprotic solvent" as used herein refers to polar solvents of moderately high dielectric constants, which do not contain acidic hydrogen such as dimethylsulfoxide, N,N'-dimethyformamide, p-dioxane and the like.

The term "tertiary amine base" as used herein refers to pyridine, trimethyamine, triethylamine, tri-n-propylamine and the like.

By the term "optical isomers" as used herein is meant isomers of compounds of Formula I or Ia which may exist when chiral centers are present in the compounds of Formula I or Ia. These chiral centers when present must be on the "A" moiety of the Formula I compound or the "$A^1$" moiety of the Formula Ia compound. It should be noted that whenever any chiral centers exist in the compounds of Formula I or Ia there is potential for the separation of optical isomers, otherwise known as enantiomers. Exemplary of the methods utilized for the separation of optical isomers of compounds of Formula I or Formula Ia, is the use of column chromatography wherein the column has an appropriate chiral stationary phase. An additional method which may be employed is the use of optically active acids or bases to resolve the enantiomers in successive recrystallizations of the diastereomeric salts. It is also noted that compounds of Formula I and Ia which have chiral centers may be prepared by chiral synthesis methods, if so desired, when the same are applicable to the preparation of a particular optical isomer of a Formula I or Formula Ia compound.

Compounds of Formula I are prepared by Methods I, II and III following:

Method I

The process of Method I is represented by the following general equation:

$A^2(OH)_n$ + n moles +

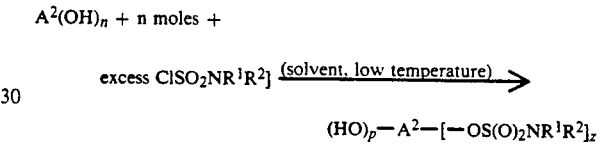

$(HO)_p-A^2-[-OS(O)_2NR^1R^2]_z$ wherein values for $A^2$ include those in the definition for A of Formula I with the proviso that $A^2$ may additionally carry protected carboxy, protected amino or protected hydroxy, groups and a further proviso alternative is that aryl may be a group outside the definition of A carrying non-interfering radicals. Compounds prepared under the latter proviso wherein $A^2$ is aryl are useful as reagents in Method II.

$R^1$ = hydrogen or loweralkyl,
$R^2$ = hydrogen, loweralkyl or $-C(O)OR^3$,
$R^3$ = loweralkyl, or phenylloweralkyl,
n = p+z
p = number of unreacted hydroxyl groups including zero,
z = number of sulfamate esterified hydroxy groups.

Protected carboxy groups are represented by benzyloxycarbonyl and trichlorethyloxycarbonyl, Protected amino groups are represented by benzyloxycarbonylamino and trichloroethyloxy carbonyl amino, Protected hydroxy groups are represented by benzyloxycarbonyloxy or trichloroethyloxycarbonyloxy.

Protected carboxy groups, protected amino groups or protected hydroxy groups are deprotected by hydrogenolysis in the instance of benzyloxy carbonyl radicals and deprotected by treating with zinc/acetic acid in the instance of trichloroethyloxycarbonyl radicals.

Generally in Method I, the reaction is carried out in a non-reactive aprotic organic solvent suitably methylene chloride or acetonitrile at temperatures over a range of 0°-100° C. In some instances a non-interfering tertiary organic base such as triethylamine, pyridine or diisopropylethylamine is beneficially added to absorb the hydrochloric acid which is liberated. Products are isolated by various conventional means as illustrated in the examples.

Method I in conjunction with known protection group chemistry can be used to prepare certain types of Formula I compounds as illustrated in Chart I and Example 50.

Protected hydroxy groups are represented by benzyloxycarbonyloxy or trichloroethyloxycarbonyloxy.

Protected carboxy groups, protected amino groups or protected hydroxy groups are deprotected by hydro-

CHART I

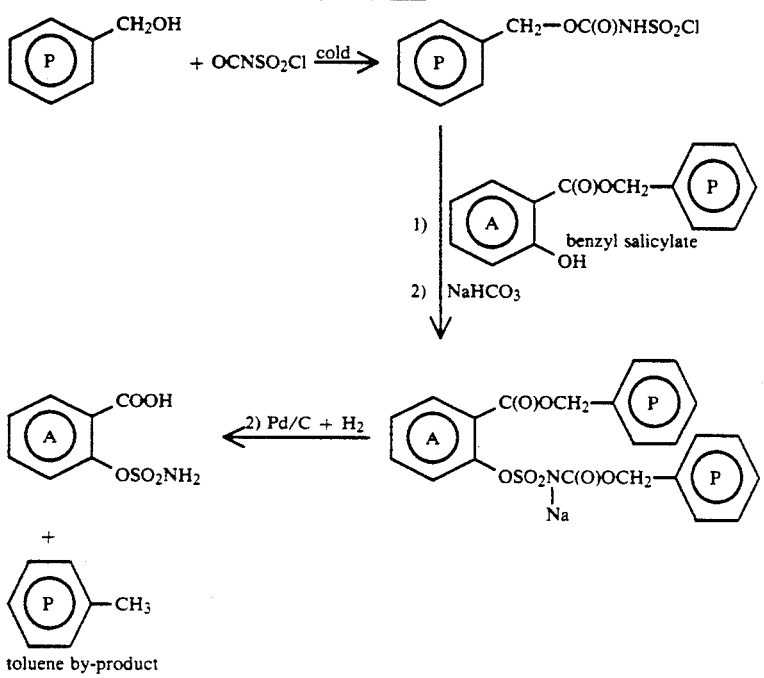

Footnotes Chart I:
P designates radicals involved with protection.
A represents product or core product intermediate.
Carboxy groups in other positions are contemplated. Other groups substitutable for

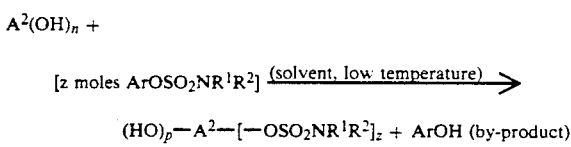

such as pyridinyl, naphthenyl, and biphenyl are also contemplated.

Method II—General

Method II is represented by the following equation:

$$A^2(OH)_n + [z \text{ moles } ArOSO_2NR^1R^2] \xrightarrow{\text{(solvent, low temperature)}} (HO)_p-A^2-[-OSO_2NR^1R^2]_z + ArOH \text{ (by-product)}$$

wherein Ar is an aryl group carrying non-interfering radicals and may be an aryl group outside the definition of A or $A^2$;

wherein values for $A^2$ include those in the definition for A of Formula I with the proviso that when $A^2$ is aryl protected carboxy, protected amino or protected hydroxy groups are substituted for carboxy, amino or hydroxy, said protected hydroxy being excluded from $(OH)_n$, i.e., when p=O, n=z.

$R^1$ = hydrogen or loweralkyl,
$R^2$ = hydrogen, loweralkyl or -C(O)OR$^3$,
$R^3$ = loweralkyl, or phenyloweralkyl,
n = p+z
p = number of unreacted hydroxyl groups including zero,
z = number of sulfamate esterified hydroxy groups.

Protected carboxy groups are represented by benzyloxycarbonyl and trichlorethyloxycarbonyl.

Protected amino groups are represented by benzyloxycarbonylamino and trichloroethyloxy carbonyl amino.

genolysis in the instance of benzyloxycarbonyl radicals and deprotected by treating with zinc/acetic acid in the instance of trichloroethyloxycarbonyl radicals.

Method II, hereinabove outlined, represents a novel process for synthesizing Formula I compounds and is described more fully as follows: In an organic solvent system consisting of a non-reactive aprotic solvent containing from about 1 to about 20% of a tertiary organic base, and preferably at least 5% of said tertiary organic base, there are reacted at a temperature of from about 50° to 200° C. and preferably at about 90° to 140° C., a reagent sulfamic acid aryl ester and a hydroxy substituted $A^2$ radical wherein $A^2$ is defined as A under Formula I above, except that $A^2$ may not be aryl substituted by unprotected carboxy or unprotected amino, and $A^2$ may additionally be substituted by a protected hydroxy, but wherein said protected hydroxy is excluded from $(OH)_n$ in the equations above. If $A^2$ is substituted by protected amino, protected carboxy or protected hydroxy, then the protected groups are deprotected subsequent to the transfer of the aminosulfonyloxy radical from the sulfamic acid aryl ester reactant, thus giving the desired formula I compound. In addition to forming the desired Formula I compound in the reaction there is also formed a hydroxy substituted aryl by-product in the reaction. After the desired Formula I compound is formed in the reaction it is extracted from the reaction mixture by partitioning between an organic and aqueous layer and recrystallization by methods commonly known in the art to give a Formula I compound as a free base. A pharmaceutically acceptable salt of the free base may be obtained by reacting with a pharmaceutically acceptable acid in conventional manner. As an example of the reaction, there is included herein Example 52, which may be considered to typify the reaction, but which it should be understood is not intended to limit the broadness of the disclosure of the parameters given herein for the reaction method, or to limit the number of Formula I compounds for which the method is applicable.

This novel method for preparing Formula I compounds, labeled as Method II reaction above, may also be referred to as the transfer reaction herein, in as much as the sulfamic acid ester group originally present on the sulfamic acid aryl ester reactant may be considered to be transferred to the hydroxy substituted $A^2$ radical, and the hydroxy substituent on the $A^2$ radical may be considered to be transferred to the aryl radical of the previous sulfamic acid ester group. The aryl group contained on the initial sulfamic acid aryl ester may be selected from aryl as defined under Formula I or from aryl other than that as defined under Formula I, to the extent that the selected aryl substituent is not to be substituted by a radical which would interfere with the transfer of the aminosulfonyloxy radical from the sulfamic acid aryl ester group to the hydroxy substituted $A^2$ reactant. It should be noted that if the aryl substituent of the sulfamic acid aryl ester is the same as the $A^2$ substituent of the hydroxy substituted $A^2$ reactant, then the net effect of the reaction would be zero since the products of the reaction would be equivalent to the reactants, therefore the aryl radical of the sulfamic acid aryl ester should never be identical to the $A^2$ radical of the hydroxy substituted $A^2$ reactant in this method. It should also be understood that this method may be compound if the Formula I compound utilized in the preparation of the second Formula I compound has an aryl A substituent with no interfering radicals substituted thereon, such as hydroxy, amino, carboxy and the like.

Method III—General

Certain compounds of Formula I and reagents for use in Method II may also be prepared by reaction represented by the following equation:

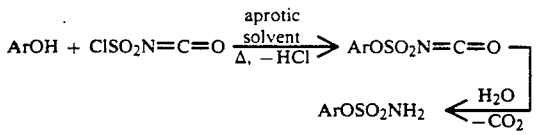

Generally in Method III, the reaction is carried out in a non-reactive aprotic solvent, suitably toluene, chlorobenzene or acetonitrile at temperatures over a range of 80°-150° C.

The preparation of chemical intermediates is illustrated in the following preparations. The examples following the preparations illustrate the synthesis methods for preparing compounds of Formula I. The scope of the present invention is not limited by the descriptive methods and procedures of the preparations and examples, however.

PREPARATION 1

3-(4-Chlorophenoxy)-1,2-propanediol.

A mixture of 25.7 g (0.2 mole) of 4-chlorophenol, 18.5 g (0.25 mole) of glycidol and 1 ml of pyridine was stirred and heated at 85°-90° C. overnight. The pot residue was partitioned between ethyl ether and water. The organic layer was washed with water and brine, dried over sodium sulfate, and concentrated to give a gum which crystallized when triturated with petroleum ether (boiling point range, 30°-60° C.). The solid was collected by filtration and recrystallized from isopropyl ether to yield 27.2 g (67%) of off-white solid, mp 73°-75° C. (lit[1] mp 77° C.).

[1] W. Bradley and J. Forrest, Brit 628,497 (1949); Chem Abstr 44, 3023eg (1950).

Analysis: Calculated for $C_9H_{11}ClO_3$: C, 53.35; H, 5.47; Found: C, 53.02; H, 5.56.

PREPARATION 2

3-Phenoxy-1-propanol.

To a stirred suspension of 5.7 g (0.15 mole) of lithium aluminum hydride in 350 ml of dry ethyl was added dropwise (30 min) a solution of 25.0 g (0.149 mole) of 3-phenoxypropionic acid (99%, Aldrich Chem. Co.) in 250 ml of dry ethyl ether. The reaction mixture was stirred at ambient temperature for 2 hr and treated successively with 6 ml of water, 18 ml of a 15% sodium hydroxide solution, and 10 ml of water. The reaction mixture was filtered through Celite ® and the filtrate was concentrated to a viscous residue. The residue was partitioned between water and ethyl ether (300 ml each). The ethereal layer was washed with two 300 ml portions of water, dried over magnesium sulfate and the solvent was evaporated under reduced pressure to give 16.6 g (73%) of colorless oil.

Analysis: Calculated for $C_9H_{12}O_2$: C, 71.03; H, 7.95; Found: C, 71.09; H, 8.10.

PREPARATION 3

Benzenebutanol.

To a stirred suspension of 7.9 g (0.21 mole) of lithium aluminum hydride (Aldrich) in 350 ml of dry ethyl ether was added dropwise a solution of 32.8 g (0.2 mole) of 4-phenylbutyric acid (Aldrich) in 250 ml of dry ethyl ether. The reaction mixture was stirred at ambient temperature for 2 hr, treated successively with 8 ml of water, 25 ml of a 15% sodium hydroxide solution and 8 ml of water, and filtered through Celite ®. The filtrate was washed successively with water (200 ml), twice with 300 ml portions of sodium bicarbonate solution, 300 ml of water and dried over magnesium sulfate. The solvent was evaporated under reduced pressure to give 25.0 g (83%) of colorless oil.

Analysis: Calculated for $C_{10}H_{14}O$: C, 79.96; H, 9.39; Found: C, 79.87; H, 9.32.

PREPARATION 4

2-(3-Methoxyphenoxy)ethanol.

This compound was prepared by the procedure of Preparation 2. Thus, 36.5 g (0.2 mole) of 3-methoxyphenoxyacetic acid (Lancaster Synthesis, Inc., Windham, N.H. 03087) and 7.7 g (0.2 mole) of lithium aluminum hydride (Aldrich) in 600 ml of ethyl ether gave 25.7 g (76%) of light-yellow oil.

Analysis: Calculated for $C_9H_{12}O_3$: C, 64.27; H, 7.19; Found: C, 63.93; N, 7.10.

PREPARATION 5

2-(6-Methoxy-2-naphthyl)propanol.

This compound was prepared by the procedure used of Preparation 2. Thus, 39.2 g (0.170 mole) of (+)-6-methoxy-α-methyl-2-naphthaleneacetic acid (Naproxen; Sigma) and 6.5 g (0.171 mole) of lithium aluminum hydride (Aldrich) in 600 ml of ethyl ether gave 32.3 g (88% yield) of the title compound, a white solid. A 4.9 g sample of this solid was recrystallized from ethyl ether to give 4.7 g (96% recovery) of white solid, mp 89.5°–91.5° C.

Analysis: Calculated for $C_{14}H_{16}O_2$: C, 77.75; H, 7.46; Found: C, 77.57; H, 7.43.

PREPARATION 6

2-Phenoxy-2,2-dimethyl acetic acid.

To a solution of 20.0 g (0.93 mole) of 2-(4-chlorophenoxy)-2-methylpropionic acid (97%, clofibric acid, Aldrich) in 130 ml of methanol and 50 ml of dioxane was added a solution of 13.9 g (0.244 mole) of potassium hydroxide in 75 ml of water. To this solution were added 5 teaspoonfuls of Raney Nickel (Aldrich) and the mixture was hydrogenated at ambient temperature for 3.25 hr ($H_2$-uptake ceased). The reaction mixture was filtered through Celite® and the filtrate was concentrated under reduced pressure to a volume of 150 ml. This solution was extracted with 200 ml of ethyl ether and the ether was discarded. The aqueous layer pH was adjusted to 2 with concentrated hydrochloric acid solution and the resulting white solid was collected by filtration and dried to give 16 g (99%) of white solid. An analytical sample was prepared by recrystallizing from cyclohexane-petroleum ether (b.p. range 30°–60° C.) to give white crystals, mp 98°–100° C.

Analysis: Calculated for $C_{10}H_{12}O_3$: C, 66.65; H, 6.71; Found: C, 66.53; H, 6.72.

PREPARATION 7

2-(Methylphenoxy)ethanol.

The title compound was prepared by the procedure of Preparation 2 in 89% yield from 2-(methylphenoxy) acetic acid and lithium aluminum hydride.

PREPARATION 8

4-Phenoxy-1-butanol.

The title compound was prepared by the procedure of Preparation 2 in 91% yield from 4-phenoxy-1-butanoic acid and lithium aluminum hydride.

PREPARATION 9

2-(4-Methoxyphenoxy)ethanol.

A mixture of 148.8 g (1.20 mole) of p-methoxyphenol, 170.0 g (2.11 mole) of 2-chloroethanol and 47.2 g (1.18 mole) of sodium hydroxide in 1.5 liter of absolute ethanol was heated at reflux for 22 hr. The solution was filtered, and the solvent was removed from the filtrate in vacuo. The residue was crystallized from methylene chloride-hexane to give 71.4 g (35%) of title compound as a white crystalline solid, mp 69°–71° C.

Analysis: Calculated for $C_9H_{12}O_3$: C, 64.27; H, 7.19; Found: C, 64.18; H, 7.25.

PREPARATION 10

Benzenepentanol.

The title compound was prepared by the procedure of Preparation 2 in 87% yield from 5-phenylvaleric acid (Aldrich Chem. Co.) and lithium aluminum hydride.

PREPARATION 11

2-[4-(2-Methylpropyl)phenyl]-propan-1-ol.

The title compound was prepared by the procedure of Preparation 2 in quantitative yield from α-methyl-4-(2-methylpropyl)benzeneacetic acid which is Ibuprofen® and lithium aluminum hydride.

PREPARATION 12

2-Phenoxypropanol.

The title compound was prepared by the procedure of Preparation 2 in quantitative yield from 2-phenoxypropionic acid (Aldrich Chem. Co.) and lithium aluminum hydride.

PREPARATION 13

2-(4-Chlorophenoxy)-2-methylpropanol.

The title compound was prepared by the procedure of Preparation 2 in quantitative yield from clofibric acid (Aldrich Chem. Co.) and lithium aluminum hydride.

PREPARATION 14

2-(3-chlorophenoxy)ethanol.

A mixture of 51.4 g (0.4 mole) of 3-chlorophenol (Aldrich Chem. Co.), 34.7 g (0.43 mole) of 2-chloroethanol (Aldrich) and 16.1 g (0.4 mole) of sodium hydroxide pellets in 500 ml of 95% ethanol was stirred and heated at reflux for 16 hr. The mixture was filtered and the filtrate was evaporated under reduced pressure to yield a semisolid residue. The residue was partitioned between methylene chloride and a 15% sodium hydroxide solution (300 ml of each). The organic layer was washed with two 300 ml portions of water, dried over magnesium sulfate and the solvent was evaporated under reduced pressure to give 34.2 g (50%) of the title compound as a viscous oil.

PREPARATION 15

2-(3,4-Dichlorophenoxy)ethanol.

The title compound was prepared by reduction of 2-(3-4-dichlorophenoxy)acetic acid (Aldrich, 96% pure) with borane in tetrahydrofuran (Aldrich/M solution) using the procedure of N. M. Yoon, et al. in J. Org. Chem 38(#16) p. 2786 (1973). The yield was 91% of theory.

PREPARATION 16

3-Benzoylpropanol.

A solution of 35.6 g (0.20 mole) of benzoylpropionic acid in 100 ml of tetrahydrofuran was added dropwise to 300 ml of a 1 molar solution of borane tetrahydrofuran complex in tetrahydrofuran. The mixture was stirred at ambient temperatures for 60 hr, giving a gel. This was treated with 100 ml of 2N hydrochloric acid solution and the mixture stirred for 15 min. Most of the tetrahydrofuran was removed on a rotary evaporator and the residue partitioned between methylene chloride and water. The aqueous layer was extracted again with methylene chloride. The combined extract was washed with water, dried (sodium sulfate), and concentrated to yield 24.30 g of 1-phenyl-1,4-butanediol. This intermediate was dissolved in acetone and heated at reflux temperature for 5 hr while 30 g of manganese dioxide was added in five portions. The reaction mixture was filtered and concentrated to a brown oil that was chromatographed on silica gel using 15% ethyl acetate-85% methylene chloride to elute the fraction identified by $^1H$ nmr as the title compound. The fraction weighed 11.20 g, after concentration and was shown to have a purity greater than 90%.

PREPARATION 17

1-(3-Hydroxypropyl)indoline.

A stirred reaction mixture consisting of 22.5 ml (0.20 mole) of indoline, 29.8 ml (0.30 mole) of 3-chloropropanol, 41.4 g (0.30 mole) of potassium carbonate, 0.5 g of tetra-n-butylammonium bromide, 150 ml of toluene, and 50 ml of water was heated at reflux temperature for 5 hr. An additional 15 ml (0.15 mole) of 3-chloropropanol was added and reflux continued for an additional 23 hr. Thin layer chromatographic (TLC) analysis (10% ethyl acetate in methylene chloride) showed the reaction to be about 50% complete. Additional potassium carbonate (20 g), tetra-n-butylammonium bromide (0.5 g) and 3-chloropropanol (15 ml) were added to the reaction mixture which was then heated at reflux temperature for another 18 hr. Tlc analysis showed the reaction to be 66% complete. The mixture was diluted with water and toluene. The toluene layer was separated, washed twice with water, and then extracted twice with 2N hydrochloric acid solution. The acid extracts were washed once with toluene and combined. Toluene was added to the acid extract and the mixture basified by agitating while adding 50% sodium hydroxide solution. The organic layer was separated, washed with water, and the wash back extracted with toluene. The toluene solutions were combined, dried (sodium sulfate) and concentrated to give 25.7 g of a dark brown oil which was purified by chromatography on a 380 g column of silica gel using increasing portions of ethyl acetate in methylene chloride to elute the desired product (12.3 g).

PREPARATION 18

1-(3-Hydroxypropyl)indole.

In an exothermic reaction, a solution of 7.0 g (0.042 mole) of 1-(3-hydroxypropyl)indoline in 50 ml of acetone was added in a thin stream to a stirred suspension of 14 g of activated manganese dioxide in 100 ml of acetone. The mixture was stirred for 1 hr without addition of heat and then heated to reflux temperature for 1 hour. The reaction mixture was filtered and the filter cake washed with additional acetone. The filtrate, containing suspended solids, was treated with activated charcoal and filtered through a sintered glass funnel. The clear filtrate was evaporated to obtain 6.4 g of brown oil shown by $^1$H nmr and mass spectral analyses to be the title compound.

PREPARATION 19

2-(8-Quinolyloxy)ethanol.

A mixture of 14.5 g (0.10 mole) of 8-hydroxyquinoline, 13.5 ml (0.20 mole) of chloroethanol, 40 g (0.30 mole) of potassium carbonate, and 200 ml of acetone was stirred at reflux temperature for 26 hr. The mixture was filtered and the filtrate concentrated to an oil. The oil was partitioned between toluene and aqueous potassium carbonate solution. When the toluene solution was shaken with a fresh portion of potassium carbonate solution, an off-white solid crystallized out of solution. The solid was collected by filtration and the organic layer of the filtrate extracted twice with potassium carbonate solution. The toluene solution was concentrated to obtain a black oil. The oil was redissolved in toluene and upon treating the solution with a few drops of water, a solid crystallized from solution. This solid was collected by filtration and combined with the previously obtained solid. The solid was dissolved in hot methylene chloride, stirred with magnesium sulfate and charcoal, filtered, and concentrated to an oil. The oil was crystallized by dissolving in toluene and wetting the solution with a few drops of water, affording two crops of solid (5.5 g) which was shown by $^1$H nmr to be a dihydrate. The dihydrate was dissolved in a mixture of methylene chloride and toluene. The solution was dried (sodium sulfate), and concentrated to give 5.4 g of the anhydrous product as an oil.

PREPARATION 20

2-(3-Pyridyloxy)ethanol.

This compound was prepared according to the procedure in Preparation 19. Thus, reacting 14 g (0.15 mole) of 3-hydroxypyridine with 27 ml (0.4 mole) of 2-chlorethanol and 85 g of potassium carbonate in 150 ml of 2-butanone at reflux temperature gave 4.9 g of the title compound after column chromatography (5% methanol in methylene chloride on silica gel).

PREPARATION 21

Sulfamoyl chloride. (Ex. 3, pt.a) (Ex. 8, pt. a) (Ex. 12, pt. a)

A solution of 3.45 ml (0.1 mole) of 96% formic acid in 10 ml of acetonitrile was added over 15 min to a chilled (15° C.) solution of 8.87 ml (0.1 mole) of chlorosulfonyl isocyanate in 20 ml of acetonitrile. The reaction mixture was then stirred at ambient temperature for 3 hr (evolution of gas ceased during this time). This solution can be stored (0° C.) for future use.

PREPARATION 22

N-Isopropylsulfamoyl chloride. (Ex. 10, pt. a)

This was prepared in 47% yield from isopropylamine hydrochloride, sulfuryl chloride, and antimony (V) pentachloride in acetonitrile, using the procedure of G. Weis and G. Shulze, *Liebigs. Ann. Chem.* 729, 40 (1969).

PREPARATION 23

N-(t-Butylsulfamoyl) chloride.

This compound was prepared in 12% yield from t-butyl amine hydrochloride, sulfuryl chloride, and antimony (V) pentachloride in acetonitrile using the procedure of G. Weis and G. Schulze, *Liebigs. Ann. Chem.* 729, 40 (1969).

PREPARATION 24

N-Methylsulfamoyl chloride. (Ex. 4, pt. a)

This compound was prepared in approximately 80% yield from methylamine hydrochloride, sulfuryl chloride, and antimony (V) pentachloride in acetonitrile using the procedure of G. Weis and G. Schulze, *Liebigs. Ann. Chem.* 729, 40 (1969).

PREPARATION 25

N-Ethylsulfamoyl chloride.

This compound was prepared in 67% yield from ethylamine hydrochloride, sulfuryl chloride, and antimony (V) pentachloride in acetonitrile using the procedure of G. Weis and G. Schulze, *Liebigs. Ann. Chem.* 729, 40 (1969).

PREPARATION 26

3-Hydroxy-4-phenyl-1,2,5-thiadiazole.

3-Hydroxy-4-phenyl-1,2,5-thiadiazole was prepared from 2-amino-2-phenyl acetamide and sulfur monochloride in dimethylformamide in 85% yield using the procedure of L. M. Weinstock et al., *J. Org. Chem.* 32, 2823 (1967).

PREPARATION 27

2-Phenoxy-1,3-propanediol.

To a stirred solution of 11.9 g (0.517 mole) of sodium in 500 ml of absolute ethanol was added in portions 48.4 g (0.514 mole) of phenol. After stirring a few minutes to form the sodium phenoxide, 100 g (0.514 mole) of diethyl 2-chloromalonate was added dropwise. The reaction mixture was then heated at reflux temperature for 5 hr. The mixture was concentrated in vacuo and the residue treated with 500 ml of water. This mixture was extracted with three 300 ml portions of ether. The combined extract was washed with 300 ml of water, dried (magnesium sulfate) and concentrated to obtain 107 g (82% yield) of diethyl 2-phenoxymalonate.

A solution of 84.7 g of the ester in 250 ml anhydrous ether was added dropwise to a stirred suspension of 14.1 g (0.372 mole) of lithium aluminum hydride in 350 ml of anhydrous ether at such a rate so as to maintain a gentle reflux. When the addition was completed the mixture was stirred at ambient temperature for 2 hr and then treated cautiously with successive dropwise additions of 14 g of water, 42 g of 15% sodium hydroxide solution, and 42 g of water while the mixture was stirred vigorously. The mixture was then treated with 300 ml of ethyl acetate and stirred for a few minutes. The mixture was then filtered, the filter cake washed with an additional 300 ml of ethylacetate, and the combined filtrate layers washed twice with 400 ml portions of water. The organic solution was dried (magnesium sulfate) and concentrated in vacuo to give 39 g (69% yield) of the title compound as a viscous oil.

PREPARATION 28

1,1-Dimethyl-2-phenoxyethanol.

To a stirred solution of 24.2 g (0.16 mole) of phenoxy-2-propanone (Eastman) in 150 mL of dry ethyl ether was added 56 ml (0.17 mole) of methylmagnesium bromide (3.0M solution in ethyl ether, Aldrich) and the reaction mixture was stirred at ambient temperature under a nitrogen atmosphere for 4 hr. The reaction mixture was treated with 100 ml of saturated ammonium chloride solution and vigorously stirred for 1 hr. The layers were separated and the organic layer was washed twice with 200 ml portions of water, dried (magnesium sulfate) and the solvent evaporated under reduced pressure to yield 24.3 g (91%) of a vicous oil. A 2.3 g sample of the oil was purified by high pressure liquid chromatography (Waters Associates Prep LC/System 500 A, PrePAK 500/silica, ethyl acetate-hexanes, 1:20, flow rate 150 ml/min). The desired fractions were combined and the solvents evaporated under reduced pressure to yield 2.1 g (91% recovery) of the title compound as a colorless liquid.

Analysis: Calculated for $C_{10}H_{14}O_2$: C, 72.26; H, 8.49; Found: C, 72.08; H, 8.46.

PREPARATION 29

3-(1H-Imidazol-1-yl)phenol.

This compound was prepared by modifying a procedure of L. M. Sitkina and A. M. Simonov abstracted in CA 65:1386e.

Imidazole (34 g, 0.5 mole), m-bromoanisole (51 mL, 0.4 mole), potassium carbonate (52 g), and cuprous chloride (2.4 g) in 300 ml N-methyl-2-pyrrolidone was heated at reflux for 4 hours. The cooled mixture was diluted with water and 100 ml concentrated ammonium hydroxide. The product was extracted into toluene-ethylacetate (several times until TLC of aqueous layer showed only a trace amount of product). All the organic extracts were combined, filtered, extracted once with water and then three times with a total of 300 ml 48% hydrobromic acid. The hydrobromic acid extracts were combined and heated at reflux for 6 hours and then concentrated. The residue was redissolved in water and basified first with sodium hydroxide and at the end with sodium bicarbonate to get a final pH of 8. Some isopropyl ether was added to cause the product to crystallize out. The solid was filtered, rinsed with water, and dried at 80° C. in a vacuum oven to obtain 50.9 g (79.5% yield). A small portion of this solid was dissolved in absolute ethanol, filtered, concentrated, and recrystallized. The recrystallized material melted at 169°-170° C.

Analysis: Calculated for $C_9H_8N_2O$: C, 67.49; H, 5.03; N, 17.49; Found: C, 67.28; H, 5.12; N, 17.16.

PREPARATION 30

R-(−)2,2-Dimethyl-4(2-methoxyphenoxy)-1,3-dioxolane.

This compound was prepared from 5.72 g (0.02 mole) of S(+)-3-tosyloxy-1,2-propanediol acetonide and 0.03 mole of sodium guaiacolate in 76% yield according to the procedure of W. L. Nelson et al., *J. Org. Chem.* 42, 1066, 1977. Mp=43°-44° C., $[\alpha]_D^{22} - 8.0°$ (C=2 in dimethylformamide).

Analysis: Calculated for $C_{13}H_{18}O_4$: C, 65.53; H, 7.61; Found: C, 65.38; H, 7.45.

PREPARATION 31

S-(+)2,2-Dimethyl-4-(2-methoxyphenoxy)-1,3-dioxolane.

This compound was prepared from 49.4 g (0.173 mole) of R(−)-3-tosyloxy-1,2-propanediol acetonide and 0.26 mole of sodium guaiacolate in 68% yield according to the procedure of W. L. Nelson et al., *J. Org. Chem.* 42, 1066, 1977. Mp=44.5-45.5, $[\alpha]_D^{22} + 8.5°$ (C=2 in dimethylformamide).

Analysis: Calculated for $C_{13}H_{18}O_4$: C, 65.53; H, 7.61; Found: C, 65.53; H, 7.69.

PREPARATION 32

S-(+)-Glyceryl guaiacolate.

Hydrolysis of 20 g (0.084 mole) of R-(−)-2,2-dimethyl-4(2-methoxyphenoxy)-1,3-dioxolane according to the procedure of W. L. Nelson et al, *J. Org. Chem.* 42, 1066 (1977) gave 14.2 g (85%) of the title compound, mp 93°-94.5° C., $[\alpha]_D^{22} + 8.80°$ (C=2 in methanol).

Analysis: Calculated for $C_{10}H_{14}O_4$: C, 60.60; H, 7.12; Found: C, 60.53; H, 6.98.

PREPARATION 33

R-(−)Glyceryl guaiacolate.

Hydrolysis of 27.0 g (0.113 mole) of S-(+)-2,2-dimethyl-4(2-methoxyphenoxy)-1,3-dioxolane according to the procedure of W. L. Nelson et al, *J. Org. Chem.* 43, 1066 (1977) gave 21.5 g (96%) of the title compound, mp 93.5°-95° C., $[\alpha]_D^{22} - 9.05°$ (C=2 in methanol).

Analysis: Calculated for $C_{10}H_{14}O_4$: C, 60.60; H, 7.12; Found: C, 60.56; H, 7.05.

PREPARATION 34

3-(4-Phenyl-1H-imidazol-1-yl)phenol.

Following the procedure for preparation of 3-(1H-imidazol-1-yl) phenol (preparation 29), 4- phenylimidazole (20 g, 0.138 mole) and 3-bromoanisole (32 ml, 0.25 mole) were reacted to give the title compound in 57% yield; mp 195°–197° C.

Analysis: Calculated for $C_{15}H_{12}O$: C, 76.25; H, 11.86; Found: C, 75.98; H, 11.67.

PREPARATION 35

2-[3-(1H-Imidazol-1-yl)phenoxy]ethanol.

A slurry of 16.0 g (0.10 mole) of 3-(imidazol-1-yl)phenol and 42 g (0.3 mole) of potassium carbonate in 100 ml of methyl ethyl ketone was heated to reflux with stirring. The mixture was treated with 25.5 g (0.3 mole) of chloroethanol by dropwise addition over a 2 hr period. The mixture was heated at reflux for an additional 18 hr then treated with an additional 16.1 g (0.2 mole) of chloroethanol and 27.6 (0.2 mol) of potassium carbonate. After an additional 22 hr heating at reflux all starting material was consumed. The reaction mixture was filtered and the filtrate was concentrated. The residue was partitioned between methylene chloride and 0.1N sodium hydroxide solution. The organic layer was concentrated and the residue was crystallized from ethyl acetate to give 10.2 g (50%) of the title compound as tan crystals, mp 81.0°–83.0° C.

Analysis: Calculated for $C_{11}H_{12}N_2O_2$: C, 64.69; H, 5.92; N, 13.72; Found: C, 64.50; H, 5.87; N, 13.56.

PREPARATION 36

3-(2-Ethoxyphenoxy)-1,2-propanediol.

A solution of 41.5 g (0.3 mole) of 2-ethoxyphenol, 29.6 g (0.4 mole) of glycidol, 2 ml of pyridine and 150 ml of absolute ethanol was heated at reflux temperature for 18 hr. The mixture was concentrated to a thick oil that crystallized slowly over several days. The crude product was chromatographed on a silica gel column (1.2 kg) using increasing portions of acetone in methylene chloride to elute the product. The desired fractions were combined and concentrated to give a yellow oil that crystallized on standing. The solid was triturated with petroleum ether and the mixture filtered to obtain 41.8 g of solid. Recrystallization from carbon tetrachloride yielded 37.2 g (58%) of white solid, mp 64°–65° C.

Analysis: Calculated for $C_{11}H_6O_4$: C, 62.25; H, 7.60; Found: C, 62.34; H, 7.72.

PREPARATION 37

3-[4-(1H-Imidazol-1-yl)phenoxy]-1-propanol.

A stirred mixture of 4(1H-imidazol-1-yl)phenol (16.0 g, 0.10 mole), 3-chloropropanol (19.0 g, 0.20 mole), potassium carbonate (28 g, 0.20 mole) and methyl ethyl ketone (100 ml) was heated at reflux temperature for 24 hr. The reaction mixture was cooled, filtered, and the filtrate concentrated. The residue was partitioned between ethyl acetate and 0.01N sodium hydroxide solution. The ethyl acetate layer was dried (magnesium sulfate), diluted with ether, and the solid precipitate collected. The solid was recrystallized from methyl isobutyl ketone to obtain 10.0 g (46%), mp 76°–78° C.

Analysis: Calculated for $C_{12}H_{19}N_2O_4$: C, 66.04; H, 6.47; N, 12.84; Found: C, 65.87; H, 6.48; N, 12.71.

PREPARATION 38

2-[4-(1H-1,2,4-Triazol-1-yl)phenoxy]ethanol.

A stirred mixture of 4(1H-1,2,4-triazol-1-yl)phenol (16.1 g, 0.10 mole), 2-chloroethanol (25.5 g, 0.30 mole), potassium carbonate (42 g, 0.30 mole) and methyl ethyl ketone (100 ml) was heated at reflux temperature for 10 hr. An additional 16.1 g (0.20 mole) of 2-chloroethanol was added to the reaction mixture and heating at reflux temperature continued for another 24 hr. The hot mixture was filtered and the filtrate chilled. The crystalline precipitate was collected by filtration and the filter cake rinsed with water to remove most of the dark color. The solid was triturated with hot ethyl acetate, the mixture cooled, and the light tan crystals collected to yield 14.0 g (68%); mp 151°–152° C.

Analysis: Calculated for $C_{10}H_{11}N_3O_2$: C, 58.53; H, 5.40; N, 20.48; Found: C, 58.35; H, 5.36; N, 20.27.

PREPARATION 39

3-(2-Methyl-1H-imidazol-1-yl)phenol.

A stirred mixture of 3-bromoanisole (100 g, 0.53 mole), 2-methylimidazole (41 g, 0.50 mole), potassium carbonate (96 g, 0.60 mole), cuprous chloride (2.5 g) and N-methyl-2-pyrrolidinone (300 ml) was heated at reflux temperature for 15 hr and then concentrated to remove the solvent and excess 3-bromoanisole. The residue was partitioned between ethyl acetate and water. The ethyl acetate layer was concentrated to a black syrup that was then dissolved in toluene and extracted twice with water and then extracted with 48% hydrobromic acid solution. The hydrobomic acid extract was heated at reflux temperature for 7 hr and then distillation of water and methylbromide was begun with addition of additional 48% hydrobromic acid solution as necessary to maintain a reasonable volume. Distillation was continued until the distillation head temperature reached 124° C. The mixture was concentrated under vacuum. The concentrate was diluted with 500 ml of water and basified to pH 8 with addition of potassium carbonate in small portions. The precipitate was collected, washed with water, and dried to give 39.7 g. Recrystallization from 50% aqueous ethanol gave 31.4 g (36%), mp 178°–181° C.

Analysis: Calculated for $C_{10}H_{10}N_2O$: C, 68.95; H, 5.79; N, 16.08; Found: C, 68.71; H, 5.75; N, 15.94.

PREPARATION 40

2-Methyl-2-phenoxy-1-propanol.

This compound was prepared in 94% yield by reduction of 2,2-dimethylphenoxyacetic acid with a 1 molar solution of borane-tetrahydrofuran in tetrahydrofuran (Aldrich Chemical Co.) using the procedure of N. M. Yoon et al, *J. Org. Chem.* 38, 2786 (1973).

PREPARATION 41

3-(4-Methyl-1H-imidazol-1-yl)phenol.

A mixture of 3-bromoanisole (25.5 ml, 0.2 mole), 4-methyl-imidazole (21 g, 0.25 mole), potassium carbonate (26 g), and cuprous chloride (1.2 g) in 150 ml N-methyl-2-pyrrolidone was reacted and worked up as described in Preparation 29.

The phenolic product isolated as precipitate from water had a slightly wet weight of 31 g and $^{13}C$ NMR showed a 4:1 isomer ratio. This solid was dissolved in hot isopropyl alcohol, charcoaled, filtered, concentrated, and crystallized to give 11.69 g of off-white solid. $^{13}C$ NMR showed only the major isomer, mp 203°–5° C.

Analysis: Calculated for $C_{10}H_{10}N_2O$: C, 68.95; H, 5.79; N, 16.08; Found: C, 69.32; H, 5.68; N, 16.08.

PREPARATION 42

2-(2-methoxyphenoxy)ethanol.

A solution of 43.2 g (0.35 mole) of 2-methoxyphenol (guaiacol, Aldrich) in 200 ml of ethanol was stirred and treated with 29 ml (0.36 mole) of 50% sodium hydroxide solution. To this solution was added a solution of 28.2 g (0.35 mole) of 2-chloroethanol (Aldrich) in 50 ml of ethanol and the reaction mixture was heated at reflux for 2 hr. The solids were removed by filtration. The filtrate was evaporated under reduced pressure and the viscous residue was partitioned between 300 ml of 15% sodium hydroxide solution and 500 ml of ethyl ether. The organic layer was washed with 200 ml of 15% sodium hydroxide solution, 300 ml of water, dried (magnesium sulfate) and the solvent evaporated under reduced pressure to give 24.5 g (42%) of the title compound as a lightly colored viscous oil.

An analytical sample was prepared from this oil by high pressure liquid chromatography purification (Waters Associates Prep LC/System 500 A, PrePak 500 silica, ethyl acetate-hexanes, 1:2, flow rate 200 ml/min). Fractions containing the title compound were combined and the solvents evaporated under reduced pressure to yield the title compound as a colorless liquid.

Analysis: Calculated for $C_9H_{12}O_3$: C, 64.27; H, 7.19; Found: C, 63.93; H, 7.32.

PREPARATION 43

3-[2-(Phenylmethoxy)phenoxy]-1,2-propanediol.

A solution of 49.6 g (0.248 mole) of 2-benzyloxyphenol, 22.2 g (0.3 mole) of glycidol, 2 ml of pyridine and 150 ml of absolute ethanol was heated at reflux overnight. The dark solution was concentrated to give an oil which gradually crystallized. The solid was purified by column chromatography on 1.2 kg of silica gel eluted with 0–25% acetone in benzene. Appropriate fractions were combined and concentrated to yield 49.5 g (73%) of the title compound as a white solid, mp 84°–85° C. (carbon tetrachloride) (lit.[1] mp 81°–82.5° C.).

[1]J. Swidinsky, J. Kervenski & B. B. Brown, J. Pharm. Sci. 52:955–8 (1963).

Analysis: Calculated for $C_{16}H_{18}O_4$: C, 70.06; H, 6.61; Found: C, 69.96; H, 6.60.

PREPARATION 44

2-[3-(4-Methyl-1H-imidazol-1-yl)phenoxy]ethanol monohydrochloride.

3-(4-Methyl-1H-imidazol-1-yl)phenol (13.1 g, 0.075 mole0, chloroethanol (20.2 ml, 0.3 mole), and potassium carbonate (42 g, 0.3 mole) were heated at reflux in 200 ml methyl ethyl ketone for 7 hours. TLC of a sample showed some starting phenol remaining. Chloroethanol (10 ml) was added to the reaction and it was kept at reflux temperature overnight. The solid was filtered and rinsed with acetone. The filtrate and rinsings were concentrated to an oil and dissolved in 1:1 acetonitrile-toluene. The filtered solid was dissolved in water and the solution was used to extract the organic solution. The aqueous layer was separated and extracted once more with 1:1 acetonitrile-toluene. The organic layers were washed with potassium carbonate solution, dried, filtered, and concentrated to give 16.7 g of dark brown oil. The oil was dissolved in 2-propanol and acidified with a solution of hydrogen chloride in 2-propanol and the salt crystallized from 2-propanol/isopropyl ether. The brown solid was collected and recrystallized from 2-propanol to give 9.07 g of light brown solid which was dried in a vacuum oven overnight at 60° C., mp 164°–165° C.

Analysis: Calculated for $C_{12}H_{14}N_2O_2 \cdot HCl$: C, 56.59; H, 5.94; N, 11.00; Found: C, 56.44; H, 6.03; N, 10.90.

PREPARATION 45

2-[3-(Phenylmethoxy)phenoxy]ethanol.

A slurry of 38.6 g (0.25 mole) of o-(2-hydroxyethyl)-resorcinol (Lancaster), 44.3 g (0.35 mole) of benzyl chloride, and 55.2 g (0.40 mole) of potassium carbonate in 200 ml of acetone was stirred and heated at reflux for 72 hr. The reaction mixture was filtered and the filtrate was concentrated under vacuum. The crystalline residue was recrystallized from toluene/petroleum ether to give 56.3 g (92%) of the title compound as white flakes, mp 40.5°–43.5° C.

Analysis: Calculated for $C_{15}H_{16}O_3$: C, 73.75; H, 6.60; Found: C, 73.68; H, 6.53.

PREPARATION 46

3-[2-(1H-imidazol-1-yl)ethoxy]phenol.

A solution of 12.2 g (0.05 mole) 2-[3-(phenylmethoxy)phenoxy]ethanol and 5.6 g (0.555 mole) of triethylamine in 100 ml of THF was cooled to 0° C. with stirring and treated dropwise with 6.4 g (0.055 mole) of mesyl chloride over a 20-min period. The mixture was stirred at 10° C. or less for 1 hr, then filtered. The filtrate was combined with a slurry of 0.10 mole of imidazole sodium salt in 50 ml of THF and the mixture was heated at reflux for 8 hr. The 50 ml of THF and the mixture was heated at reflux for 8 hr. The cooled reaction mixture was filtered and the filtrate was partitioned between ethyl acetate/ether and water. The organic layer was concentrated to give 14.7 g (100%) of crude intermediate. This syrup (13.0 g) was dissolved in 100 ml of methanol and hydrogenated at 40° C. and 45 psi $H_2$ using 1 g of 10% Pd/C catalyst. This mixture was filtered, and the filtrate was concentrated to give 9.0 g (100%) of crude, crystalline product. A portion was recrystallized from toluene/methyl isobutyl ketone to give the title compound as white crystals, mp 125.0° C.–127.0° C.

Analysis: Calculated for $C_{11}H_{12}N_2O_2$: C, 64.69; H, 5.92; N, 13.72; Found: C, 64.72; H, 5.97; N, 13.74.

PREPARATION 47

3-(4-Iodophenoxy)-1,2-propanediol.

A solution of 28.1 g (0.127 mole) of 4-iodophenol, 11.6 g (0.16 mole) of glycidol, 2 ml of pyridine, and 125 ml of absolute ethanol was heated at reflux overnight. The dark solution was concentrated to give a brown, solid residue. The residue was triturated several times with boiling carbon tetrachloride and the liquid decanted. The combined carbon tetrachloride washings were heated, filtered and cooled, and a solid crystallized. The solid was collected by filtration and dried to yield 9.4 g (25%) of a pale yellow solid. An analytical sample, mp 101.5°–103.5° C. (lit.[1] mp 106°–107° C.) was prepared from $CCl_4$.

[1]O. Radek and O. Nemecek, Cesk. Farm. 13,456–9 (1964); Chem. Abstr. 62, 3966f (1965).

Analysis: Calculated for $C_9H_{11}IO_3$: C, 36.76; H, 3.77; Found: C, 36.82; H, 3.81.

PREPARATION 48

2-(3-Nitrophenoxy)ethanol.

A mixture of m-nitrophenol (28 g, 0.2 mole), 2-chloroethanol (53.6 ml, 0.8 mole), and potassium carbonate (110.4 g, 0.8 mole) in 300 ml methyl ethyl ketone was kept at reflux temperature with stirring overnight. The solid was filtered and dissolved in water. The filtrate was concentrated and some wolid was crystallized from 2-propanol/isopropyl ether. This light-brown solid was collected and weighed 22.78 g (62%). The mother liquor was concentrated and redissolved in toluene/ethyl acetate and extracted with the above aqueous solution. The aqueous layer was further extracted with fresh toluene/ethyl acetate. The combined organic layers were washed with water, dried over sodium sulfate, filtered, and concentrated to give a second crop of 6.46 g (17.6%). The second crop was dissolved in methanol, stirred with charcoal, filtered, evaporated, and crystallized from 2-propanol/isopropyl ether to give a pure sample. The sample was dried under vacuum at room temperature overnight, mp 85°–86° C.

Analysis: Calculated for $C_8H_9NO_4$: C, 52.46; H, 4.95; N, 7.65; Found: C, 52.41; H, 4.96; N, 7.65.

PREPARATION 49

4-(2-Methyl-1H-imidazol-1-yl)phenol.

To a 3-neck, 1-liter, round-bottom flask was added 2-methylimidazole (41.0 g, 0.50 mole), 4-bromoanisole (100 g, 0.53 mole) and potassium carbonate (96.0 g, 0.70 mole) in N-methyl-2-pyrrolidinone (300 ml). A small amount of cuprous chloride (2.5 g) was added. The stirred reaction mixture was heated at reflux temperature for 24 hr and then the N-methyl-2-pyrrolidinone and excess bromoanisole gently distilled. The black pot residue was partitioned between toluene and water and a black solid removed by filtration. The toluene layer was extracted with 48% hydrobromic acid (2×200 ml) and the hydrobromic acid solution was heated at reflux temperature 3 hr then stirred at room temperature overnight. The solution was then concentrated, diluted with water (500 ml) and made basic with sodium hydroxide and sodium bicarbonate solutions. The white solid which precipitated was collected and cried and a small amount recrystallized from methanol/isopropyl alcohol. The total yield was 24.88g (28.6% yield), mp 205°–208° C.

Analysis: Calculated for $C_{10}H_{10}N_2O$: C, 68.95; H, 5.79; N, 16.08; Found: C, 68.58; H, 5.67; N, 15.84.

PREPARATION 50

4-(1-Methyl-1H-imidazol-2-yl)phenol.

Hydrogen chloride gas was bubbled through a chilled solution of p-cyanophenol (30 g, 0.25 mole) in methanol (120 mo) for 70 min. The heavy suspension was stoppered and stirred overnight. After cooling in an ice bath, the solid was collected by filtration and rinsed twice with cold methanol. The solid was dried under nitrogen to ive 46.56 g. The solid iminoether was resuspended in methanol (150 ml) and treated with methylamino acetaldehyde dimethyl acetal (42 ml, 0.325 m) and then heated at reflux temperature for 3 hr. The reaction was then concentrated to an oil which was redissolved in 2N hydrochloric acid solution (200 ml). The solution was then concentrated to remove the methanol and the resulting aqueous solution was extracted twice with methylene chloride and then made basic first with 50% sodium hydroxide solution and finishing up with 10% sodium bicarbonate solution. The solid was collected and rinsed with water, 2-propanol and isopropyl ether. The solid was dissolved in methanol, treated with charcoal and filtered. The filtrate was partially concentrated by boiling and replacing the methanol with 2-propanol, from which a white, crystalline solid precipitated out of solution. The solid was filtered and dried (14.4 g, 0.083 mole, 66.7% yield, mp 239°–242° C.).

Analysis: Calculated for $C_{10}H_{10}N_2O$: C, 68.95; H, 5.79; N, 16.08; Found: C, 69.17; H, 5.74; N, 16.16.

PREPARATION 51

2-[4-(2-Methyl-1H-imidazol-1-yl)phenoxy]ethanol.

4-(2-Methyl-1H-imidazol-1-yl)phenol (10.0g, 0.057 mole), 2-chloroethanol (13.88 g, 0.172 mole) and potassium carbonate (23.74 g, 0.172 mole) were combined in methyl ethyl ketone (200 ml) and heated at reflux temperature for four days. The solution was cooled and the solid filtered and rinsed with acetone. The filtrate was concentrated to a residue and the residue triturated with hot acetone (2×50 ml). The remaining solid (1.5 g) was dissolved in methylene chloride. Insoluble materials were removed by filtrateion, and the filtrate concentraed to obtain 0.50 g (4%), mp 125°–127° C. Proton NMR indicates that methylene chloride is present in the sample.

Analysis: Calculated for $C_{12}H_{14}N_2O_2 \bullet CH_2Cl_2$: C, 64.10; H, 6.31; N, 12.35; Found: C, 64.24; H, 6.36; N, 12.30.

PREPARATION 52

1-(4-Methoxyphenyl)-1H-imidazole.

A mixture of 37.4 g (0.20 mole) of 4-bromoanisole, 170 g (0.25 mole) of imidazole, 26 g (0.2 mole) of potassium carbonate, and 1.2 g of cuprous bromide in 150 ml of N-methylpyrrolidinone was heated at reflux under a blanket of nitrogen for 4 hr. The mixture was filtered and concentrated to remove the solvent. The residue was partitioned between dilute sodium hydroxide solution and methylene chloride. After filtration, the organic fraction was chromatographed. The desired fractions were concentrated and the crystalline residue was recrystallized from toluene/cyclohexane to give 17.4 g (50%) of the title compound as white plates, mp 63.0°–64.0° C.

Analysis: Calculated for $C_{10}H_{10}N_2O$: C, 68.95; H, 5.79; N, 16.08; Found: C, 68.91; H, 4.73; N, 16.05.

PREPARATION 53

2-(2-Methoxyphenoxy)propanedioic acid diethyl ester.

To a solution of 6.9 g (0.3 mole) of sodium pellets dissolved in 400 ml of absolute ethanol was successively added a solution of 37.9 g (0.305 mole) of guaiacol in 50 ml of ethanol followed by a solution of 68.1 g (0.35 mole) of diethylchloromalonate in 50 ml of ethanol. The mixture was heated at reflux for 28 hr and then stirred at ambient temperature for 3 days. The mixture was filtered and the filtrate was concentrated. The residue was partitioned between salt water and ethyl ether. The layers were separated and the aqueous layer was extracted twice with 150 ml portions of ethyl ether. The combined organic layers were washed with brine, dried (sodium sulfate0 and concentrated to give a yellow oil. The oil was subjected to vacuum distillation and 66.6 g (79%) of the title compound was collected as a clear oil, bp 136°–153° C. at 0.3 mm.

Analysis: Calculated for $C_{14}H_{13}O_6$: C, 59.57; H, 6.43; Found: C, 59.46; H, 6.67.

PREPARATION 54

2-(2-Phenoxyethyl)propane-1,3-diol.

A solution of 30.0 g (0.11 mole) of 2(phenoxyethyl)-diethyl malonate (Alfred Bader/Aldrich) in 100 ml of dry tetrahydrofuran (THF) was added dropwise to a stirred suspension of 6.1 g (0.16 mole) of lithium aluminum hydride (Aldrich) in 100 ml of dry THF. The reaction mixture was stirred at ambient temperature for 2 hr, treated successively with 15 ml of water, 20 ml of 15% sodium hydroxide solution and 25 ml of water. The solids were removed by filtration and the filter cake was washed with 100 ml of water and 300 ml of ethyl ether. The filtrate layers were separated and the organic layer was washed with two 300 ml fractions of water, dried (magnesium sulfate) and the solvents were evaporated under reduced pressure to give a colorless, miscous oil that solidified upon standing. The solid was recrystallized from methylene chloride to yield 12.4 g (59%) of a white solid, mp 71°-73° C.

Analysis: Calculated for $C_{11}H_{16}O_3$: C, 67.32; H, 8.22; Found: C, 57.33; H, 8.40.

PREPARATION 55

2-(4-Chlorophenoxy)propanedioic acid diethyl ester.

A mixture of 38.6 g (0.3 mole) of 4-chlorophenol, 70 g (0.36 mole) of diethylchloromalonate and 69.1 g (0.5 mole) of anhydrous potassium carbonate in 750 ml of acetone was heated at reflux for 48 hr, cooled, filtered and the filtrate concentrated. The residue was diluted with 250 ml of ethyl ether and was washed successively with two 100 ml portions of a 1% NaOH solution, once with $H_2O$ and once with brine, dried (sodium sulfate) and concentrated to give an oil which gradually crystallized. The solid was triturated with petroleum ether (30°-60° C.), collected by filtration and dried to yield 72.6 g (84%) of white solid. An analytical sample, mp 43.5°-45° C. (lit. mp 58°-60° C.), was recrystallized from petroleum ether (60°-110° C.).

Analysis: Calculated for $C_{13}H_{15}ClO_5$: C, 54.46; H, 5.27; Found: C, 54.49; H, 5.35.

PREPARATION 56

2-(2-Naphthyloxy)propanedioic acid diethyl ester.

This compound was prepared following Procedure 55. Thus, a mixture of 43.2 g (0.3 mole) of 2-haphthol, 70 g (0.36 mole) of diethylchloromalonate and 69.1 g (0.5 mole) of anhydrous potassium carbonate in 750 ml of acetone gave 84.0 g (93%) of a tan solid. An analytical sample, mp 57°-58.5° C. (lit.[1] mp 57°-58° C.), was recrystallized from isopropyl ether.

Analysis: Calculated for $C_{17}H_{18}O_5$: C, 67.54; H, 6.00; Found: C, 57.58; H, 6.05.

PREPARATION 57

2-(4-Phenylmethoxy)phenoxy ethanol.

A mixture of 130.4 g (0.65 mole) of 4-benzyloxyphenol (Eastman), 93.0 g (1.16 mole) of 2-chloroethanol (Aldrich) and 26.0 g (0.65 mole) of sodium hydroxide pellets in 750 ml of ethanol was stirred and heated at reflux for 20 hr. The reaction mixture was filtered and the filtrate was concentrated under reduced pressure to a solid residue. The solid was partitioned between 300 ml of 15% sodium hydroxide solution and 600 ml of methylene chloride. The organic layer was further washed with 200 ml of 15% sodium hydroxide solution, two 300 ml fractions of water, dried (magnesium sulfate) and the solvent was evaporated under reduced pressure to give 81.0 g of a solid. The solid was recrystallized (charcoal treated) from methylene chloride-petroleum ether (30°-60° C.) to give 78.5 g (92%, based on amount of 4-benzyloxyphenol consumed) of crystals, mp 102.5°-104.5° C.

Analysis: Calculated for $C_{15}H_{16}O_3$: C, 73.75, H, 6.60; Found: C, 73.73; H, 6.72.

PREPARATION 58

4-(4,5-Dihydro-1-methyl-1H-imidazol-2-yl)phenol hemihydrate.

Anhydrous hydrogen chloride gas was bubbled into a cold (0° C.) stirred solution of p-cyanophenol (30 g, 0.25 mole) in 120 ml methanol for 70 min. The resultant heavy suspension was stoppered and stirred overnight. After cooling in an ice bath, the solid was collected by filtration and rinsed twice with cold methanol. The solid was then dried under nitrogen to a weight of 46.56 g. The solid was resuspended in 150 ml methanol, chilled in an ice bath, and N-methylethylenediamine (22 g, 0.25 mole) was added. The reaction became a clear solution and it was heated at reflux temperature for one hour. The solvent was then evaporated and the residual oil was dissolved in water. It was basified first using 50% sodium hydroxide solution and then using sodium bicarbonate solution. The solid was collected by filtration and rinsed with water, 2-propanol, and isopropyl ether. The slightly wet solid weighted 20.71 g. The mother liquor and rinsings were combined and concentrated to yield a second crop which weighed 22.5 g. A portion of the first crop was recrystallized from acetonitrile/methanol, filtered and dried, mp 122°-125° C.

Analysis: Calculated for $C_{10}H_{12}N_2O \bullet 0.5H_2O$: C, 64.85; H, 7.07; N, 15.12; Found: C, 65.19; H, 7.08; N, 15.17.

PREPARATION 59

1-(2-Chloro-5-methoxyphenyl)-1H-imidazole.

A mixture of 6-chloro-m-anisidine hydrochloride (21.48 g, 0.11 mole), triethylamine (15.2 ml, 0.11 mole) and 150 ml trimethyl orthoformate was heated at reflux for 3.5 hours. To the mixture was added 150 ml of toluene and some charcoal. After stirring, the mixture was filtered and the filtrate was evaporated to an oil. The oil was redissolved in 150 ml of methanol and reacted with aminoacetaldehyde dimethyl acetal (12 ml, 0.11 mole) at reflux for four hours. The reaction was concentrated and the residue was dissolved in toluene. The toluene solution was extracted twice (total volume 100 ml) with 2N hydrochloric acid solution. The extracts were combined, heated at reflux temperature for five hours, and then concentrated. The residue was dissolved in water and neutralized first with 50% sodium hydroxide and finished up with sodium bicarbonate solution. Some oily material deposited and crystallized upon addition of toluene. The mixture was filtered, the layers of the filtrate were separated, and the aqueous layer extracted three times with toluene-acetonitrile. The organic layers were combined, dried over sodium sulfate, and concentrated to a dark brown oil (15 g). TLC (silica gel eluted with 10% methanol in methylene chloride) of this oil showed mainly two spots at $R_f 0.8$ and 0.2. The oil was chromatographed on 150 g of silica gel and eluted with 10% methanol in methylene chloride.

About 10 g material of $R_f 0.8$ was collected. A portion of this was recrystallized from toluene, collected and rinsed with toluene-isopropyl ether, and dried in vacuo at room temperature overnight to give an analytical sample, mp 79°-81° C.

Analysis: Calculated for $C_{10}H_9ClN_2O$: C, 57.57; H, 4.35; N, 13.43; Found: C, 57.48; H, 4.23; N, 13.36.

PREPARATION 60

2-(4-Chlorophenoxy)-1,3-propanediol.

To a stirred slurry of 11.4 g (0.3 mole) of lithium aluminum hydride (LAH) in 200 ml of freshly distilled (from LAH) tetrahydrofuran (THF) was added dropwise a solution of 57.3 g (0.2 mole) of 2-(4-chlorophenoxy)-1,3-propanedioil acid diethyl ester (C.A. 59:5051f (1963); Mamaev and Mikhaleva, *Isv. SIbirsk. Otd. Akad. Nauk. SSSR*, 145-8 (1962) in 150 ml of THF at such a rate that a gentle reflux was maintained. The mixture was stirred at ambient temperature for 5 hr and then the excess LAH was decomposed with successive, cautious, dropwise additions of 11.4 ml of water, 11.4 ml of a 15% sodium hydroxide solution, and 34 ml of water. A gelatinous precipitate developed which was filtered through Celite with great difficulty. The filtrate was concentrated and the residue was purified by column chromatography on 500 g of silica gel eluted with 0-35% acetone in benzene. The appropriate fractions were combined and concentrated to give an oil which gradually crystallized. The solid was triturated with petroleum ether (30°-60° C.), collected by filtration, and dried to yield 18.2 g (45%) of white solid, mp 62°-64° C. (isopropyl ether).

Analysis: Calculated for $C_9H_{11}ClO_3$: C, 53.35; H, 5.47; Found: C, 53.51; H, 5.52.

PREPARATION 61

4-Chloro-3-(1H-imidazol-1-yl)phenol.

1-chloro-2-(1H-imidazol-1-yl)-4-methoxybenzene (7.5 g, 0.036 m) was mixed with 40 ml 48% hydrobromic acid. The solution was distilled until the head temperature reached 120° C. and the reaction was then heated at reflux for two hours. The reaction was concentrated under reduced pressure. The residue was triturated in isopropyl alcohol-isopropyl ether and the solid was collected. The solid was dissolved in water and poured into a saturated solution of sodium bicarbonate. The solid was collected and rinsed with water, isopropyl alcohol-isopropyl ether, and isopropyl ether to give 6.65 g of solid. A small portion of this solid was recrystallized by dissolving in methanol-isopropyl alcohol, treated with charcoal, filtered, and evaporated to remove most of the methanol. A white solid was obtained which was dried at 70° C. under vacuum overnight, mp 204°-205° C.

Analysis: Calculated for $C_9H_7ClN_2O$: C, 55.54; H, 3.63; N, 14.39; Found: C, 55.37; H, 3.50; N, 14.36.

EXAMPLE 1

[1-[(2-Methoxyphenoxy)methyl]-1,2-ethanediylbis-(oxysulfonyl)]biscarbamic acid bis 1-methylethyl ester.

a. Preparation of the isopropyl ester of N-chlorosulfonyl carbamic acid.

To a solution of 154 g (1.09 mole) of chlorosulfonyl isocyanate in 300 ml of methylene chloride with agitation and cooling in an ice bath was added a solution of 83.2 ml (1.09 mole) of 2-propanol in 100 ml of methylene chloride over a 26 minute period. The ice bath was removed after addition was complete and the mixture was stirred for 2.5 hr. The mixture was filtered through a Celite ® cake to remove a small amount of solid. The filtrate was concentrated to a solid. The solid was triturated in petroleum ether and collected on a filter under nitrogen atmosphere, washed with more petroleum ether and dried under vacuum in a desicator to give 212.7 g (96.5%) of the isopropyl ester of N-chlorosulfonyl carbamic acid.

b. Preparation of the title compound.

Into a stirred solution of the 20.1 g (0.10 mole) of the isopropyl ester of N-chlorosulfonyl carbamic acid in 30 ml of methylene chloride, cooled by an ice bath was poured a suspension of 8 g (0.04 mole) of 3-(2-methoxyphenoxy)-1,2-propanediol (which is glyceryl guaiacolate) in a 8.1 ml (0.1 mole) of pyridine. Exothermic reaction caused gentle boiling. The ice bath was removed after the addition and stirring was continued for 2 hr. Water, 80 ml, was added to the reaction mixture and stirring continued for 20 min additional time. The organic layer was separated and washed twice more with water. The organic layer was extracted three times with sodium bicarbonate solution. The combined bicarbonate solution containing the product was stirred with methylene chloride in an ice bath with adding sulfuric acid to acidifying the mixture. The layers were separated and the aqueous layer was extracted once with methylene chloride. The methylene chloride layers were combined, washed with water, dried over sodium sulfate, filtered and concentrated to give 23 g of an oil. $^1H$ NMR analysis showed title compound with a small contamination of methylene chloride. A 10 g portion of the oil in benzene was freeze-dried in an attempt to obtain solid; however an oil resulted. $^1H$ NMR analysis showed methylene chloride had been exchanged for benzene in amount of about 0.25 mole benzene per mole of title compound.

Analysis: Calculated for $C_{18}H_{28}N_2O_{12}S_2$: C, 40.90; H, 5.34; N, 5.30; Found: C, 42.40; H, 5.47; N, 5.00.

EXAMPLE 2

[1-[(2-Methoxyphenoxy)methyl]-1,2-ethanediylbis-(oxysulfonyl)]-biscarbamic acid, bis-1-methylethyl ester, zinc complex dihydrate compound with 2-propanol (2:1).

To a solution of 22.39 g (0.042 mole) of [1-[(2-methoxyphenoxy)methyl]-1,2-ethanediylbis(oxysulfonyl)]biscarbamic acid bis 1-methylethyl ester (from Example 1) in methanol was added a light suspension of barium hydroxide octahydrate in water. The resulting basic mixture was stirred for 1.5 hr and then filtered through Celite ®. The filtrate was then concentrated to a solid residue which was redissolved in water and stirred with Celite ® while a solution of zinc sulfate hydrate in water was added in portions until no further precipitation occurred. The mixture was filtered. The aqueous zinc salt solution was evaporated to an oil which was mixed with isopropyl alcohol (IPA), water and isopropyl ether and stirred overnight. The light suspension was filtered to give 0.7 g of solid. The filtrate was concentrated and pumped (under reduced pressure) to a white, solid foam. This solid was triturated in isopropyl ether, collected and pumped at room temperature overnight to give 17 g of white solid, mp with decomposition >80° C.

Analysis: Calc'd for $C_{18}H_{26}N_2S_2O_{12}Zn \cdot 2H_2O \cdot \frac{1}{2}IPA$: C, 35.60; H, 5.21; N, 4.26; Zn, 9.90; Found: C, 35.87; H, 5.08; N, 4.87; Zn, 8.64.

EXAMPLE 3

1-[(2-Methoxyphenoxy)methyl]-1,2ethanediol bisulfamate (ester).

a. Preparation of sulfamoyl chloride solution in excess acetonitrile.

To a solution of 13.1 ml (0.15 mole) of chlorosulfonyl isocyanate in 20 ml of acetonitrile with agitation and cooling in an acetone-ice bath was added slowly dropwise a solution of 2.7 ml (0.15 mole) of water in 10 ml (excess) acetonitrile at −5° C. to +5° C. over a 15 min period. Upon addition of each drop, vigorous evolution of carbon dioxide was noted. The solution was stirred in the cold bath for 15 minutes after addition was complete.

b. Preparation of the title compound.

To the above prepared sulfamoyl chloride solution was added 8 g (0.04 mole) of 3-(2-methoxyphenoxy)-1,2-propanediol (which is glyceryl guaiacolate) in a solution of 15.2 ml (0.176 mole) of pyridine in 20 ml of acetonitrile at −3° C. to +15° C. over a 13 min period. The cold bath was removed and the reaction mixture was stirred for 2 hr. Ethyl acetate, 30 ml, was added and the mixture was extracted thrice with saturated sodium chloride solution. The aqueous layers were back extracted twice with a 1:1 vol mixture of ethyl acetate:acetonitrile. The organic layers were combined and dried over sodium sulfate and evaporated to give a glassy residue. Crystallization using isopropyl alcohol and isopropyl ether produced 10.3 g (74.5%) of slightly impure title product in 2 crops. The crystals were triturated with water and a small amount of isopropyl alcohol and then subjected to filtration, dried and dissolved in warm acetonitrile. A small amount of solid was removed by filtration. The filtrate was mixed with water and subjected to slow evaporation. The resulting suspension was filtered and the solid was rinsed with water, isopropyl alcohol and isopropyl ether. The white solid was dried in a vacuum oven at 40° C. overnight, mp 151°–153° C.

Analysis: Calculated for $C_{10}H_{16}N_2O_8S_2$: C, 33.70; H, 4.53; N, 7.86; Found: C, 34.16; H, 4.65; N, 8.20.

EXAMPLE 4

1-[(2-Methoxyphenoxy)methyl]-1,2-ethanediol bis(-methylsulfamate) (ester).

a. Preparation of N-methylsulfamoyl chloride.

A mixture of 16.2 g (0.235 mole) of 98% purity methylamine hydrochloride, 19.4 ml (0.235 mole) of 97% purity sulfuryl chloride and 0.2 ml of anitmony (V) chloride in 70 ml of acetonitrile was heated at reflux for 4 hr. To the reaction mixture was added another 19.4 ml (0.235 mole) of sulfuryl chloride and reflux was continued overnight. The reaction mixture changed from a suspension to a brown solution. The solution was concentrated under reduced pressure and then pumped under vacuum to give 30 g of brown oil. $^1$H NMR analysis showed the oil to be mainly N-methylsulfamoyl chloride.

b. Preparation of title compound.

A solution of 8 g (0.04 mole) of 3-(2-methoxyphenoxy)-1,2-propanediol (which is glyceryl guaiacolate) in 13 ml (0.16 mole) of pyridine and 40 ml of methylene chloride was added in a thin stream to a solution of 20.72 g (ca. 0.16 mole) of the crude N-methylsulfamoyl chloride prepared above in 60 ml of methylene chloride while stirring in a room temperature water bath. After 2 hr stirring, the reaction mixture was extracted twice with water. The organic layer was dried over sodium sulfate, filtered and concentrated to 20.42 g of brown oil. This oil was purified by column chromatography on silica gel column, eluting with 10% ethyl acetate in methylene chloride to give the title compound as a viscous oil.

Analysis: Calculated for $C_{12}H_{20}N_2O_8S_2$: C, 37.49; H, 5.24; N, 7.29; Found: C, 37.07; H, 5.29; N, 7.14.

EXAMPLE 5

1,4:3,6-Dianhydro-D-glucitol disulfamate.

To an agitated solution of ca. 0.30 mole of sulfamoyl chloride in acetonitrile as prepared in Example 3 (twice the amounts shown) was added 14.90 g (0.10 mole) of isosorbide in pyridine and acetonitrile at −3° to 15° C., while cooling in an ice bath. The cold bath was removed and the reaction mixture was stirred. The mixture was extracted with ethyl acetate as in Example 3, the extract washed, dried and evaporated to give about 20 g of brown oil as crude title product. The oil was chromatographed on 400 g silica gel eluting with 15% methanol in methylene chloride. A heart cut of the fractions gave 9.5 g of oil. The oil was subjected to reduced pressure in a vacuum oven at 40° C. overnight.

Analysis: Calculated for $C_6H_{12}N_2O_8S_2$: C, 23.68; H, 3.98; N, 9.21; Found: C, 23.46; H, 4.12; N, 9.07.

EXAMPLE 6

1,3,4,6-Tetrakisoxy-[[[(1-methylethoxy)carbonyl]amino]sulfonyl]β-D-fructofuranosyl-α-D-glucopyranoside tetrakis[[[(1-methylethoxy)carbonyl]amino]-sulfonate hydrate[1:2].

To a solution of 20.2 g (0.1 mole) of isopropyl ester of N-chlorosulfonyl carbamic acid in 50 ml of acetonitrile as prepared in Example 1 was added 3.42 g (0.01 mole) of sucrose. Pyridine (50 ml) was added dropwise in seven minutes to the stirred suspension without heating or cooling. The reaction mixture became quite warm and the sucrose dissolved gradually. After stirring overnight, the clear solution was concentrated to a syrup. The syrup was dissolved in 1:1 acetonitrile and ethyl acetate mixture. The resulting solution was extracted sequentially with water, dilute hydrochloric acid and water, dried over sodium sulfate and evaporated to give 14.61 g of foam. The foam was dissolved in methylene chloride and the solution extracted twice with aqueous sodium bicarbonate solution. The layers were separated and the aqueous layers were combined. This aqueous mixture was back extracted with methylene chloride and the aqueous layer again separated. Fresh methylene chloride was added and the aqueous layer was cooled and acidified with concentrated hydrochloric acid while in contact with the methylene chloride. The layers were separated and the acidified aqueous layer was again extracted with methylene chloride. The methylene chloride layers obtained since acidifying were combined. This methylene chloride solution was back washed with saturated sodium chloride solution, dried over sodium sulfate, filtered and evaporated to give 14.06 g of foamy solid. This solid was dissolved in methylene chloride and isopropyl ether was added. The solution was concentrated to evaporate most of the methylene chloride to give a slight suspension. Additional isopropyl ether was added to give complete precipitation. The solid was collected by filtration, rinsed twice with isopropyl ether, dried under a nitrogen atmosphere and vacuum pumped at room temperature overnight. White solid weighing 5.5 g was obtained, mp≧130° C.

Analysis: Calculated for $C_{44}H_{78}N_8O_{43}S_8 \cdot 2H_2O$: C, 31.10; H, 4.86; N, 6.59; Found: C, 31.33; H, 4.79; N, 6.42.

EXAMPLE 7

2,2-Bis(hydroxymethyl)-1,3-propanediol tetrasulfamate.

a. Preparation of benzyloxycarbonylsulfamoyl chloride.

To a solution of 43.5 ml (0.5 mole) of chlorosulfonyl isocyanate in 400 ml of methylene chloride, stirred in an ice bath, was added 51.6 ml (0.5 mole) of benzyl alcohol over an one hr period. The reaction mixture was concentrated under reduced pressure and the solid residue was triturated in petroleum ether (bp range 35°–65° C.). The solid was collected by filtration, rinsed twice with petroleum ether and dried under vacuum to give 110 g (88% yield) of benzyloxycarbonylsulfamoyl chloride.

b. Preparation of title compound.

To a solution of 25 g (0.1 mole) of the benzyloxycarbonylsulfamoyl chloride prepared above in 50 ml of acetonitrile were added 2.72 g (0.02 mole) of pentaerythritol (solid) and 50 ml pyridine dropwise in 5 min. The mixture was stirred without heating or cooling to give a clear brown solution in ½ hr. After stirring overnight, the solvents were evaporated. The residual oil was dissolved in methylene chloride and extracted twice with dilute hydrochloric acid. The aqueous layers were back extracted with methylene chloride. The organic layers were combined and dried over sodium sulfate, filtered, evaporated and vacuum pumped to a foamy solid weighing 19.94 g. The foamy solid was dissolved in 150 ml tetrahydrofuran (THF) and 50 ml of water. The solution was mixed with 3 g of 5% palladium on carbon catalyst and hydrogenated at room temperature under about 50 psi hydrogen overnight. The catalyst was removed by filtration and the filtrate was concentrated. The residue was triturated in acetonitrile to give 2 g of sticky solid A. The mother liquor was concentrated and triturated in acetonitrile to give 2 g of solid B. The mother liquor of solid B was concentrated and triturated in water and isopropyl ether to give some white solid C. Solid samples A and B were combined and triturated in water and isopropyl ether to give white solid D. Solid samples C and D were combined, dissolved in aqueous THF and the mixture filtered and the filtrate evaporated to give a residue. This residue was triturated with acetonitrile to give 3.5 g solid title compound, mp 200°–202° C.

Analysis: Calculated for $C_5H_{16}N_4O_{12}S_4$: C, 13.27; H, 3.56; N, 12.38; Found: C, 13.59; H, 3.72; N, 12.22.

EXAMPLE 8

3-Phenoxy-1,2-propanediol bissulfamate (ester).

a. Preparation of sulfamoyl chloride in excess acetonitrile.

To a solution of 24.8 g (0.175 mole, 15.2 ml) of chlorosulfonyl isocyanate in 100 ml of acetonitrile cooled in an ice-acetone bath was added dropwise a solution of 32 g (0.175 mole) of water in 10 ml of acetonitrile at such a rate that the temperature did not exceed 7° C. (45 min). The mixture was stirred at −3° C. for 15 min after addition was complete.

b. Preparation of title compound.

To the above sulfamoyl chloride solution in acetonitrile was added dropwise with stirring a solution of 8.4 g (0.05 mole) of 3-phenoxy-1,2-propanediol (95% purity obtained from Aldrich Chem. Co., Inc.) and 20.2 g (0.2 mole) of triethylamine in 50 ml of acetonitrile at such a rate that the temperature did not exceed 12° C. over a 45 min period. The cooling bath was removed and the mixture was stirred for 2 hr and treated with 100 ml of ethyl acetate and 50 ml of water. The mixture was vigorously stirred for 5 min and the layers were separated. The organic layer was washed with 50 ml of water and 100 ml of salt brine, dried over sodium sulfate and concentrated to give a gum as residue. The gum was purified by column chromatography on 350 g of silica gel. Fractions eluted with 15% acetone in methylene chloride were combined and concentrated to give a clear gum as residue. The gum was triturated with petroleum ether (b.p. 30°–60° C.) to give crystalline solid. The solid was collected by filtration and recrystallized from benzene-acetonitrile to yield 4.2 g (26% yield) of white solid title compound, mp 116°–118° C.

Analysis: Calculated for $C_9H_{14}N_2O_7S_2$: C, 33.12; H, 4.32; N, 8.58; Found: C, 33.16; H, 4.36; N, 8.54.

EXAMPLE 9

1,4:3,6-Dianhydro-D-glucitol monosulfamate, mononitrate.

A solution of sulfamoyl chloride (0.15 mole) in acetonitrile (30 ml) was prepared in the same manner as described in Example 3.

Isosorbide mononitrate (obtained as a mixture with 10% lactose, (21.2 g, 0.1 mole) was triturated with acetonitrile (80 ml) and filtered to remove the insoluble lactose. This solution of isosorbide mononitrate was mixed with pyridine 12.1 ml (0.15 mole) and then added to the sulfamoyl chloride solution at −8° to +1° C. over one-half hour. The cold bath was removed and the reaction mixture was stirred overnight. The product was worked up in the same way as in Example 3 to give a solid after evaporation. The solid was mostly dissolved in hot 1:1 acetonitrile/ethyl acetate, filtered to remove small amount of inorganic material, and the filtrate was evaporated to give a 29 g of solid. This solid was triturated overnight in water with trace amount of isopropyl alcohol. The suspension was filtered and rinsed twice with water; air dried to give 20 g solids. Recrystallization from isopropyl alcohol gave 14.6 g white solid. The solid was vacuum pumped overnight at room temperature, mp 133°–134° C.

Analysis: Calc'd for $C_6H_{10}N_2O_8S$: C, 26.67;H, 3.73;N, 10.37: Found: C, 26.89;H, 3.77;N, 10.30.

EXAMPLE 10

2,2-Bis(hydroxymethyl)-1,3-propanediol-tetrakis[(1-methoxyethoxy)carbonylsulfamate (ester) compound with 2-propanol [2:1].

a. Preparation of isopropyl ester of N-chlorosulfonyl carbamic acid in methylene chloride solution.

To 75 ml of methylene chloride stirred in a cold bath was added 16 ml (0.18 mole) of chlorosulfonyl isocyanate, followed by a solution of 13.8 ml (0.18 mole) of 2-propanol in 25 ml of methylene chloride over a 33 min period at −2° to +6° C. The cold bath was removed at the end of the addition and the reaction mixture was stirred for 2 hr.

b. The solution prepared in (a) was cooled in an ice bath and 4.08 g (0.03 mole) of pentaerythritol was added followed by 0.2 mole of pyridine over a four min period at 2° to 17° C. Some pyridine hydrochloride precipitated. About 100 ml of acetonitrile was added to redissolve the salt. The pentaerythritol dissolved gradually in four hours time. After stirring overnight, the reaction mixture was evaporated to dryness. The solid residue was triturated with water, collected thereafter by filtration and rinsed 3 times with water. The wet solid cake was mostly dissolved in hot isopropyl alcohol. The solution was filtered and the filtrate was concentrated to a small volume and allowed to stand to solidify. The solid was triturated with isopropyl ether, recollected by filtration and rinsed with isopropyl ether. The filter cake was subjected to vacuum pumping at room temperature overnight to give 16.64 g of white solid, mp 195°–197° C.

Analysis: Calculated for $C(CH_2OSO_2NHCO_2C_3H_7)_4 \cdot 0.5C_3H_8O$: C,32.68;H, 5.36;N, 6.78: Found: C, 32.34;H, 5.35;N, 6.86.

EXAMPLE 11

2,2-Bis(hydroxymethyl)-1,3-propanediol-tetrakis[(1-methyethoxy)carbonylsulfamate (ester) zinc complex hydrate [2:7] compound with 2-propanol[2:1].

The compound obtained in Example 10, i.e. 2,2-bis(hydroxymethyl)-1,3-propanediol-tetrakis[(1-methoxyethoxy)carbonylsulfamate (ester) compound with 2-propanol [2:1], was dissolved in methanol and treated with barium hydroxide octahydrate followed by zinc sulfate hydrate in the same manner as Example 2. The aqueous solution of the zinc salt was evaporated to give white solid which was recrystallized from water-isopropyl alcohol (IPA) combination. The solid was rinsed with IPA and isopropyl ether, and dried at 50° C. under vacuum to give 14.6 g of title salt, mp with decomposition, >210° C.

Analysis: Calculated for $C_{21}H_{36}N_4O_{20}S_4Zn_2 \cdot 3.5H_2O \cdot 0.5IPA$: C, 26.58; H, 4.66;N, 5.51;Zn, 12.86: Found: C, 26.98;H, 4.89;N, 5.40;Zn, 11.70.

EXAMPLE 12

2-Phenoxyethanol sulfamate (ester).

a. Preparation of sulfamoyl chloride solution in excess acetonitrile.

To a stirred, cooled (ice-acetone bath) solution of 48.8 g (30.4 ml, 0.342 mole) of chlorosulfonyl isocyanate of 98% purity (Aldrich Chemical Co.) in 150 ml of acetonitrile was added dropwise a solution of 6.4 g (0.356 mole) of water in 20 ml of acetonitrile at such a rate that the temperature did not exceed 7° C. Addition time was 40 min. After the addition was completed, the mixture was stirred at $-3°$ C. for 15 min.

b. Preparation of title compound.

To the solution prepared in (a) was added dropwise a solution of 13.8 g (0.1 mole) of 2-phenoxyethanol and 40.4 g (0.4 mole) of triethylamine in 100 ml of additional acetonitrile at such a rate that the temperature did not exceed 12° C. Addition time was 45 min. The cold bath was removed and the mixture was stirred for 2 hr and then treated with 200 ml of ethyl acetate and 100 ml of water. The mixture was vigorously stirred for 5 min and the layers were separated. The organic layer was washed twice with 100 ml of water, twice with 100 ml portions of saturated sodium chloride solution, dried over sodium sulfate and subjected to reduced pressure to remove volatiles to give a viscous, oily residue which solidified on standing. The solid was dissolved in 300 ml of methylene chloride and the solution filtered through Celite ®. The filtrate was concentrated to 200 ml volume and again filtered through Celite ®. The filtrate was concentrated further under reduced pressure to give a solid residue. The residue was recrystallized successively from methylene chloride and ethyl acetate-water mixture to give 10.5 g (48% yield) of title compound as white solid, mp 89°–91° C.

Analysis: Calculated for $C_8H_{11}NO_4S$: C, 44.23;H, 5.10;N, 6.45: Found: C, 43.19;H, 5.08;N, 6.84.

EXAMPLE 13

Benzeneethanol sulfamate (ester).

a. Sulfamoyl chloride solution was prepared as in Example 12 using: 48 g (0.35 mole) of chlorosulfonyl isocyanate (98%), 6.4 g (0.35 mole) of water and 170 ml of acetonitrile.

b. The title compound was obtained using the following procedure: The sulfamoyl chloride in acetonitrile solution prepared in (a) was reacted as in Example 12 with 12.2 g (0.1 mole) of β-phenethyl alcohol using 40.4 g (0.4 mole) triethylamine in 100 ml additional acetonitrile followed by using extracting, washing and concentration procedures of Example 12 through the first evaporation. The crude oily residue was purified by chromatography (10×80 cm glass column; 700 g silica gel; eluents methylene chloride followed by 10:1 methylene chloride/acetone). Fractions containing the title compound were combined and solvents evaporated under reduced pressure to give 13.6 g (68% yield) of title compound as light-yellow oil.

Analysis: Calculated for $C_8H_{11}NO_3S$: C, 47.75;H, 5.51;N, 6.96: Found: C, 47.48;H, 5.53;N, 6.92.

EXAMPLE 14

1,7-Heptanediol bissulfamate (ester).

a. Sulfamoyl chloride solution was prepared as in Example 12 using: 37.9 g (0.262 mole) of chlorosulfonyl isocyanate (98%), 47.0 g (0.261 mole) of water and 170 ml of acetonitrile.

b. The title compound was obtained using the following procedure: The sulfamoyl chloride in acetonitrile solution prepared in (a) was reacted as in Example 12 with 10.5 g (0.0755 mole) of 1,7-heptanediol (95%), 30.3 g (0.300 mole) of triethylamine in 100 ml additional acetonitrile followed by using extracting, washing and concentration procedures of Example 12 through the first evaporation. The viscous residue which solidified on standing was purified by high pressure liquid chromatography using the Waters Associates ® Prep LC/System 500A with Prep Pak 500 ® silica. Eluting solvent used was 10:1 mixture methylene chloride-acetone at a flow rate of 200 ml/min. Fractions containing the title compound were combined and the solvents were evaporated under reduced pressure to give a viscous oil which solidified on standing. The solid was recrystallized from wet methylene chloride to give 8.2 g (37% yield) of title compound as white solid, mp 88.5°–90.5° C.

Analysis: Calculated for $C_7H_{18}N_2O_6S_2$: C, 28.96;H, 6.25;N, 9.65: Found: C, 29.10;H, 6.38;N, 9.69.

EXAMPLE 15

3-Phenoxy-1-propanol sulfamate (ester).

a. Sulfamoyl chloride solution was prepared as in Example 12 using: 31.5 ml (0.356 mole) of chlorosulfonyl isocyanate (98%), 6.3 ml (0.35 mole) of water and 150 ml of acetonitrile.

b. The title compound was obtained using the following procedure: The sulfamoyl chloride in acetonitrile solution prepared in (a) was reacted as in Example 12 with 15.6 g (0.102 mole) of 3-phenoxy-1-propanol using 40.2 g (0.398 mole) of triethylamine in 100 ml additional acetonitrile followed by using, extracting, washing and concentration procedures of Example 12 through the first evaporation. The residue was then purified by chromatography (4×90 cm glass column; 500 g silica gel; methylene chloride followed by 10:1 methylene chloride acetone). Fractions containing the title compound were combined and the solvents were evaporated under reduced pressure to give 15.8 g of viscous oil which solidified on standing. The solid was recrystallized from ethyl acetate to give 14.7 g (62% yield) of title compound as white solid, mp 83°–85° C.

Analysis: Calculated for $C_9H_{13}NO_4S$: C, 46.74;H, 5.67;N, 6.06: Found: C, 46.80;H, 5.73;N, 6.05.

EXAMPLE 16

β-Chlorobenzeneethanol sulfamate (ester).

This compound was isolated during purification in the preparation of 2-phenylethanediol bissulfamate ester.

a. Sulfamoyl chloride solution was prepared as in Example 12 using: 62 ml (0.71 mole) of chlorosulfonyl isocyanate (98%), 12.4 g (0.69 mole) of water and 340 ml of acetonitrile.

b. The title compound was obtained as by-product using the following procedure: The sulfamoyl chloride in acetonitrile solution prepared in (a) was reacted as in Example 12 with 28.4 g (0.2 mole) of 2-phenylethanediol using 80.2 g (0.79 mole) of triethylamine in 200 ml of additional acetonitrile followed by using extracting, washing and concentration procedures of Example 12 through the first evaporation. The oil was purified by chromatography (4×90 cm glass column; 500 g silica gel; eluting agents: methylene chloride followed by 10:1 methylene chloride-acetone). Fractions containing the title compound were combined and the solvents were evaporated under reduced pressure to give 5.1 g of viscous oil. The oil was further purified by high pressure liquid chromatography using the Waters Associates Prep LC/System 500A with Prep Pak 500 ® silica. Eluting solvent was methylene chloride at a flow rate of 200 ml/min. Fractions containing the title compound were combined and the solvent was evaporated under reduced pressure to give 3.6 g (8%) of title compound as a colorless, viscous oil.

Analysis: Calculated for $C_8H_{10}ClNO_3S$: C, 40.77;H, 4.28;N, 5.94: Found: C, 40.59;H, 4.27;N, 5.96.

EXAMPLE 17

Benzenebutanol sulfamate (ester).

a. Sulfamoyl chloride solution was prepared as in Example 12 using 36.4 ml (0.418 mole) of chlorosulfonyl isocyanate (98%), 7.3 g of water, and 150 ml of acetonitrile.

b. The title compound was obtained using the following procedure: The sulfamoyl chloride in acetonitrile solution prepared in (a) was reacted as in Example 12 with 17.7 g (0.118 mole) of 4-phenylbutanol, 46.4 g (0.459 mole) of triethylamine in 100 ml additional acetonitrile followed by using extracting, washing and concentration procedures of Example 12 through the first evaporation. The viscous residue was purified by high pressure liquid chromatography (Waters Associates Prep LC/System 500A Prep Pak 500 ® silica. Eluting solvent used was methylene chloride at a flow rate of 200 ml/min). Fractions containing the title compound were combined and the solvent was evaporated under reduced pressure to give 19.3 g of colorless, viscous oil which solidified on standing. The solid was recrystallized from ethyl ether-petroleum ether (bp range 30°–60° C.) to give 16.9 g (63%) of title compound as white solid, mp 79°–81° C.

Analysis: Calculated for $C_{10}H_{15}NO_3S$: C, 52.38;H, 6.59;N, 6.11: Found: C, 52.53;H, 6.67;N, 6.09.

EXAMPLE 18

1,4:3,6-Dianhydro-d-mannitol disulfamate (ester).

a. Sulfamoyl chloride solution was prepared as in Example 12 using 42.6 g (0.30 mole) of chlorosulfonyl isocyanate, 5.4 ml (0.30 mole) of water and 60 ml of acetonitrile, 0°–10° C. during reaction.

b. The title compound was obtained using the following procedure: The sulfamoyl chloride prepared in (a) was reacted with 14.6 g (0.10 mole) of isomannide using 28.5 ml (0.352 mole) of pyridine in 40 ml of acetonitrile at 0°–5° C. followed by 2 hr at room temperature. Ethyl acetate, 60 ml, was added to the mixture which was then extracted with three 100 ml portions of saturated sodium chloride solution. These brine washes were combined and back extracted with ethyl acetate/acetonitrile mixture. The organic layers were combined, dried over magnesium sulfate, filtered and evaporated. The oily crystalline residue was recrystallized from acetonitrile and isopropyl alcohol (IPA) with removal of IPA on a rotary evaporator. Crystals were filtered, dried and analyzed.

Analysis: Calculated for $C_6H_{12}N_2O_8S_2$: C, 23.68;H, 3.98;N, 9.21: Found: C, 24.12;H, 4.09;N, 9.03.

EXAMPLE 19

2-Phenoxy-1,3-propanediol disulfamate (ester).

a. Sulfamoyl chloride solution was prepared as in Example 12 using: 32 ml (0.368 mole) of chlorosulfonyl isocyanate (98%), 6.4 ml (0.356 mole) of water and 150 ml of acetonitrile.

b. The title compound was obtained using the following procedure: The sulfamoyl chloride prepared in (a) was reacted as in Example 12 with 17.3 g (0.103 mole) of 2-phenoxy-1,3-propanediol using 41.4 g (0.41 mole) of triethylamine in 100 ml of additional acetonitrile followed by using extracting, washing and concentration procedures of Example 12 through the first evaporation. The oily residue was purified by chromatography as in Example 13 and fractions containing the title compound were combined and concentrated to give a solid residue. The residue was recrystallized using ethyl ether and petroleum ether (bp 30°–60° C.) to give 7.5 g (22%) of white solid title compound, mp 104°–106° C.

Analysis: Calculated for $C_9H_{14}N_2O_7S_2$: C, 33.12; H, 4.32; N, 8.58; Found: C, 33.27; H, 4.36; N, 8.48.

EXAMPLE 20

Cyclohexanol sulfamate (ester).

a. Preparation of sulfamoyl chloride solution in excess acetonitrile.

To 40 ml of acetonitrile cooled to −10° C. in an acetone/ice bath was added 26.2 ml (0.30 mole) of chlorosulfonyl isocyanate dropwise while maintaining temperature at −10° C. To this solution was added a solution of 5.4 ml (0.30 mole) of water in 20 ml of acetonitrile over a 30 min period maintaining temperature below 0° C.

b. Preparation of title compound.

To the cold solution prepared in (a) was slowly added a solution of 20.03 g (0.20 mole) of cyclohexanol in 28.5 ml (0.352 mole) of pyridine and 20 ml of acetonitrile and the reaction mixture was allowed to warm slowly to room temperature. After stirring at room temperature overnight, the organic layer was extracted with three 100 ml portions of saturated sodium chloride solution and the aqueous layer was back extracted with 1:1 acetonitrile/ethyl acetate mixture. The organic layers were combined, dried over sodium sulfate and evaporated to give an oil residue. The oil was purified by column chromatography as in Example 13 and a heart cut taken and evaporated. The residue was subjected to vacuum pumping overnight to give 9.6 g (27% yield) of title compound.

Analysis: Calculated for $C_6H_{13}NO_3S$: C, 40.21; H, 7.31; N, 7.82; Found: C, 39.65; H, 7.38; N, 7.74.

EXAMPLE 21

α-[(Aminosulfonyl)oxy]benzeneacetic acid, ethyl ester.

The procedure used was identical to that of Example 20, except 36.04 g (0.20 mole) of ethyl-dl-mandelate was substituted for cyclohexanol. The residue from evaporation of the chromatography cut was recrystallized from isopropyl alcohol and petroleum ether (30-60 bp range) to yield 9.65 g (19%) of crystals, mp 91°-93° C.

Analysis: Calculated for $C_{10}H_{13}NO_5S$: C, 46.33; H, 5.05; N, 5.40; Found: C, 46.25; H, 5.01; N, 5.36.

EXAMPLE 22

3-(2-Methoxyphenoxy)-1,2-propanediol dimethylsulfamate (ester).

a. Preparation of dimethyl sulfamoyl chloride.

A mixture of 28.8 g (0.353 mole) of dimethylamine hydrochloride (98%, Aldrich Chemical Co.), 29.1 ml (0.362 mole) of sulfuryl chloride (97%, Aldrich) and 0.3 ml of antimony (V) pentachloride (Baker Chemical Co.) in 100 ml of acetonitrile was stirred and heated at reflux for 4 hr. An additional 29.1 ml (0.362 mole) of sulfuryl chloride was added and the mixture was heated at reflux overnight. The mixture was concentrated under reduced pressure to give 44.2 g (87%) of dimethyl sulfamoyl chloride as a brown liquid.

b. Preparation of title compound.

To a stirred solution of 21.9 g (152.5 mole) of the dimethylsulfamoyl chloride prepared in (a) above in 60 ml of methylene chloride was added a solution of 7.6 g (0.038 mole) of 3-(2-methoxyphenoxy)-1,2-propanediol (which is glyceryl guaiacolate) and 12.1 g (0.152 mole) of pyridine in 40 ml of methylene chloride at such a rate that the reaction temperature was maintained at ≧12° C. The reaction mixture was stirred at ambient temperature for 4 days. Water, 200 ml, was added to the mixture and the layers were separated. The organic layer was washed successively with two 200 ml portions of 2N hydrochloric acid and 200 ml of water, dried over magnesium sulfate and the solvent was evaporated under reduced pressure to give 11.6 g of yellow liquid. The liquid was purified by high pressure chromatography using a Waters Associates Prep LC/System 500A with Prep Pak 500 ® silica. Eluting solvent used was 10:1 mixture of methylene chloride to ethyl acetate at a flow rate of 200 ml/min). Fractions containing the title compound were combined and the solvents were evaporated under reduced pressure to give 3.9 g (33%) of title compound as a yellow, viscous oil.

Analysis: Calculated for $C_{12}H_{19}NO_6S$: C, 47.20; H, 6.27; N, 4.59; Found: C, 47.73; H, 6.14; N, 4.30.

Analysis: Calculated for $C_{12}H_{19}NO_6S \cdot 0.05CH_3CO_2CH_2CH_3$: C, 47.31; H, 6.31; N, 4.56.

EXAMPLE 23

3-(2-Methoxyphenoxy)-1,2-propanediol-1-carbamate-2-sulfamate (ester).

a. Sulfamoyl chloride solution was prepared as in Example 12 using: 30.4 ml (0.342 mole) of chlorosulfonyl isocyanate (98%), 6.4 g (0.356 mole) of water and 150 ml of acetonitrile.

b. The title compound was obtained using the following procedure: The sulfamoyl chloride in acetonitrile solution prepared in (a) was reacted as in Example 12 with 24.1 g (0.1 mole) of 3-(2-methoxyphenoxy)-1,2-propanediol-1-carbamate, which is methocarbamol, using 40.4 g (0.4 mole) of triethylamine in 100 ml additional acetonitrile followed by using extracting, washing and concentration procedures of Example 12 through the first evaporation. The viscous, oily residue 29.1 g was purified by chromatography using a 4.5 cm×100 cm glass column filled with 550 g silica gel and 10:1 ratio of methylene chloride/acetone as eluting agent. Fractions containing the title compound were combined and the solvents were evaporated under reduced pressure to give 12.6 g of a white solid. The solid was recrystallized from acetone-benzene to give 10.0 g (31%) of title compound as white solid, mp 119°-122° C.

Analysis: Calculated for $C_{11}H_{16}N_2O_7S$: C, 41.25; H, 5.04; N, 8.75; Found: C, 41.13; H, 5.07; N, 8.71.

EXAMPLE 24

1,3-Diphenoxy-2-propanol sulfamate (ester).

a. Sulfamoyl chloride solution was prepared as in Example 12 using: 18.8 ml (0.212 mole) of chlorosulfonyl isocyanate (98%), 3.9 g (0.217 mole) of water and 150 ml of acetonitrile.

b. The title compound was obtained using the following procedure: The sulfamoyl chloride prepared in (a) was reacted as in Example 12 with 15.0 g (0.061 mole) of 1,3-diphenoxy-2-propanol (Aldrich Chem. Co.) using 24.8 g (0.246 mole) of triethylamine in 100 ml of additional acetonitrile followed by using extracting, washing and concentration procedures through the first evaporation. The 20.4 g semisolid residue obtained was dissolved in 100 ml of methylene chloride and the solution was filtered through 50 g of silica gel. The silica gel was washed with 600 ml of methylene chloride. The combined methylene chloride solutions were evaporated under reduced pressure and the viscous residue was purified by high pressure liquid chromatography (Waters Associates Prep LC/System 500A; Prep Pak ® 500 silica using methylene chloride eluting agent at a flow rate of 200 ml/min). Fractions containing the title compound were combined and solvents were evaporated under reduced pressure to give 12.9 g (65%) of title compound as white solid, mp 81°-84° C.

Analysis: Calculated for $C_{15}H_{17}NO_5S$: C, 55.72; H, 5.30; N, 4.33; Found: C, 55.58; H, 5.27; N, 4.28.

EXAMPLE 25

3-(4-Chlorophenoxy)-1,2-propanediol disulfamate ester.

a. Sulfamoyl chloride solution was prepared as in Example 12 using 50.5 ml (0.592 mole) of chlorosulfonyl isocyanate (98%), 10.9 g (0.606 mole) of water and 150 ml of acetonitrile.

b. The title compound was obtained using the following procedure: The sulfamoyl chloride in solution prepared in (a) was reacted as an Example 12 with 15.0 g (0.074 mole) of 3-(4-chlorophenoxy)-1,2-propanediol using 69.9 g (0.692 mole) of triethylamine in 100 ml of additional acetonitrile followed by using extracting, washing and concentration procedures of Example 12 through the first evaporation. The viscous, oily residue obtained was purified by high pressure liquid chromatography (Waters Associates Prep LC/System 500A; Prep Pak 500 ® silica; 9:1 methylene chloride-acetone at a flow rate of 200 ml/min). Fractions containing the title compound were combined and the solvents were evaporated under reduced pressure to give 10.2 g of viscous oil. The oil was partitioned between water and ethyl ether (300 ml each). The ether layer was separated and washed with three 200 ml portions of water, dried over sodium sulfate and solvent evaporated under reduced pressure to give 8.9 g (33%) of viscous oil which solidified on standing, mp 101°-104° C.

Analysis: Calculated for $C_9H_{13}ClN_2O_7S_2$: C, 29.96; H, 3.63; N, 7.76; Found: C, 30.36, H, 3.71; N, 7.75.

EXAMPLE 26

Benzenepropanol sulfamate (ester).

a. Sulfamoyl chloride solution was prepared as in Example 12 using 36.4 ml (0.410 mole) of chlorosulfonyl isocyanate (98%), 7.3 g (0.406 mole) of water, and 150 ml of acetonitrile.

b. The title compound was obtained using the following procedure: The sulfamoyl chloride in solution prepared in (a) was reacted as in Example 12 with 16.4 g (0.118 mole) of 3-phenyl-1-propanol (98%) using 46.4 g (0.459 mole) of triethylamine in 100 ml of additional acetonitrile followed by using the extracting, washing and concentration procedures of Example 12 through the first evaporation. The viscous, oily residue was partitioned between water and ethyl ether (300 ml each). The organic layer was separated and washed with four 200 ml portions of water, the aqueous wash being finally neutral to pH paper. The organic layer was dried over magnesium sulfate and the solvent was evaporated under reduced pressure to give 19.5 g of a light-yellow, viscous oil which solidified on standing. The solid was recrystallized using ethyl ether and petroleum ether (bp range 30°-60° C.) to give 12.1 g (48%) of title compound as white solid, mp 56.5°-58° C.

Analysis: Calculated for $C_9H_{13}NO_3S$: C, 50.22; H, 6.09; N, 6.51; Found: C, 50.30; H, 6.16; N, 6.55.

EXAMPLE 27

2-(2-Chlorophenoxy)ethanol sulfamate (ester).

a. Sulfamyl chloride solution was prepared as in Example 12 using 30.4 ml (0.342 mole) of chlorosulfonyl isocyanate (98%), 6.4 g (0.356 mole) of water and 150 ml of acetonitrile.

b. The title compound was obtained using the following procedure: The sulfamoyl chloride in solution prepared in (a) was reacted as in Example 12 with 17.3 g (0.100 mole) of 2-chlorophenoxyethanol using 40.4 g (0.400 mole) of triethylamine in 100 ml of acetonitrile followed by using the extracting, washing and concentration procedures of Example 12 through the first evaporation. The viscous, oily residue was partitioned between 500 ml of water and 500 ml of ethyl ether. The organic layer was washed with four 300 ml portions of water (pH of wash finally neutral to pH paper), dried over magnesium sulfate and the solvent evaporated under reduced pressure to give a white solid. The solid was recrystallized from ethyl ether-petroleum ether (bp range 30°-60° C.) to give 14.5 g (58%) of title compound as white solid, mp 84.5°-86° C.

Analysis: Calculated for $C_8H_{10}ClNO_4S$: C, 38.18; H, 4.01; N, 4.57; Found: C, 38.24; H, 4.03; N, 4.59.

EXAMPLE 28

2-(4-Chlorophenoxy)ethanol sulfamate ester.

The title compound was prepared by procedures of Example 27 from sulfamoyl chloride and 2-(4-chlorophenoxy)ethanol in 48% yield. A white solid, mp 117°-119° C. was obtained.

Analysis: Calculated for $C_8H_{10}ClNO_4S$: C, 38.18; H, 4.01; N, 5.57; Found: C, 38.38; H, 4.06; N, 5.66.

EXAMPLE 29

2-(3-Methylphenoxy)ethanol.

The title compound was prepared by procedures of Example 27 from sulfamoyl chloride and 2-(3-methylphenoxy)ethanol in 47% yield (recrystallizing from the same solvent). A white solid, mp 76°-78° C., was obtained.

Analysis: Calculated for $C_9H_{13}NO_4S$: C, 46.74; H, 5.67; N, 6.06; Found: C, 46.79; H, 5.74; N, 6.13.

EXAMPLE 30

3-Phenoxy-2-propanol sulfamate ester.

The title compound was prepared by procedures of Example 27 from sulfamoyl chloride and 3-phenoxy-2-propanol through the partitioning and final evaporation to give an oil as residue. The oil was purified by chromatography using a 4.5 cm×100 cm glass column packed with 500 g of silica gel and methylene chloride as eluting agent. Fractions containing the title compound were combined and the solvent was evaporated under reduced pressure to give a 37% yield of an oil which solidified on standing, mp 57°-60° C.

Analysis: Calculated for $C_9H_{13}NO_4S$: C, 46.74; H, 5.67; N, 6.06; Found: C, 46.85; H, 5.73; N, 6.02.

EXAMPLE 31

2-(2-Pyridinyl)ethanol sulfamate (ester).

a. Sulfamoyl chloride solution was prepared as in Example 12 using 43 ml (0.484 mole) of chlorosulfonyl isocyanate (98%), 8.6 g (0.478 mole) of water and 150 ml of methylene chloride.

b. The title compound was obtained using the following procedure: The sulfamoyl chloride solution prepared in (a) was reacted as in Example 12 with 16.7 g (0.136 mole) of 2-(β-hydroxyethyl)pyridine using 54.9 g (0.544 mole) of triethylamine in 100 ml of methylene chloride. Water, 150 ml, was added to the reaction mixture with agitation and the layers was separated. The organic layer was discarded, pH of the aqueous layer was adjusted to 8 with sodium carbonate. The mixture was extracted with three 200 ml portions of methylene chloride. The organic extracts were washed twice with 200 ml portions of water, dried over magnesium sulfate and the solvent was evaporated under reduced pressure to give 7.1 g of a brown, viscous oil which solidified on standing. The solid was recrystallized from methylene chloride-petroleum ether (bp range 30°-60° C.) to give 3.2 g (12%) of title compound as white needles, mp 89°-91° C.

Analysis: Calculated for $C_7H_{10}N_2O_3S$: C, 41.58; H, 4.98; N, 13.85; Found: C, 41.30; H, 5.00; N, 13.75.

EXAMPLE 32

2-(3-Methoxyphenoxy)ethanol sulfamate (ester).

The title compound was prepared by procedures of Example 12 from sulfamoyl chloride and 2-(3-methoxyphenoxy)ethanol through the first evaporation step to give a brown, viscous, oily residue. The oil was dissolved in 300 ml of ethyl ether. The organic solution was washed with two 300 ml portions of water, dried over magnesium sulfate and the solvent evaporated under reduced pressure to give a viscous, oily residue for the second time. The oil was purified by chromatography using silica gel and methylene chlorideacetone in 90:1 ratio as eluting agent. Fractions containing the title compound were combined and solvents evaporated under reduced pressure to give a viscous oil which solidified on standing. The solid was recrystallized from ethyl-petroleum ether (bp range 30°-60° C.) to give the title compound as white solid, mp 78°-82° C., in 46% yield.

Analysis: Calculated for $C_9H_{13}NO_5$: C, 43.72; H, 5.30; N, 5.66; Found: C, 43.77; H, 5.33; N, 5.67.

EXAMPLE 33

2-(4-Methylphenoxy)ethanol sulfamate (ester).

a. Sulfamoyl chloride solution was prepared as in Example 12 using 40 ml (0.450 mole) of chlorosulfonyl isocyanate, 8.0 g (0.444 mole) of water and 150 ml of acetonitrile.

b. The title compound was obtained using the following procedure: The sulfamoyl chloride in acetonitrile solution prepared in (a), 17.0 g (0.112 mole) of 4-methylphenoxyethanol, 51.0 g (0.505 mole) of triethylamine in 100 ml of acetonitrile were reacted as in Example 12 followed by using extracting, washing and concentration procedures of that example through the first evaporation step. The viscous oil obtained was partitioned between water and ethyl ether (400 ml each). The layers were separated and the organic layer was washed with four 300 ml portions of water (pH neutral to pH paper), dried over magnesium sulfate and the solvent was evaporated under reduced pressure to give a solid residue. The solid was recrystallized from ethyl ether-petroleum ether (bp range 30°-60° C.) to give 15.6 g (60%) of title compound as an off-white solid, m.p. 108.5°-110° C.

Analysis: Calculated for $C_9H_{13}NO_4S$: C, 46.74; H, 5.67; N, 6.06; Found: C, 47.06; H, 5.76; N, 6.12.

EXAMPLE 34

2-(2-Methylphenoxy)ethanol sulfamate (ester).

The title compound was prepared by procedures of Example 33 from sulfamoyl chloride and 2-(2-methylphenoxy)ethanol in 53% yield as an off-white solid, mp 81.5°-83° C.

Analysis: Calculated for $C_9H_{13}NO_4S$: C, 46.74; H, 5.67; N, 6.06; Found: C, 46.91; H, 5.75; N, 6.32.

EXAMPLE 35

3-Phenoxy-1-butanol sulfamate (ester).

The title compound was prepared by procedures of Example 33 from sulfamoyl chloride and 4-phenoxy-1-butanol in 54% yield as an off-white solid, mp 76°-77° C.

Analysis: Calculated for $C_{10}H_{15}NO_4S$: C, 48.97; H, 6.16; N, 5.71; Found: C, 49.08; H, 6.26; N, 5.79.

EXAMPLE 36

2-(4-Methoxyphenoxy)ethanol sulfamate (ester).

The title compound was prepared by procedures of Example 33 from sulfamoyl chloride and 2-(4-methoxyphenoxy)ethanol in 54% yield as an off-white solid, mp 84°-87° C.

Analysis: Calculated for $C_9H_{13}NO_5S$: C, 43.72; H, 5.30; N, 5.66; Found: C, 44.20; H, 5.38; N, 5.70.

EXAMPLE 37

2-(Benzyloxy)ethanol sulfamate (ester).

The title compound was prepared by procedures of Example 33 from sulfamoyl chloride and 2-(benzyloxy)ethanol except the oil obtained was then further purified by high pressure chromatography as described in earlier examples using methylene chloride as eluting agent. Fractions containing the title compound were combined and the solvent was evaporated under reduced pressure to give title compound in 54% yield as light-yellow, viscous oil.

Analysis: Calculated for $C_9H_{13}NO_4S$: C, 46.74; H, 5.67; N, 6.06; Found: C, 46.48; H, 5.74; N, 6.03.

EXAMPLE 38

Benzenepentanol sulfamate (ester).

The title compound was prepared by procedures of Example 33 from sulfamoyl chloride and 5-phenyl-1-pentanol. The oil obtained was further purified by chromatography using a column with methylene chloride as eluting agent. Evaporation of appropriate fractions gave a viscous oil which solidified on standing. The solid was recrystallized from ethyl ether-petroleum ether (bp range 30°-60° C.) to give the title compound as white solid, mp 63°-66° C. in 60% yield.

Analysis: Calculated for $C_{11}H_{17}NO_3S$: C, 54.30; H, 7.04; N, 5.76; Found: C, 54.43; H, 7.10; N, 5.73.

EXAMPLE 39

Sulfamic acid phenyl ester.

The compound was prepared by procedures of Example 33 from sulfamoyl chloride and phenol in 30% yield as white solid, mp 81°-85° C.

Analysis: Calculated for $C_6H_7NO_3S$: C, 41.61; H, 4.07; N, 8.09; Found: C, 41.63; H, 4.09; N, 8.07.

EXAMPLE 40

2-[4-(2-Methylpropyl)phenyl]-propan-1-ol-sulfamate (ester).

The title compound was prepared by procedures of Example 33 from sulfamoyl chloride and 2-[4-(2-methylpropyl)phenyl]-propan-1-ol. The oil obtained was further purified as in Example 38 to give the title compound as a white solid, mp 61°-63° C. in 45% yield.

Analysis: Calculated for $C_{13}H_{21}NO_3S$: C, 57.54; H, 7.80; N, 5.16; Found: C, 57.65; H, 7.97; N, 5.11.

EXAMPLE 41

2-(6-Methoxy-2-naphthyl)propanol sulfamate (ester).

The title compound was prepared by the procedure of Example 33 from sulfamoyl chloride and 2-(6-methoxy-2-naphthyl)propanol as white solid, mp 112°-115° C., in 21% yield.

Analysis: Calculated for $C_{14}H_{17}NO_4S$: C, 56.93; H, 5.80; N, 4.74; Found: C, 56.98; H, 5.88; N, 4.85.

EXAMPLE 42

2-(2-Methoxyphenoxy)ethanol sulfamate (ester).

The title compound was prepared by the procedure of Example 33 from sulfamoyl chloride and 2-(2-methoxyphenoxy)ethanol. The solid obtained was dissolved in 150 ml of methylene chloride, and the solution was treated with charcoal and filtered through Celite ®. The filtrate was evaporated under reduced pressure and the solid residue was recrystallized from methylene chloride-petroleum ether (bp range 30°-60° C.) to give the title compound in 25% yield as white solid, mp 102°–104° C.

Analysis: Calculated for $C_9H_{13}NO_5S$: C, 43.72; H, 5.30; N, 5.66; Found: C, 43.72; H, 5.34; N, 5.63.

EXAMPLE 43

2-Phenoxypropanol sulfamate (ester).

The title compound was prepared by procedures of Example 33 from sulfamoyl chloride and 2-phenoxypropanol. The oil obtained was further purified as in Example 38 by chromatography and recrystallization to give the title compound as colorless, viscous oil in 35% yield.

Analysis: Calculated for $C_{19}H_{13}NO_4S$: C, 46.74; H, 5.67; N, 6.06; Found: C, 46.70; H, 5.73; N, 6.02.

EXAMPLE 44

2-(4-Chlorophenoxy)-2-methylpropanol sulfamate (ester).

The title compound was prepared by procedures of Example 33 from sulfamoyl chloride and 2-(4-chlorophenoxy)-2-methylpropanol to give white solid, mp 76°–79° C., in 58% yield.

Analysis: Calculated for $C_{10}H_{14}ClNO_4S$: C, 42.94; H, 5.04; N, 5.01; Found: C, 42.99; H, 5.13; N, 5.12.

EXAMPLE 45

2-(3-Chlorophenoxy)ethanol sulfamate (ester).

The title compound was prepared by procedures of Example 33 from sulfamoyl chloride and 2-(3-chlorophenoxy)ethanol. The oil obtained was further purified by chromatography and recrystallization as in Example 38 to give white solid, mp 66°–69° C., in 44% yield.

Analysis: Calculated for $C_8H_{10}ClNO_4S$: C, 38.18; H, 4.01; N, 5.57; Found: C, 38.25; H, 4.03; N, 5.61.

EXAMPLE 46

2-(4-Bromophenoxy)ethanol sulfamate (ester).

The title compound was prepared by the procedures of Example 33 from sulfamoyl chloride and 2-(4-bromophenoxy)ethanol as white solid, mp 134°–137° C., in 69% yield.

Analysis: Calculated for $C_8H_{10}BrNO_4S$: C, 32.45; H, 3.40; N, 4.73; Found: C, 32.71; H, 3.47; N, 4.71.

EXAMPLE 47

2-(2,4-Dichlorophenoxy)ethanol sulfamate (ester).

The title compound was prepared by the procedures of Example 33 from sulfamoyl chloride and 2-(2,4-dichlorophenoxy)ethanol. The viscous oil obtained solidified and was recrystallized from isopropyl ether to give the solid title compound, mp 75°–77° C., in 35% yield.

An additional 6.9 g of title compound was recovered from the mother liquor to bring the total yield to 60%.

Analysis: Calculated for $C_8H_9Cl_2NO_4S$: C, 33.58; H, 3.17; N, 4.90; Found: C, 33.65; H, 3.16; N, 5.00.

EXAMPLE 48

Benzenemethanol sulfamate (ester).

The title compound was prepared by the procedures of Example 33 from sulfamoyl chloride and benzyl alcohol being careful to use reduced pressure at about 35° C. to remove solvents in order to avoid violent decomposition observed in another trial at higher temperature. A white solid, mp 75°–78° C., was obtained in 38% yield.

Analysis: Calculated for $C_7H_9NO_3S$: C, 44.91; H, 4.85; N, 7.48; Found: C, 45.06; H, 4.88; N, 7.56.

EXAMPLE 49

2-(3,4-Dichlorophenoxy)ethanol sulfamate (ester).

The title compound was prepared by the procedures of Example 33 from sulfamoyl chloride and to 2-(3,4-dichlorophenoxy)ethanol. The tan colored solid obtained was dissolved in isopropyl ether and the solution treated with charcoal and filtered through Celite ®. The filtrate was evaporated under reduced pressure and the solid residue was recrystallized from isopropyl ether to give the title compound, mp 84°–85° C., in 19% yield.

Analysis: Calculated for $C_8H_9Cl_2NO_4S$: C, 33.58; H, 3.17; N, 4.90; Found: C, 33.76; H, 3.19; N, 4.92.

EXAMPLE 50

2-[(Aminosulfonyl)oxy]benzoic acid.

a. Preparation of benzyloxycarbonylsulfamoyl chloride.

The procedure of Example 7 was followed scaling the reaction to 0.2 moles each of benzyl alcohol and chlorosulfonyl isocyanate to give benzyloxycarbonylsulfamoyl chloride.

b. Preparation of 2-(benzyloxycarbonylaminosulfonyloxy)benzoic acid benzyl ester sodium salt.

To the solution prepared in (a) containing approximately 0.2 mole of benzyloxycarbonylsulfamoyl chloride was added a solution of 22.8 g (0.1 mole) of benzylsalicylate, 16 ml (0.2 mole) of pyridine and 0.5 g of dimethylaminopyridine in 70 ml of methylene chloride at about 10° C. over a 10 min period. The reaction mixture was stirred overnight at room temperature and then extracted once with dilute hydrochloric acid followed by water. Both aqueous layers were back extracted with methylene chloride. The combined organic layers were dried and evaporated to give an oil. The oil was dissolved in a small amount of tetrahydrofuran (THF) and filtered to remove some insoluble solid. The THF filtrate was added to about 300 ml of saturated sodium bicarbonate solution and the resulting suspension was stirred overnight. The solid was collected by filtration, rinsed twice with water and twice with isopropyl alcohol-isopropyl ether and dried by pulling air through the filter to a weight of 25.88 g (56% yield of sodium salt). A second crop of 5.60 g (12%) was also obtained.

c. Preparation of title compound.

The 2-(benzyloxycarbonylaminosulfonyloxy)benzoic acid benzyl ester sodium salt prepared above, [35.3 g (0.076 mole)] was suspended in 500 ml of methanol was mixed with 6.2 ml of concentrated hydrochloric acid and 2 g of 5% palladium on carbon wetted with 50 ml methanol. The mixture was hydrogenated with hydrogen gas for four hr and filtered. The filtrate was concentrated to an oil. The oil was suspended in THF and filtered to remove some solids. The clear filtrate was concentrated and mixed with 1,1,1-trichloroethanol to precipitate the product as 8.82 g of light purple solid obtained after filtration. The purple solid was dissolved in THF and the solution was treated with charcoal, filtered and concentrated. The solid was recrystallized from 1,1,1-trichloroethane to give 6.5 g of white solid (39%), mp 139°–140° C.

Analysis: Calculated for $C_7H_7NO_5S$: C, 38.71; H, 3.25; N, 6.45; Found: C, 38.16; H, 3.24; N, 6.55.

EXAMPLE 51

1-Chloro-3-(2-methoxyphenoxy)-2-propanol methylsulfamate ester.

A solution of 109.3 g (0.55 mole) of glyceryl guaiacolate in 177 ml (2.20 moles) of pyridine and 700 ml methylene chloride was added to a solution of 283 g (2.20 moles) of methylaminosulfonyl chloride in 700 ml of methylene chloride. The addition was made over one hour at 15°-22° C. The solution was stirred at 23° C. for two hours then washed with 3×500 ml water. The methylene chloride solution was dried over type 3A molecular sieves. The mixture was filtered and the filtrate diluted with 140 ml of ethyl acetate. The solution was chromatographed on 2 kg of silica gel using 10% ethyl acetate: methylene chloride solution as eluent. The first 3×750 ml fractions were combined and concentrated to 77.3 g of brown oil. The oil was redissolved in 400 ml of 10% ethyl acetate: methylene chloride solution and chromatographed on 1.5 kg of silica gel. A total of 9×250 ml fractions were collected that showed only one spot on TLC.

The fractions were combined and concentrated to 20.6 g of oil which crystallized on standing.

The 20.6 g was recrystallized from 20 ml of isopropyl alcohol to give 6.9 g of white solid, mp 84°-85° C. The compound was characterized by $^1$H NMR, $^{13}$C NMR and C-I mass spec.

Analysis: Calculated for $C_{11}H_{16}ClNO_5S$: C, 42.65; H, 5.21; N, 4.52; Found: C, 42.32; H, 5.25; N, 4.61.

EXAMPLE 52

Process Demonstration

1-[(2-Methoxyphenoxy)methyl]-1,2-ethanediol bissulfamate (ester).

A solution of 10.4 g (0.06 mole) of sulfamic acid phenyl ester, 4.0 g (0.02 mole) of glyceryl guaiacolate and 2 ml of pyridine in 30 ml of p-dioxane was heated at reflux (104° C.) for 0.5 hr. The solution was cooled to 25° and 30 ml of methylene chloride was added. The solution was extracted with a dilute sodium bicarbonate solution. The sodium bicarbonate solution was prepared by dissolving 2 g of sodium bicarbonate in 25 ml water.

After the bicarbonate extraction, the methylene chloride solution was washed with 25 ml of water then concentrated to a brown liquid. The addition of a mixture of 24 ml water and 24 ml isopropyl ether caused a white solid to precipitate. The solid was collected and dried to yield 5.4 g (76%) of title compound.

EXAMPLE 53

2-(4-Chlorophenoxy)ethanol sulfamate (ester).

A mixture of 32.4 g (0.47 mole) of methylamine hydrochloride (98%, Aldrich), 39 ml (0.47 mole) of sulfuryl chloride (97%, Aldrich), and 0.4 ml of antimony (V) pentachloride (Baker) in 150 ml of acetonitrile was heated at reflux for 4 hr. To the reaction mixture was added an additional 39 ml (0.47 mole) of sulfuryl chloride (97%, Aldrich) and heating at reflux was continued overnight. The solvent was evaporated under reduced pressure to give 57.4 g (94%) of methyl sulfamoyl chloride as a light-brown oil.

To a stirred solution of 45.0 g (0.347 mole) of methylsulfamoyl chloride prepared above in 100 ml of methylene chloride was added in a thin stream a solution of 25.0 g (0.145 mole) of 2-(4-chlorophenoxy)ethanol (Lancaster Synthesis, Inc., Windham, N.H. 03087) in 30 ml (0.369 mole) of pyridine and 100 ml of methylene chloride and the reaction mixture was stirred at ambient temperature for 3 days. The solids were removed by filtration and the filtrate was evaporated under reduced pressure to yield a brown viscous residue. The residue was partitioned between water and ethyl ether (400 ml each). The organic layer was washed twice with 300 ml portions of water, dried over magnesium sulfate (MgSO$_4$) and the solvent evaporated under reduced pressure to yield a solid residue. The solid was triturated with 100 ml of isopropyl ether and the solid was recollected by filtration. The solid was recrystallized from isopropyl ether to give 12.9 g (34%) of title compound as a white solid, m.p. 101°-104° C.

Analysis: Calculated for $C_9H_{12}ClNO_4S$: C, 40.68; H, 4.55; N, 5.27; Found: C, 40.78; H, 4.62; N, 5.25.

EXAMPLE 54

3-Phenoxy-1-butanol sulfamate (ester).

The title compound was prepared by procedures of Example 33 from sulfamoyl chloride and 3-phenoxy-1-butanol. The viscous oil obtained was purified by high pressure chromatography using a Waters Associates Prep LC/System 500A; Prepak 500 ® silica and methylene chloride as eluting agent at a flow rate of 200 ml/min. Fractions containing the title compound were combined and the solvent was evaporated under reduced pressure to give 12.7 g (67%) of title compound as yellow, viscous oil.

Analysis: Calculated for $C_{10}H_{15}NO_4S$: C, 48.97; H, 6.16; N, 5.71; Found: C, 47.70; H, 6.22; N, 5.52.

Analysis: Calculated for $C_{10}H_{15}NO_4S\bullet 0.1CH_2Cl_2$: C, 47.80; H, 6.04; N, 5.52.

EXAMPLE 55

2-(4-Chlorophenoxy)ethanol dimethylsulfamate (ester).

A solution of 25.0 g (0.145 mole) of 2-(4-chlorophenoxy)ethanol (Lancaster Synthesis Inc., Windham, N.H. 03087) in 64.6 g (0.640 mole) of triethylamine and 40 ml of methylene chloride was added in a thin stream to a solution of 83.3 g (0.580 mole) of dimethylsulfamoyl chloride (Aldrich) in 60 ml of methylene chloride stirred at ambient temperature in a water bath. The reaction mixture was stirred for 8 days at ambient temperature. The solids were removed by filtration and the filtrate was evaporated under reduced pressure to yield a viscous residue. The residue was partitioned between water and ethyl ether (300 ml each). The organic layer was washed with two 200 ml portions of 2N hydrochloric acid. Once with 200 ml of water, dried over magnesium sulfate and the solvent evaporated under reduced pressure to yield a viscous residue. The residue was treated with 65.0 g (0.63 mole) of triethylamine and the reaction mixture was stirred for 5 days at ambient temperature. The solids were removed by filtration and the filtrate was evaporated under reduced pressure and the viscous residue was partitioned between water and ethyl ether (450 ml each). The organic layer was washed with four 300 ml portions of water (pH neutral to pH paper), dried over magnesium sulfate and the solvent evaporated under reduced pressure to yield a brown viscous oily residue. The oil was purified by chromatography (4.5×90 cm glass column; 500 g of silica gel; methylene chloride). Fractions containing the title compound were combined and the solvent evaporated under reduced pressure to yield a viscous oil. The oil was dissolved in 150 ml of isopropyl ether and filtered to remove some insolubles. The filtrate was concentrated to a viscous oil. The oil was triturated with isopropyl ether-petroleum ether (bp range 30°-60° C.), cooled (refrigerator) and the resulting solid was collected by filtration. The solid was recrystallized from isopropyl ether to give 18.5 g (45%) of white solid, mp 54°-57° C.

Analysis: Calculated for $C_{10}H_{14}ClNO_4S$: C, 42.94; H, 5.04; N, 5.01; Found: C, 43.20; H, 5.11; N, 4.94.

EXAMPLE 56

2-Methyl-2-phenoxypropanol sulfamate (ester).

This compound was prepared by the procedure used to synthesize 2-(4-methylphenoxy)ethanol sulfamate in Example 33. Thus, 13.2 g (0.0794 mole) of 2-methyl-2-phenoxypropanol was reacted with sulfamoyl chloride prepared from 26.5 ml (0.298 mole) of chlorosulfonyl isocyanate (98%, Aldrich), 33.9 g (0.336 mole) of triethylamine, and 5.3 g (0.294 mole) of water in 250 ml of acetonitrile. The 12.4 g of a viscous, oily residue obtained was purified by high pressure liquid chromatography (Waters Associates Prep LC/System 500A; PrePAK 500® silica; methylene chloride), then by chromatography (4.5×90 cm glass column; 500 g of silica gel; methylene chloride). Fractions containing title compound were combined and the solvent was evaporated under reduced pressure to give 5.4 g (28%) of a viscous oil.

Analysis: Calculated for $C_{10}H_{15}NO_4S$: C, 48.97; H, 6.16; N, 5.71; Found: C, 48.11; H, 6.18; N, 5.58.

EXAMPLE 57

Dimethylsulfamic acid diester with 3-(2-methoxyphenoxy)-1,2-propanediol.

A mixture of 19.8 g (0.1 mole) of glyceryl guaiacolate, 114.9 g (0.8 mole) of dimethylsulfamoyl chloride (Aldrich) and 89.2 g (0.88 mole) of triethylamine was stirred at ambient temperature for 5 days. To this mixture was added an additional 58 g (0.4 mole) of dimethylsulfamoyl chloride (Aldrich) and 45 g (0.45 mole) of triethylamine and the mixture was stirred at ambient temperature for 2 days, treated with water and ethyl acetate (400 ml each). The layers were separated and the organic layer was washed with six 300 ml portions of water, dried over magnesium sulfate and the solvent evaporated under reduced pressure to yield a viscous oil. The oil was purified by chromatography (4.5×90 cm glass column; 500 g of silica gel; methylene chloride). Fractions containing title compound were combined and the solvent was evaporated under reduced pressure to give 10.3 g (25%) of an oil that solidified upon standing. The solid was recrystallized from methylene chloride-ethyl ether to give 9.6 g (23%) of white solid, mp 78°-81° C.

Analysis: Calculated for $C_{14}H_{24}N_2O_8S_2$: C, 40.77; H, 5.87; N, 6.79; Found: C, 40.75; H, 5.98; N, 5.58.

EXAMPLE 58

4-Chlorophenol sulfamate ester.

In one portion, 96 g (0.75 mole) of 4-chlorophenol was added to a stirred solution of 67.5 ml (0.75 mole) of chlorosulfonylisocyanate in 400 ml of toluene. The solution was heated at 100° C. for 16 hr and the solution chilled with an ice-acetone bath and water added dropwise until evolution of carbon dioxide ceased. The tan solid which precipitated from solution was collected and dried for 16 hr to yield 133.4 g. A 25 g portion was recrystallized from 100 ml of toluene to give 15.8 g of white solid, mp 103°-104° C.

Analysis: Calculated for $C_6H_5ClNO_3S$: C, 34.71; H, 2.91; N, 6.75; Found: C, 34.73; H, 2.92; N, 6.74.

EXAMPLE 59

3-Chlorophenol sulfamate ester.

By the procedure of Example 58, 96 g (0.75 mole) of 3-chlorophenol and 67.5 ml (0.75 mole) of chlorosulfonyl isocyanate gave 122.9 g of solid product. A 25 g portion was recrystallized from 100 ml of toluene to give 11.8 g of white solid, mp 82°-83° C.

Analysis: Calculated for $C_6H_6ClNO_3S$: C, 34.71; H, 2.91; N, 6.75; Found: C, 34.69; H, 2.90; N, 6.74.

EXAMPLE 60

Methylsulfamic acid 2-[(aminosulfonyl)oxy]-1-[(2-methoxyphenoxy)methyl]ethyl ester.

A mixture of 8.0 g (0.0288 mole) of 3-(2-methoxyphenoxy)-2-hydroxypropanol sulfamate ester, 9.3 g (0.0721 mole) of methylsulfamoyl chloride and 7.3 g (0.0723 mole) of triethylamine was stirred at ambient temperature for 72 hr, treated with methylene chloride and water (150 ml each), and stirred vigorously for 10 min. The layers were separated and the organic layer was washed with four 150 ml portions of water, dried (over magnesium sulfate) and the solvent was evaporated under reduced pressure to yield a brown, viscous oil. The oil was purified by high pressure liquid chromatography (Waters Associates Prep LC 500A System; PrePAK 500 silica; methylene chloride-acetone; 9:1; flow rate: 100 ml/min). Fractions containing the title compound were combined and the solvents were evaporated under reduced pressure to give 2.2 g of a dark, viscous oil. The oil was dissolved in 100 ml of methylene chloride, treated with charcoal and filtered. The filtrate was evaporated under reduced pressure to give 2.1 g (20%) of title compound as a yellow gum.

Analysis: Calculated for $C_{11}H_{18}N_2O_8S_2$: C, 35.67; H, 4.90; N, 7.56; Found: C, 34.04; H, 4.95; N, 7.32.

EXAMPLE 61

Methylsulfamic Acid Phenyl Ester.

The reaction flask was charged with 34.1 g (0.20 mole) of methylaminosulfonyl chloride, 18.8 g (0.20 mole) of phenol and 150 ml of toluene. The dark, red solution was heated at 110° C. for 16 hours. The solution was cooled and washed with a solution of 16 g of sodium bicarbonate in 80 ml water. The toluene solution was washed with water then stirred with Type 3A molecular sieve powder and Norite "A" activated charcoal. After filtration, the filtrate was concentrated to 32.7 g of oil (87% crude yield). The oil was dissolved in 100 ml methylene chloride and chromatographed on silica gel. The main fraction was concentrated to an oil which solidified after chilling for 3 days. The solid was triturated with petroleum ether to give 16.1 g of solid, mp 43°-45° C. A recrystallization from a mixture of isopropyl acetate (2 ml/g) and petroleum ether (4 ml/g) gave 12.3 g of solid, mp 44°-46° C.

Analysis: Calculated for $C_7H_9NO_3S$: C, 44.91; H, 4.85; N, 7.48; Found: C, 44.84; H, 4.87; N, 7.47.

EXAMPLE 62

Sulfamic acid 4-oxo-4-phenylbutyl ester.

A cold (−10° C.) solution of 5.20 ml (0.06 mole) chlorosulfonyl isocyanate in 50 ml of methylene chloride was treated with a solution of 0.11 ml of water in 5 ml of acetonitrile over a period of 30 min. A solution of 6.56 g (0.04 mole) of 4-oxo-4-phenylbutanol and 8.34 ml (0.06 mole) of triethylamine in 30 ml of methylene chloride was then added to the solution of the sulfamoyl chloride at 0° to 10° C. over 20 min. The reaction mixture was stirred at room temperature for 4 hr. extracted once with water and once with sodium bicarbonate solution. The aqueous layers were back extracted with methylene chloride. The combined organic layers were dried (magnesium sulfate) and concentrated to an oil that solidified on standing. The solid was triturated with 1,1,1-trichloroethane to give 3.90 g of off-white solid. Recrystallization from acetonitrile-1,1,1-trichlorethane yielded 3.2 g of off-white solid, mp 78°-80° C.

Analysis: Calculated for $C_{10}H_{13}NO_4S$: C, 49.37; H, 5.30; N, 5.76; Found: C, 48.90; H, 5.48; N, 5.81.

EXAMPLE 63

1-[2-[(Aminosulfonyl)oxy]ethyl]-2-pyrrolidinone.

A solution of 6.5 g (0.05 mole) of 1-(2-hydroxyethyl)-2-pyrrolidone (Fluka) in 100 ml of methylene chloride was treated with 5.8 g (0.05 mole) of sulfamoyl chloride. The solution was stirred for 2 hr, then concentrated under vacuum. The residue was crystallized twice from 2-propanol to give 6.9 g (66%) of the title compound as white crystals, mp 110°-112° C. The compound was noted to be slightly hygroscopic.

Analysis: Calculated for $C_6H_{12}N_2O_4S$: C, 34.61; H, 5.81; N, 13.45; Found: C, 34.16; H, 5.97; N, 13.14.

EXAMPLE 64

2,3-Dihydro-1H-indole-1-propanol sulfamate ester hydrochloride.

Using the procedure in Example 62, 5.3 g (0.03 mole) of 1-(3-hydroxypropyl) indoline (Preparation 17) was used to prepare the title compound. The crude product, a brown oil weighing 6.2 g, was dissolved in isopropyl alcohol and the solution chilled and acidified with 37% hydrochloric acid solution. The off-white solid that formed was collected and rinsed with a mixture of isopropyl alcohol-isopropyl ether. The solid (5.3 g) was recrystallized by dissolving in 100 ml of methanol at 40° C., addition of isopropyl alcohol, and removal of most of the methanol by careful evaporation. The solid product was collected, rinsed with a mixture of isopropyl alcohol-isopropyl ether, and dried in vacuo at 50° C. for 18 hr to give 4.8 g (55%) of white solid, mp 134°-135° C.

Analysis: Calculated for $C_{11}H_{16}N_2O_3S \cdot HCl$: C, 45.13; H, 5.85; N, 9.57; Found: C, 44.86; H, 5.95; N, 9.44.

EXAMPLE 65

N-[4[(Aminosulfonyl)oxy]phenyl]acetamide.

A reaction flask was charged with 43.8 g (0.252 mole) of sulfamic acid, phenyl ester; 12.6 g (0.084 mole) of 4-acetamidophenol, 9 ml of pyridine and 150 ml p-dioxane. The solution was heated at 75° C. for 18 hours. The solution was concentrated to a brown oil. The oil was portioned between 100 ml methylene chloride and 100 ml of 1.0 N sodium bicarbonate. The mixture was refrigerated overnight then filtered to collect 15.8 g of white solid. $^1H$ NMR spectrum indicated pure product but contaminated with sodium bicarbonate. The solid was added to 100 ml $H_2O$ and the mixture stirred for one hour. The solid was collected and dried to give 8.4 g of solid, mp 180°-181° C.

Analysis: Calculated for $C_8H_{10}N_2O_4S$: C, 41.73; H, 4.38; N, 12.17; Found: C, 41.72; H, 4.42; N, 11.99.

EXAMPLE 66

1H-Indole-1-propanol sulfamate ester.

Using the procedure of Example 62, 5.25 g (0.03 mole) of 1-(-3-hydroxypropyl)indole (Preparation 18) was used to prepare the title compound. The crude product, 4.7 g, was purified by preparative high pressure liquid chromatography to yield 1.95 g of solid after removal of solvents, mp 65°-66° C.

Analysis: Calculated for $C_{11}H_{14}N_2O_3S$: C, 51.95; H, 5.55; N, 11.02; Found: C, 51.92; H, 5.62; N, 10.98.

EXAMPLE 67

Methylsulfamic acid 2-hydroxy-3-(2-methoxyphenoxy)propyl ester.

A solution of 26.5 g (0.13 mole) of glycerol guaiacolate in 100 ml of methylene chloride and 10.8 ml (0.13 mole) of pyridine was added in a thin stream to a stirred solution of 17.1 g (0.13 mole) of N-methylsulfamoyl chloride (Preparation 24) in 70 ml of methylene chloride, and the reaction mixture was stirred at ambient temperature for 2 hr. The reaction mixture was treated with 150 ml of water, the layers were separated, and the organic layer was washed successively with a 200 ml portion of 2N hydrochloric acid solution, four 200 ml portions of water, dried (magnesium sulfate), and the solvent was evaporated under reduced pressure to yield a viscous oil. The oil was purified by preparative high pressure liquid chromatography. Fractions containing the desired product were combined and the solvents evaporated under reduced pressure to give 13.9 g (37%) of the title compound as a yellow gum.

Analysis: Calculated for $C_{11}H_{17}NO_6S$: C, 45.35; H, 5.88; N, 4.81; Found: C, 44.99; H, 5.95; N, 4.78.

EXAMPLE 68

3-(2-Methoxyphenoxy)-1,2-propanediol 1-sulfamate.

To a cold solution (5° C.) of 19.2 ml (0.22 mole) of chlorosulfonyl isocyanate in 180 ml of acetonitrile was added 23.8 g (0.22 mole) of benzyl alcohol (reaction mixture temperature, 5°-8° C.). To this reaction mixture was added a solution of 39.6 g (0.2 mole) of glyceryl guaiacolate and 23.2 g (0.23 mole) of triethylamine in 180 ml of acetonitrile (reaction temperature, 5°-12° C.). The reaction mixture was stirred for 3 hr, and the solids were removed by filtration. The filtrate was stirred with 1.5 g of 5% Pd-C for 1 hr, filtered, and the filtrate was divided into two equal fractions. Each fraction was stirred with 1.5 g of 5% Pd-C and hydrogenated. The catalyst was removed by filtration, and the filtrates were concentrated under reduced pressure to give 45 g and 42.3 g respectively. $^{13}C$ NMR showed the fractions to be identical. The two fractions were combined and were purified by chromatography (4.5×90 cm glass column; 550 g of silica gel; methylene chloride-acetone, 5:1). Fractions containing the desired component were combined and the solvents evaporated under reduced pressure to give 13.8 g of a viscous oil. The oil was triturated with methylene chloride and insolubles were removed by filtration. The filtrate was evaporated under reduced pressure to give 12.9 g of a viscous oil. A 4.0 g sample of this oil was purified by high pressure liquid chromatography (Waters Associates Prep LC/System 500A; PrepPAK 500 silica; methylene chloride-acetone, 10:1; flow rate 200 ml/min. Fractions containing the desired component were combined, and the solvents evaporated under reduced pressure to give 2.3 g (58% recovery) of the title compound as a brown gum containing a trace of methylene chloride.

Analysis: Calculated for $C_{10}H_{15}NO_6S$: C, 43.32; H, 5.45; N, 5.05; Found: C, 42.60; H, 5.48; N, 4.96.

Analysis: Calculated for $C_{10}H_{15}NO_6S \cdot 0.04CH_2Cl_2$: C, 42.96; H, 5.42; N, 4.99.

EXAMPLE 69

Methylsulfamic acid 2-[(aminosulfonyl)oxy]-3-(2-methoxyphenoxy)propyl ester.

To a cold solution (ice-acetone bath) of 14.7 ml (0.166 mole) of chlorosulfonyl isocyanate (98%; Aldrich) in 100 ml of acetonitrile was added dropwise a solution of 2.7 g (0.15 mole) of water in 5 ml of acetonitrile such that the reaction mixture temperature was maintained at $\leq 7°$ C. The mixture was stirred vigorously for 10 min, and to it was added a solution of 12.3 g (0.042 mole) of 3-(2-methoxyphenoxy)-1,2-propanediol methyl sulfamate ester (Example 68) and 17.0 g (0.168 mol) of triethylamine in 100 ml of acetonitrile at such a rate that the temperature of the reaction mixture was maintained at $\leq 12°$ C. The reaction mixture was stirred vigorously for 3 hr at ambient temperature and treated with 100 ml of water and 200 ml of ethyl acetate. The layers were separated, and the organic layer was washed with 200 ml of water and evaporated under reduced pressure to yield a viscous residue. The residue was partitioned between 200 ml of water and 300 ml of ethyl ether. The organic layer was washed with three 200 ml portions of water (pH neutral to pH paper), dried over magnesium sulfate and the solvent evaporated under reduced pressure to give 8.5 g (55%) of a viscous, oily residue which solidified upon standing. The solid was triturated with 75 ml of methylene chloride, and the precipitate was collected by filtration to yield 4.2 g (27%) of the title compound as a white solid, mp 110°–113° C.

Analysis: Calculated for $C_{11}H_{18}N_2O_8S_2$: C, 35.67; H, 4.90; N, 7.56; Found: C, 35.54; H, 4.96; N, 7.54.

EXAMPLE 70

2-(8-Quinolinyloxy)ethanol sulfamate ester hydrochloride.

Using the procedure of Example 63, 5.4 g (0.029 mole) of 2-(8-quinolinyloxy)ethanol was reacted with sulfamoyl chloride. During work-up of the reaction, quite a bit of light-yellow material deposited out from the organic-aqueous system. $^1$H NMR of this material suggested that it might be a quaternary salt. The oily product obtained at the end of the work-up procedure weighted 2.7 g. This oil was dissolved in acetonitrile-isopropyl alcohol and acidified with 37% hydrochloric acid. The mixture was evaporated to almost dryness and then redissolved in methanol. To the solution was added ethyl acetate and most of the methanol was evaporated carefully. The light-yellow solid was collected and dried at 40° C. in vacuum overnight to give 2.4 g solid, mp 138°–140° C.

Analysis: Calculated for $C_{11}H_{12}N_2O_4S \cdot HCl$: C, 43.35; H, 4.30; N, 9.19; Found: C, 43.26; H, 4.38; N, 9.04.

EXAMPLE 71

Methylsulfamic acid 4-chlorophenyl ester.

A solution of 18.1 g (0.14 mole) of N-methylsulfamoyl chloride (Preparation 24) in 20 ml methylene chloride was added at 10°–20° C. to a solution of 12.8 g (0.10 mole) of 4-chlorophenol and 15 g (0.15 mole) of triethylamine in 50 ml of methylene chloride. The cooling was removed and the mixture stirred at ambient temperature for four hours. The mixture was filtered to remove the triethylamine hydrochloride. The filtrate was extracted with dilute HCl (6 ml of 37% hydrochloric acid in 60 ml water) followed by a water wash. The organic layer was then extracted with dilute potassium carbonate (8.0 g in 80 ml water) followed by a water wash. The methylene chloride layer was concentrated to 21.7 g of yellow oil which crystallized on cooling. The solid was stirred in a mixture of 10 ml toluene and 63 ml petroleum ether to obtain 20.3 g of yellow solid. The 20.3 g was recrystallized from 1:2 toluene: petroleum ether to give 8.73 g of white solid, mp 61°–62° C.

Analysis: Calculated for $C_7H_8ClNO_3S$: C, 37.93; H, 3.64; N, 6.32; Found: C, 37.59; H, 3.69; N, 6.42.

EXAMPLE 72

Ethylsulfamic acid 2-[[(ethylamino)sulfonyl]oxy]-3-(2-methoxyphenoxy)propyl ester.

A solution of 19.8 g (0.1 mole) of glyceryl guaiacolate in 100 ml of methylene chloride and 21.6 ml (0.26 mole) of pyridine was added in a thin stream to a stirred solution of 37.3 g (0.26 mole) of ethylsulfamoyl chloride (Preparation 25) in 150 ml of methylene chloride, and the reaction mixture was stirred at ambient temperature overnight. The reaction mixture was treated with 150 ml of 2N hydrochloric acid solution, and the layers were separated. The organic layer was washed with 150 ml of 2N hydrochloric acid solution, twice with 150 ml portions of water, dried (magnesium sulfate), and the solvent was evaporated under reduced pressure. The residue was purified by chromatography (4.5×90 cm glass column; 500 g of silica gel; methylene chloride-acetone, 25:1). Fractions containing the product were combined, and the solvents were evaporated under reduced pressure to give 20.2 g (49%) of the title compound as a light-yellow, viscous oil containing a trace of methylene chloride.

Analysis: Calculated for $C_{14}H_{24}N_2O_8S_2$: C, 40.77; H, 5.86; N, 6.79; Found: C, 40.21; H, 5.94; N, 6.77.

Analysis: Calc. for $C_{14}H_{24}N_2O_8S_2 \cdot 0.03CH_2Cl_2$: C, 40.60; H, 5.84; N, 6.75.

EXAMPLE 73

Ethylsulfamic acid 2-[[(ethylamino)sulfonyl]oxy]-3-phenoxypropyl ester.

This compound was prepared by the procedure used in Example 72. Thus, 17.7 g (0.1 mole) of 3-phenoxy-1,2-propanediol (95%, Aldrich), 37.3 g (0.26 mole) of ethylsulfamoyl chloride, and 21.6 ml (0.26 mole) of pyridine in 250 ml of methylene chloride gave 37.5 g of a yellow, viscous residue which solidified upon standing. The solid was recrystallized from ethyl ether-petroleum ether (30°–60° C.) to give 23.3 g (61%) of the title compound as a white solid, mp 60°–63° C.

Analysis: Calculated for $C_{13}H_{22}N_2O_7S_2$: C, 40.83; H, 5.80; N, 7.33; Found: C, 40.59; H, 5.93; N, 7.30.

EXAMPLE 74

2,3-Dihydro-1,4-benzodioxin-2-methanol sulfamate ester.

This compound was prepared using the procedure used in Example 69. Thus 25.7 g (0.15 mole) of 2-hydroxymethyl-1,4-benzodioxan (97%, Aldrich), 52.3 ml (0.59 mole) of chlorosulfonyl isocyanate (98%, Aldrich), 61.6 g (0.61 mole) of triethylamine and 9.9 g (0.55 mole) of water in 250 ml of acetonitrile gave a viscous residue. The residue was partitioned between 700 ml of chloroform and 300 ml of water. The organic layer was washed with give 300 ml portions of water (aqueous layer pH was neutral to pH paper), dried (magnesium sulfate), and the solvent was evaporated under reduced pressure to give a semi-solid residue. This residue was triturated with 70 ml of chloroform-hexanes (1:4), and the resulting solid was collected by filtration. The solid was recrystallized from chloroform-hexanes to yield 9.0 g (24%) of the title compound as a white solid, mp 93°–95° C. [lit. mp 94°–96° C. (CHCl$_3$), *J. Med. Chem.* 30, 880 (1987)].

Analysis: Calculated for C$_9$H$_{11}$NO$_5$S: C, 44.08; H, 4.52; N, 5.71; Found: C, 44.19; H, 4.64; N, 5.76.

EXAMPLE 75

Sulfamic acid 2-(3-pyridinyloxy)ethyl ester hydrochloride.

A mixture of 4.9 g (0.035 mole) of 2(3-pyridinyloxy)ethanol (Preparation 20) and 8 g (0.046 mole) of sulfamic acid phenyl ester (Example 39) in 100 ml of dioxane was heated at reflux temperature for 20 min. and the solvent then evaporated. The residue was triturated with 250 ml of acetone, filtered, and the filtrate acidified with a solution of anhydrous hydrogen chloride in isopropyl alcohol and the sticky brown precipitate collected. The brown solid was redissolved in 125 ml of methanol and diluted with 125 ml of ethanol. The solution was stirred with charcoal, filtered, and the filtrate partially evaporated to give a suspension. The suspension was diluted with isopropyl alcohol-isopropyl ether and filtered. The solid was dried at 50° C. for 18 hr and then at 70° C. for 18 hr in a vacuum oven. The yield was 4.5 g of solid, mp 156°–157° C.

Analysis: Calculated for C$_7$H$_{10}$N$_2$O$_4$S.HCl: C, 33.01; H, 4.35; N, 11.00; Found: C, 33.51; H, 4.55; N, 10.43.

EXAMPLE 76

(1-Methylethyl)sulfamic acid 2-[[[1-methylethyl)amino]sulfonyl]oxy]-3-phenoxypropyl ester.

This compound was prepared according to the procedure of Example 72. Thus 19.5 g (0.11 mole) of 3-phenoxy-1,2-propanediol, 63.0 g (0.26 mole) of pyridine in 250 ml of methylene chloride gave 63.9 g of a brown, viscous oil. The oil was purified by column chromatography on silica gel using methylene chloride-acetone (60:1) to elute the material. Desired fractions were combined and concentrated to yield a white solid. The solid was recrystallized from ethyl ether-petroleum ether (30°–60° C.) to yield 28.1 g (62%) of white solid, mp 77°–80° C.

Analysis: Calculated for C$_{15}$H$_{26}$N$_2$O$_7$S$_2$: C, 43.89; H, 6.38; N, 6.82; Found: C, 43.82; H, 6.52; N, 6.84.

EXAMPLE 77

(1,1-Dimethylethyl)sulfamic acid 2-[[[(1,1-dimethylethyl)amino]sulfonyl]oxy]-3-phenoxypropyl ester.

This compound was prepared by the procedure used in Example 72. Thus, 13.7 g (0.077 mole) of 3-phenoxy-1,2-propanediol (95%, Aldrich), 31.3 g (0.18 mole) of N-(t-butylsulfamoyl) chloride (Preparation 23) and 15.2 ml (0.18 mol) of pyridine in 250 ml of methylene chloride gave 30.8 g of a dark, viscous oil. The oil was purified by chromatography (4.5×90 cm glass column, 500 g of silica gel, methylene chloride-acetone, 80:1). Fractions containing the desired compound were combined and the solvents evaporated under reduced pressure to yield a viscous oil that solidified upon standing. The solid was recrystallized from ethyl ether-petroleum ether (30°–60° C.) to give 12.9 g (38%) of the title compound as a white solid, mp 101.5°–103° C.

Analysis: Calculated for C$_{17}$H$_{30}$N$_2$O$_7$S$_2$: C, 46.56; H, 6.90; N, 6.35; Found: C, 46.66; H, 7.05; N, 6.38.

EXAMPLE 78

4-[(Aminosulfonyl)oxy]benzoic acid methyl ester.

Chlorosulfonylisocyanate (8.8 ml, 0.1 mole) was added to 200 ml toluene. Solid methyl 4-hydroxybenzoate (15.2 g, 0.1 mole) was added to the stirred solution. The mixture was heated at reflux for 1.5 hr then cooled and treated with about 8 ml water and some tetrahydrofuran. Solvents were then removed by evaporation. The residue was triturated with ethyl acetate-isopropyl ether. The insoluble solid was removed by filtration. The filtrate was concentrated and then triturated in isopropyl ether. The solid was collected and weighed 8.6 g. Recrystallization from acetone-isopropyl ether gave a white solid which was dried under vacuum overnight at room temperature to 3.9 g, mp 116°–118° C.

Analysis: Calculated for C$_8$H$_9$NO$_5$S: C, 41.56; H, 3.92; N, 6.06; Found: C, 41.53; H, 3.97; N, 6.05.

EXAMPLE 79

3-[(Aminosulfonyl)oxy]benzoic acid methyl ester.

Following the procedure of Example 78, a reaction of 8.8 ml (0.10 mole) chlorosulfonyl isocyanate and 15.2 g (0.10 mole) of methyl 3-hydroxybenzoate in 200 ml of toluene was heated at reflux for 7.5 hr and worked up to obtain 10.53 g, mp 145°–146° C.

Analysis: Calculated for C$_8$H$_9$NO$_5$S: C, 41.56; H, 3.92; N, 6.06; Found: C, 41.30; H, 3.94; N, 6.06.

EXAMPLE 80

N-[3-[(Aminosulfonyl)oxy]phenyl]acetamide.

By the same method described for Example 62, the title compound was prepared from m-acetamidophenol (12.10 g, 0.08 m), reacting with the sulfamoyl chloride generated from water and chlorosulfonyl isocyanate. The crude product contained desired product and starting material. The product was isolated by chromatography on 100 g silica gel, eluted first with 7:3 methylene chloride/acetonitrile and then increasing the proportion of acetonitrile in the eluting solvent. The main fraction was evaporated and triturated with isopropyl alcohol/isopropyl ether to give 4 g of white solid, recrystallized from acetonitrile/isopropyl ether, and dried in vacuum at 60° C. overnight to give 3.73 g of solid, mp 148°–149° C.

Analysis: Calculated for C$_8$H$_{10}$N$_2$O$_4$S: C, 41.73; H, 4.38; N, 12.17; Found: C, 42.06; H, 4.46; N, 12.35.

EXAMPLE 81

4-[(Aminosulfonyl)oxy]benzoic acid.

Benzyl 4-hydroxybenzoate (22.8 g, 0.1 mole) was converted to its benzyloxycarbonylsulfamoyl derivative by the same procedure as described in Example 50. This intermediate was isolated as an oil and was hydrogenated over 5% Pd-C by the same manner to give 4.5 g solid. Recrystallization from methanol-acetonitrile yielded 3 g of pure product, mp 184°–186° C.

Analysis: Calculated for C$_7$H$_7$NO$_5$S: C, 38.71; H, 3.25; N, 6.45; Found: C, 38.71; H, 3.32; N, 6.62.

EXAMPLE 82

Sulfamic acid 4-(1H-imidazol-1-yl)phenyl ester.

To a chilled solution of chlorosulfonyl isocyanate (8.7 ml, 0.10 mole) in 50 ml of methylene chloride was added a solution of 10.8 g (0.10 mole) of benzyl alcohol in 200 ml of methylene chloride over a period of 6 minutes at 3°–15° C. The reaction was then stirred at ambient temperature for 2 hours and then chilled in an ice-water bath. To this solution was added 4-(imidazol-1-yl)phenol (12 g, 0.075 mole) as a solid, and the mixture was stirred at room temperature for 45 minutes. Triethylamine (14 ml, 0.1 mole) was then added to the suspension, and the reaction became a dark brown solution. The mixture was stirred for two days, and the solid was collected by filtration, stirred in water for half an hour, and filtered again, rinsed with isopropyl alcohol and isopropyl ether. This solid intermediate weighed 18.24 g (65%) and $^1$H NMR showed it exists as zwitterion. The zwitterion (18 g) was added to a solution of isopropyl alcohol containing 0.05 mole hydrogen chloride and diluted with 100 ml methanol. The resultant solution was mixed with 1.8 g Pd-C (5%) and hydrogenated until there was no further absorption of hydrogen. The catalyst was removed, and the solution was concentrated to give 10 g solid. Part of the solid was recrystallized by dissolving in excess amount of methanol, filtering, and concentrating to crystallize out about 5 g solid. The solid was dried in vacuum oven at 80° C. overnight, mp 198°–200° C.

Analysis: Calculated for $C_9H_9N_3O_3S.HCl$: C, 39.21; H, 3.66; N, 15.24; Found: C, 39.07; H, 3.65; N, 15.15.

EXAMPLE 83

(1-Methylethyl)sulfamic acid phenyl ester.

This compound was prepared according to the procedure of Example 61. Thus a solution of 16.2 g (0.17 mole) of phenol and 33.0 g (0.21 mole) of N-isopropyl-sulfamoyl chloride (Preparation 22) in 150 ml of toluene gave a dark oil which was purified by column chromatography on silica gel using ethyl acetate-hexanes (1:16) to elute the product. Desired fractions were combined and concentrated to yield 11.7 g (32%) of the title compound as a light-yellow oil.

Analysis: Calculated for $C_9H_{13}NO_3S$: C, 50.22; H, 6.09; N, 6.51; Found: C, 50.20; H, 6.23; N, 6.31.

EXAMPLE 84

Sulfamic acid (3,4-dichlorophenyl)ester.

A solution of 16.3 g (0.1 mole) of 3,4-dichlorophenol in 100 ml of toluene was heated at reflux utilizing a Dean-Stark trap to remove any water that may have been present. The solution was cooled in an ice bath, treated with 9.1 ml (14.8 g, 0.105 mole) of chlorosulfonyl isocyanate, and heated at reflux overnight. The solution was cooled in an ice bath, vigorously stirred, and treated dropwise with water until carbon dioxide evolution ceased. The solid which precipitated was collected by filtration, washed with water and benzene, dried, and recrystallized from benzene to yield 19.9 g (82%) of a white solid, mp 121°–123° C.

Analysis: Calculated for $C_6H_5Cl_2NO_3S$: C, 29.77; H, 2.08; N, 5.79; Found: C, 29.94; H, 2.10; N, 5.93.

EXAMPLE 85

Sulfamic acid (4-nitrophenyl ester).

This compound was prepared according to the procedure of Example 84. A mixture of 13.9 g (0.1 mole) of 4-nitrophenol and 14.8 g (0.105 mole) of chlorosulfonyl isocyanate in 100 ml of toluene gave 17.8 g (82%) of tan solid, mp 104°–111° C. (benzene-acetonitrile).

Analysis: Calculated for $C_6H_6N_2O_5S$: C, 33.03; H, 2.77; N, 12.84; Found: C, 33.29; H, 2.80; N, 12.85.

EXAMPLE 86

(Phenoxysulfonyl)carbamic acid ethyl ester.

Chlorosulfonyl isocyanate (98%, 13.4 ml, 0.15 mole) was stirred in 40 ml of methylene chloride in an acetone-ice bath. Ethanol (8.8 ml, 0.15 mole) dissolved in 20 ml methylene chloride was added dropwise over 28 minutes. The reaction was stirred at room temperature for 15 minutes and then chilled in an ice bath. To the reaction was added a solution of phenol (11.3 g, 0.12 mole) and triethylamine (21 ml, 0.15 mole) in methylene chloride (20 ml) over 27 minutes. The reaction was stirred at ambient temperature for 4 hours and then extracted twice with dilute hydrochloric acid. The organic layer was dried over sodium sulfate and evaporated to 31 g oil. This oil was chromatographed on about 300 g silica gel eluted with 2% ethyl acetate/methylene chloride. The pure fractions were combined and concentrated to 15 g oil.

Analysis: Calculated for $C_9H_{11}NO_4S$: C, 44.08; H, 4.52; N, 5.71; Found: C, 43.59; H, 4.55; N, 5.70.

EXAMPLE 87

Ethylsulfamic acid phenyl ester.

A solution of 18.8 g (0.2 mole) of phenol and 38.4 g (0.27 mole) of ethylaminosulfonyl chloride (Preparation 25) in 150 ml of toluene was stirred and heated at reflux for 16 hr. The solution was cooled and then treated with 250 ml of a 20% sodium bicarbonate solution. The layers were separated and the organic layer was washed successively with 250 ml of a 20% sodium bicarbonate solution, two 300-ml portions of water and dried (magnesium sulfate). The solvent was evaporated under reduced pressure and the oily residue was purified by chromatography (4.5×105 cm glass column; 550 g of silica gel; ethyl acetate-hexanes, 1:16). Fractions containing the product were combined and the solvents evaporated under reduced pressure to give 28.5 g (71%) of the title compound as a colorless liquid. Elemental analysis suggested that the product contained water.

Analysis: Calculated for $C_8H_{11}NO_3S.0.1H_2O$: C, 47.32; H, 5.56; N, 6.90; Found: C, 47.06; H, 5.69; N, 7.13.

EXAMPLE 88

Sulfamic acid 4-phenyl-1,2,5-thiadiazol-3-yl ester.

A slurry of 3-hydroxy-4-phenyl-1,2,5-thiadiazole (15.0 g, 0.084 mole) in acetonitrile (100 ml) was treated by the simultaneous dropwise addition of a sulfamoyl chloride solution in acetonitrile (0.20 mole, 66 ml of 3M) and a diisopropylethylamine solution (0.22 mole in enough 1:1 acetonitrile/methylene chloride to make 66 ml). High Pressure Liquid Chromatography analysis indicated a maximum of 85% conversion of starting material to product. The reaction was worked up by concentration of the reaction mixture and partitioning the residue between ethyl ether and water. Concentration of the ether fraction gave a white paste from which desired product was separated by dissolving in a small amount of acetonitrile. The product was crystallized from the acetonitrile to give 2.8 g (13%) of the title compound as a white powder, mp 128°–130° C.

Analysis: Calculated for $C_8H_7N_3O_3S_2$: C, 37.35; H, 2.74; N, 16.33; Found: C, 37.30; H, 2.75, N, 16.41.

EXAMPLE 89

Sulfamic acid 3-nitrophenyl ester.

This compound was prepared according to the procedure used in Example 84. A mixture of 13.9 g (0.1 mole)

of 3-nitrophenol and 14.8 g (0.105 mole) of chlorosulfonyl isocyanate in 100 ml of toluene gave 16.9 g (78%) of tan flakes, mp 118°–120° C.

Analysis: Calculated for $C_6H_6N_2O_5S$: C, 33.03; H, 2.77; N, 12.84; Found: C, 33.18; H, 2.81; N, 12.95.

EXAMPLE 90

Sulfamic acid 3-(trifluoromethyl)phenyl ester.

This compound was prepared according to the procedure used in Example 84. A mixture of 18.4 g (0.114 mole) of α,α,α-trifluoro-m-cresol, 14.8 g (0.105 mole) of chlorosulfonyl isocyanate and 100 ml of toluene gave 22.5 g (82%) of a white solid, mp 100°–102° C.

Analysis: Calculated for $C_7H_6F_3NO_3S$: C, 34.86; H, 2.51; N, 5.81; Found: C, 35.04; H, 2.48; N, 5.86.

EXAMPLE 91

Sulfamic acid (1,1'-biphenyl)-4-yl ester.

This compound was prepared according to the procedure used in Example 84. A mixture of 17.0 g (0.1 mole) of 4-phenylphenol, 14.8 g (0.105 mole) of chlorosulfonyl isocyanate and 100 ml of toluene gave 17.2 g (69%) of white crystals, mp 166°–168° C. (benzene-acetonitrile).

Analysis: Calculated for $C_{12}H_{11}NO_3S$: C, 57.82; H, 4.45; N, 5.62; Found: C, 58.06; H, 4.47; N, 5.66.

EXAMPLE 92

Sulfamic acid 4-nitro-3-(trifluoromethyl)phenyl ester.

This compound was prepared according to the procedure used in Example 84. A mixture of 10.4 g (0.05 mole) of 5-hydroxy-2-nitrobenzotrifluoride, 7.8 g (0.055 mole) of chlorosulfonyl isocyanate and 75 ml of toluene gave 11.1 g (78%) of tan solid, mp 95°–97° C. (benzene).

Analysis: Calculated for $C_7H_5F_3N_2O_5S$: C, 29.38; H, 1.76; N, 9.79; Found: C, 29.30; H, 1.69; N, 9.81.

EXAMPLE 93

Sulfamic acid 4-methyl-2-oxo-2H-1-benzopyran-7-yl ester.

A slurry of 7-hydroxy-4-methylcoumarin (17.6 g, 0.10 mole) in acetonitrile (100 ml) was treated with a total of 84 ml of 3M sulfamoyl chloride (0.255 mole) in acetonitrile. The mixture was then treated dropwise with triethylamine (25.8 g, 0.255 mole). The reaction temperature was allowed to rise to 45° without any cooling. The mixture was stirred overnight at ambient temperature. The precipitate was collected, triturated with water, and dried in a vacuum oven at 70° C. for 15 hr to give 10.5 g (41%) of white powder, mp 161°–164° C.

Analysis: Calculated for $C_{10}H_9NO_5S$: C, 47.06; H, 3.55; N, 5.49; Found: C, 47.08; H, 3.58; N, 5.56.

EXAMPLE 94

Sulfamic acid 2-chlorophenyl ester.

This compound was prepared by the procedure used in Example 84. A mixture of 12.8 g (0.1 mole) of 2-chlorophenol, 14.8 g (0.105 mole) of chlorosulfonyl isocyanate and 75 ml of toluene gave 12.2 g (59%) of the title compound as a white solid, mp 62.5°–63.5° C. (cyclohexane-benzene).

Analysis: Calculated for $C_6H_6ClNO_3S$: C, 34.71; H, 2.91; N, 6.75; Found: C, 34.50; H, 2.92; N, 6.76.

EXAMPLE 95

Methylsulfamic acid 4-(1H-imidazol-1-yl)phenyl ester monohydrochloride.

Triethylamine (11.2 ml, 0.08 mole) and 4-(imidazo-1-yl)phenol (9.6 g, 0.06 mole) were stirred in 100 ml methylene chloride as a suspension in an ice bath. To this suspension was added a solution of methylsulfamoyl chloride (10.8 g, 0.08 mole) in 10 ml methylene chloride over 4 minutes. The ice bath was then removed and the reaction was stirred at room temperature overnight. The grayish suspension slowly changed to a tan suspension. The solid was filtered and rinsed with methylene chloride and then dissolved in 300 ml methanol. The solution was acidified with HCl/isopropyl alcohol and stirred with charcoal. The almost colorless filtrate was mixed with some isopropyl alcohol and then concentrated. The residual solid was triturated in isopropyl alcohol/isopropyl ether, collected by filtration, and dried overnight at 80° C. in a vacuum oven to yield 11.34 g of solid, mp 221°–223° C.

Analysis: Calculated for $C_{10}H_{11}N_3O_3S \cdot HCl$: C, 41.46; H, 4.18; N, 14.50; Found: C, 41.40; H, 4.21; N, 14.38.

EXAMPLE 96

Sulfamic acid (2-naphthalenyl) ester.

To a cold (ice-acetone bath) solution of 11.3 ml (0.13 mole, 18.4 g) of chlorosulfonyl isocyanate in 50 ml of acetonitrile was added dropwise a solution of 2.3 g (0.13 mole) of water in 10 ml of acetonitrile at such a rate that the temperature was maintained between −2° to 7° C. (ca. 45 min). After the addition was complete, the solution was stirred for 5 min and then treated dropwise with a solution of 14.4 g (0.1 mole) of β-naphthol, 20.9 ml (0.15 mole, 15.2 g) of triethylamine and 100 ml of acetonitrile at such a rate that the temperature did not exceed 10° C. (ca. 30 min). The mixture was stirred at ambient temperature for 3.5 h and then diluted with 100 ml of ethyl acetate and 50 ml of water. The layers were separated and the organic layer was washed once with 50 ml of water and once with 100 ml of brine, dried (sodium sulfate), and concentrated to give 24 g of dark gum. The gum was purified by column chromatography on 400 g of silica gel eluted with methylene chloride. Fractions containing the desired product were combined and concentrated to yield 5.7 g (26%) of the title compound as a white solid, mp 114°–115° C. (benzene).

Analysis: Calculated for $C_{10}H_9NO_3S$: C, 53.80; H, 4.06; N, 6.27; Found: C, 53.83; H, 4.02; N, 6.25.

EXAMPLE 97

Methylsulfamic acid 3-phenoxy-1,2-propanediyl ester.

To a vigorously stirred solution of 17.7 g (0.1 mole) of 3-phenoxy-1,2-propanediol in 250 ml of methylene chloride was added simultaneously, over a 30 min period, 35.8 g (0.28 mole) of methylaminosulfonyl chloride (Preparation 24) and 36.0 g (0.28 mole) of diisopropylethylamine. The dark reaction mixture was stirred for 3 hr and the solvent was evaporated under reduced pressure to yield a brown, viscous oil. The oil was partitioned between ethyl acetate and a 2N hydrochloric acid solution (250 ml each). The organic layer was further washed with two 250-ml portions of 2N hydrochloric acid solution, 250 ml of water, and dried (magnesium sulfate). The solvent was evaporated under reduced pressure and the viscous, oily residue was purified by chromatography (4.5×105 cm glass column; 520 g of silica gel; methylene chloride-acetone, 100:3). Fractions containing the product were combined and the solvents evaporated under reduced pressure to give 25.7 g (73%) of the title compound as a pale-yellow gum.

Analysis: Calculated for $C_{11}H_{18}N_2O_7S_2$: C, 37.28; H, 5.12; N, 7.90; Found: C, 36.75; H, 5.17; N, 7.83.

EXAMPLE 98

Sulfamic acid 4-(2H-1,2,4-triazol-2-yl)phenyl ester hydrochloride (2:1).

4-(1H-1,2,4-triazol-1-yl)phenol (5.0 g, 0.031 mole) was suspended in methylene chloride (30 ml) and sulfamoyl chloride (7.13 g, 0.062 mole) added to the stirring mixture. Triethylamine (6.27 g, 0.062 mole) was added dropwise while maintaining the temperature between 25°–30° C. After the addition was complete the reaction was stirred for several hours at room temperature. An aliquot was removed and injected onto an High Pressure Liquid Chromatography diol column (10% methanol in ethyl acetate) which indicated reaction had not gone to completion. The reaction was treated with an additional 0.031 mole of sulfamoyl chloride and triethylamine. The reaction stirred overnight at room temperature and was worked up after $^1H$ NMR indicated reaction had gone to completion. The solvent was evaporated and the residue partitioned between ethyl acetate/acetonitrile (1:1)/aqueous sodium hydroxide, sodium bicarbonate (1:1). The organic layer was evaporated and the base isolated as an off-white powder (4.78 g, 64%). The crystals were dissolved in hot isopropyl alcohol, cooled and the mixture filtered. The filtrate containing the base was evaporated to a residue, dissolved in methanol and a solution of anhydrous HCl/isopropyl alcohol added. White crystals fell out of solution as more isopropyl alcohol was added and methanol removed. The crystals were filtered, dried and analyzed (0.80 g, 0.0029 mole, 9%, mp 169°–173° C.).

Analysis: Calculated for $C_8H_8N_4O.0.5HCl$: C, 37.18; H, 3.32; N, 21.68; Found: C, 36.93; H, 3.30; N, 21.44.

EXAMPLE 99

Sulfamic acid 4-benzoylphenyl ester.

This compound was prepared according to the procedure used in Example 84. A mixture of 9.9 g (0.05 mole) of 4-hydroxybenzophenone, 7.1 g (0.0505 mole) of chlorosulfonyl isocyanate and 75 ml of toluene gave 8.1 g (58%) of the title compound as off-white flakes, mp 131°–133° C.

Analysis: Calculated for $C_{13}H_{11}NO_4S$: C, 56.31; H, 4.00; N, 5.05; Found: C, 56.03; H, 3.92; N, 5.07.

EXAMPLE 100

Sulfamic acid 3-bromophenyl ester.

This compound was prepared according to the procedure used in Example 84. A mixture of 17.3 g (0.1 mole) of 3-bromophenol, 9.1 ml (14.8 g, 0.105 mole) of chlorosulfonyl isocyanate and 100 ml of toluene gave 19.8 g (70%) of white solid, mp 90°–91.5° C. (benzene).

Analysis: Calculated for $C_6H_6BrNO_3S$: C, 28.59; H, 2.40; N, 5.56; Found: C, 28.35; H, 2.46; N, 5.52.

EXAMPLE 101

Sulfamic acid 4-(trifluoromethyl)phenyl ester.

This compound was prepared according to the procedure used in Example 84. A mixture of 9.6 g (0.059 mole) of α,α,α-trifluoro-p-cresol, 5.7 ml (9.2 g, 0.065 mole) of chlorosulfonyl isocyanate and 75 ml of toluene gave 11.2 g (70%) of white solid, mp 111°–112° C. (benzene).

Analysis: Calculated for $C_7H_6F_3NO_3S$: C, 34.86; H, 2.51; N, 5.81; Found: C, 34.75; H, 2.47; N, 5.80.

EXAMPLE 102

Sulfamic acid 3-benzoylphenyl ester.

This compound was prepared according to the procedure used in Example 84. A mixture of 9.9 g (0.05 mole) of 3-hydroxybenzophenone and 4.4 ml (7.1 g, 0.0505 mole) of chlorosulfonyl isocyanate in 75 ml of toluene gave a solid as residue. This residue was recrystallized successively from benzene and then methylene chloride to yield 4.2 g (30%) of the title compound as a white solid, mp 72°–74° C.

Analysis: Calculated for $C_{13}H_{11}NO_4S$: C, 56.31; H, 4.00; N, 5.05; Found: C, 55.89; H, 3.95; N, 5.03.

EXAMPLE 103

Sulfamic acid 3-(dimethylamino)phenyl ester monohydrochloride.

A solution of 3-dimethylaminophenol (6.90 g, 0.05 mole) in 30 ml of acetonitrile was added in 13 minutes to a chilled (15° C.) stirred solution of 0.10 mole sulfamoyl chloride (Preparation 21) in 30 ml of acetonitrile. This was followed by the addition of 14 ml (0.10 mole) of triethylamine. The resultant mixture was stirred at room temperature overnight. The reaction was diluted with ethyl acetate (~60 ml) and then extracted twice with sodium bicarbonate solution. The aqueous layers were back extracted with 1:1 ethyl acetate/acetonitrile once. The organic layers were combined, dried over sodium sulfate, charcoaled, filtered, and evaporated to a black oil weighing 7.57 g.

The above reaction was repeated doubling the scale and all the black oil combined and chromatographed on 360 g of silica gel eluting with 10% acetonitrile/methylene chloride. The fractions containing the desired product also contained some starting material. These fractions were combined, concentrated, and redissolved in isopropyl alcohol. The solution was acidified with a solution of anhydrous HCl in isopropyl alcohol and crystallized to give 9.39 g of a light-greenish-brown solid. This solid was redissolved in methanol (charcoal) to give a light-blue filtrate. Evaporation and crystallization of the residue from isopropyl alcohol gave 8.5 g of off-white solid, mp 168°–70° C.

Analysis: Calculated for $C_8H_{12}N_2O_3S.HCl$: C, 38.02; H, 5.19; N, 11.09; Found: C, 38.05; H, 5.34; N, 11.11.

EXAMPLE 104

Methylsulfamic acid 2-[4-(1H-imidazol-1-yl)phenoxy]ethyl ester hydrochloride hydrate (2:2:1).

A solution of 4-imidazol-1-yl-phenol (20.0 g, 0.125 mole), 2-chloroethanol (40.25 g, 0.50 mole) and potassium carbonate (69.0 g, 0.50 mol) in 500 ml of methyl ethyl ketone was heated at reflux for 48 hr as its progress was being monitored by TLC (methanol:methylene chloride 10:90). The reaction was then filtered, and the filtrate evaporated to a solid which was redissolved in hot isopropanol. The crystals which formed upon cooling were filtered, rinsed with isopropyl ether, and dried (7.36 g, 28.9% yield, $^1H$ NMR: 95% pure). This intermediate alcohol (6.0 g, 0.029 mole) was suspended in methylene chloride (60 ml) and triethylamine (3.51 g, 0.0348 mole) added to the stirring suspension. The reaction was chilled at 10° C. and methylsulfamoyl chloride (4.51 g, 0.0348 mole) added dropwise allowing reaction to slowly warm to room temperature. After 1 hr of stirring, TLC indicated reaction was not complete so it was treated with additional 0.03 mole of base and methylsulfamoyl chloride and stirred overnight. After the reaction had gone to completion, it was evaporated to a residue. The residue was dissolved in ethyl acetate/acetonitrile (1:1) (200 ml) and washed with sodium bicarbonate/sodium chloride (1:1) (2×200 ml). The organic layer was evaporated and redissolved in hot ethanol. Upon cooling, crystals precipitated and were filtered and dried. They were then dissolved in methanol and anhydrous HCl in isopropyl alcohol added. A carbon filtration was done and the methanol evaporated as more isopropanol was added. Off-white crystals precipitated and were filtered, dried, and analyzed (4.14 g, 42%, mp 85°–88° C.).

Analysis: Calc. for $C_{12}H_{15}N_3O_4 \cdot HCl \cdot 0.5H_2O$: C, 42.05; H, 5.00; N, 12.26; Found: C, 42.30; H, 4.99; N, 11.91.

EXAMPLE 105

Sulfamic acid 4-(aminosulfonyl)phenyl ester.

This compound was prepared by the procedure used in Example 33. Thus, 20.2 g (0.12 mole) of p-hydroxybenzenesulfonamide, 43 ml (0.48 mole) of chlorosulfonyl isocyanate, 8.5 g (0.47 mole) of water and 53.3 g (0.53 mole) of triethylamine in 250 ml of acetonitrile gave 14.6 g of a viscous residue which solidified upon standing. The solid was purified by chromatography (4×150 cm glass column; 500 g of silica gel; acetone-methylene chloride, 1.5). Fractions containing the product were combined and the solvents evaporated under reduced pressure to give 9.0 g (30%) a solid. The solid was recrystallized from methylene chloride-acetone to give 2.1 g (7%) of the title compound as fluffy, white needles, mp 139°–142° C.

Analysis: Calculated for $C_6H_8N_2O_5S_2$: C, 28.57; H, 3.20; N, 11.11; Found: C, 28.50; H, 3.25; N, 10.99.

EXAMPLE 106

Sulfamic acid 2-(4-methyl-5-thiazolyl)ethyl ester hydrate 2-propanol (2:1:1).

4-Methyl-5-thiazoleethanol (10.0 g, 0.0698 mole) was dissolved in acetonitrile, chilled, and sulfamoyl chloride (10.44 g, 0.091 mole) was added to the stirred solution. Triethylamine (9.19 g, 0.091 mole) was added dropwise while maintaining the temperature between 20°–25° C. A yellow solid precipitated after the addition was completed. The reaction was stirred at room temperature overnight, evaporated to a residue, and the residue partitioned between ethyl acetate/acetonitrile (1:1) and sodium bicarbonate/sodium chloride (1:1). The organic phase was treated with charcoal, dried (magnesium sulfate), filtered, and evaporated to a residue (9.29 g). The residue was dissolved in a small amount of methanol and isopropanol was added. The first crop (2.0 g) crystallized out of isopropanol as the methanol was evaporated. The crystals were collected and dried to yield 2.0 g (13%) of solid, mp 80°–83° C.

Analysis: Calc. for $C_6H_{10}N_2O_3S_2 \cdot 0.5H_2O \cdot 0.5C_3H_8O$: C, 34.47; H, 5.79; N, 10.72; Found: C, 34.15; H, 5.09; N, 11.59.

EXAMPLE 107

Sulfamic acid 3-[4-[bis(4-fluorophenyl)hydroxymethyl]-1-piperidinyl]propyl ester hydrochloride acetic acid ethyl ester (2:2:1).

To a stirred cooled (ice-acetone bath) solution of 15 ml (0.172 mole) of chlorosulfonyl chloride in 100 ml of acetonitrile was added dropwise a solution of 3.2 g (0.177 mole) of water in 25 ml of acetonitrile at such a rate that the temperature did not exceed 0° C. (45 min). After the addition was completed, the mixture was stirred at −5° C. for 15 min and then treated dropwise with a solution of 18.1 g (0.050 mole) of α,α-bis(4-fluorophenyl)-1-(3-hydroxypropyl-4-piperidine methanol and 20.2 g (0.20 mole) of triethylamine in 150 ml of acetonitrile in 75 ml of methylene chloride at such a rate that the temperature did not exceed 0° C. The ice-acetone bath was removed and the mixture stirred for 2 hr and treated with 150 ml of water, stirred vigorously for 5 min and the layers were separated. The organic layer was concentrated under reduced pressure and the residue partitioned between ethyl acetate and water. The ethyl acetate layer was washed with water and brine, dried (sodium sulfate) and concentrated under reduced pressure to give a white solid. $^1$H NMR showed the solid to be the hydrochloride. The solid was crystallized successively from tetrahydrofuran and then ethyl acetate to yield 4.3 g (18%) of the title compound, mp 78°–81° C.

Analysis: Calculated for $C_{23}H_{30}F_2N_2O_5S \cdot HCl \cdot 0.5C_4H_8O_2$: C, 53.02; H, 6.00; N, 5.38; Found: C, 52.93; H, 6.09; N, 5.20.

EXAMPLE 108

Sulfamic acid 3-cyanophenyl ester.

Using the procedure described in Example 84, the title compound was prepared in 85% yield from 10.3 g (0.086 mole) of 3-cyanophenol and 8.3 ml (0.086 mole) of chlorosulfonyl isocyanate in 75 ml of toluene as a white solid, mp 101°–104° C. (benzene-acetonitrile).

Analysis: Calculated for $C_7H_6N_2O_3S$: C, 42.42; H, 3.05; N, 14.13; Found: C, 42.52; H, 2.82; N, 14.13.

EXAMPLE 109

Sulfamic acid 3-phenylphenyl ester.

Using the procedure described in Example 84, the title compound was prepared from 17.0 g (0.010 mole) of 3-phenyphenol and 9.1 ml (0.105 mole) of chlorosulfonyl isocyanate in 100 ml of toluene to obtain 19.0 g (77%) of white flakes, mp 197°–199° C. (benzene-acetonitrile).

Analysis: Calculated for $C_{12}H_{11}NO_3S$: C, 57.82; H, 4.45; N, 5.62; Found: C, 57.60; H, 4.51; N, 5.59.

EXAMPLE 110

Methylsulfamic acid 2-phenoxy-1,3-propanediyl ester.

To a stirred solution of 16.8 g (0.1 mole) of 2-phenoxy-1,3-propanediol (Preparation 27) in 100 ml of methylene chloride was added, dropwise and simultaneously 35.8 g (0.276 mole) of methylsulfamoyl chloride (Preparation 24) and 36.0 g (0.278 mole) of diisopropylethylamine over a 30 min period. The reaction mixture was stirred for 3 hr, the solvent evaporated under reduced pressure, and the residue was partitioned between ethyl acetate and 2N hydrochloric acid solution (250 ml each). The layers were separated and the organic layer was washed successively with two 250 ml portions of 2N hydrochloric acid and then 250 ml of water, dried, and the solvent was evaporated under reduced pressure to give 45.3 g of a dark, viscous residue. The residue was triturated with ethyl acetate and filtered. The filtrate was evaporated under reduced pressure to give a brown, viscous oil which was purified by column chromatography (4.5×90 cm glass column; 450 g of silica, methylene chloride acetone 100:3). Fractions containing the product were evaporated under reduced pressure and the viscous residue was twice purified by high pressure liquid chromatography (Waters Associates Prep LC/System 500A, PrePAK 500/silica; ethylacetate-hexanes, 1:2 and then methylene chloride-acetone, 100:3; flow rate 150 ml/min). Fractions containing the product were combined and the solvents evaporated under reduced pressure to yield 3.5 g (10%) of the title compound as a colorless, viscous oil.

Analysis: Calculated for $C_{11}H_{18}N_2O_7S_2$: C, 37.28;H, 5.12;N, 7.90: Found: C, 37.66;H, 5.49;N, 8.03.

EXAMPLE 111

Sulfamic acid 3-(1H-imidazol-1-yl)phenyl ester monohydrochloride.

A solution of 3(1H-imidazol-1-yl)phenol (8 g, 0.05 mole) in acetonitrile was treated in an ice bath with sulfamoyl chloride generated from 0.075 mole of chlorosulfonyl isocyanate (Preparation 21) followed by 0.075 mole of triethylamine. After stirring overnight at room temperature, TLC, and $^1H$ NMR of a sample showed starting material still present. The reaction was then treated with another 0.075 mole each of sulfamoyl chloride and triethylamine for another night.

The reaction mixture was then concentrated and neutralized with both solid sodium bicarbonate and its solution. The slightly basic mixture was concentrated again to remove of the last trace of acetonitrile. The resultant solid suspension was chilled and then filtered. The sticky solid was dissolved in acetonitrile, stirred with sodium sulfate, magnesium sulfate and charcoal. The mixture was filtered and the filtrate was concentrated to obtain 9.24 g of oil. This oil was dissolved in acetonitrile/isopropyl alcohol, filtered, and acidified with a solution of hydrogen chloride in isopropyl alcohol. Some isopropyl ether was added to precipitate more solid. The solid was collected, weighed (4.63 g) and recrystallized from methanol/isopropyl alcohol to give 4.3 g of solid, mp 164°-165° C.

Analysis: Calculated for $C_9H_9N_3O_3S \cdot HCl$: C, 39.21;H, 3.66;N, 15.24: Found: C, 38.92;H, 3.82;N, 14.80.

EXAMPLE 112

Sulfamic acid 3-iodophenyl ester.

This compound was prepared using the procedure of Example 84 from 27.8 g (0.126 mole) of 3-iodophenol and 11.7 ml (0.135 mole) of chlorosulfonyl isocyanate in 100 ml of toluene to obtain 29.4 g (78%) of the title compound as white flakes, mp 106°-108° C. (benzene).

Analysis: Calculated for $C_6H_6INO_3S$: C, 24.10;H, 2.02;N, 4.68: Found: C, 23.94;H, 2.02;N, 4.75.

EXAMPLE 113

Dimethylsulfamic acid phenyl ester.

This compound was prepared by the procedure of Example 61. Thus, a solution of 18.8 g (0.2 mol) of phenol and 29.0 ml (0.27 mol) of dimethylsulfamoyl chloride (Aldrich) in 150 ml of toluene gave a viscous oil. The oil was purified by high pressure liquid chromatography (Waters Associates Prep LC/System 500A; PrepPAK 500/silica; ethyl acetate-hexanes, 1:25; flow rate 150 ml/min). Fractions containing the product were combined, the solvents evaporated under reduced pressure, and the viscous residue was dissolved in 500 ml of ethyl ether. The solution was washed successively with three 250 ml portions of a 20% sodium hydroxide solution, 300 ml of water and dried (magnesium sulfate). The solvent was evaporated under reduced pressure to give 10.8 g of a liquid. $^{13}C$ NMR indicated that dimethyl-sulfamoyl chloride was present. Hence the liquid was again purified by high pressure liquid chromatography (Waters Associates Prep LC/System 500A; PrePAK 500/silica; ethyl acetate-hexanes, 1:20; flow rate 100 ml/min). Fractions containing the product were combined and the solvents evaporated under reduced pressure to yield 6.5 g (16%) of the title compound as a colorless liquid.

Analysis: Calculated for $C_8H_{11}NO_3S$: C, 47.75;H, 5.51;N, 6.96: Found: C, 47.49;H, 5.47;N, 6.88.

EXAMPLE 114

Sulfamic acid 4-methylphenyl ester.

This compound was prepared by the procedure used in Example 84. Thus, a solution of 10.8 g (0.1 mole) of 4-methylphenol and 14.8 g (0.105 mole) of chlorosulfonyl isocyanate (95%, Aldrich) in 100 ml of toluene gave 10.3 g (55%) of the title compound as a white solid, mp 80°-82° C. (benzene-petroleum ether, 30°-60° C.).

Analysis: Calculated for $C_7H_9NO_3S$: C, 44.91;H, 4.85;N, 7.48: Found: C, 44.91;H, 4.81;N, 7.40.

EXAMPLE 115

Sulfamic acid 3-(1,1-dimethylethyl)phenyl ester.

This compound was prepared according to the procedure used in Example 84. Thus, 15.0 g (0.1 mole) of 3-t-butylphenol (99%, Aldrich) and 14.8 g (0.105 mole) of chlorosulfonyl isocyanate (95%, Aldrich) in 150 ml of xylene gave 13.3 g of a viscous oil that solidified upon standing. The solid was recrystallized from benzene-petroleum ether 3(0°-60° C.) to give 9.5 g (41%) of the title compound as a white solid, mp 78°-81° C.

Analysis: Calculated for $C_{10}H_{15}NO_3S$: C, 52.38;H, 6.59;N, 6.11: Found: C, 52.46;H, 6.61;N, 6.08.

EXAMPLE 116

Sulfamic acid 3,5-dichlorphenyl ester.

The procedure used in Example 84 was used to prepare this compound from a mixture of 16.3 g (0.10 mole) of 3,5-dichlorophenol and 9.1 ml (0.105 mole) of chlorosulfonyl isocyanate in 75 ml of toluene. The compound was obtained in 83% yield as a white, fluffy solid, mp 146°-147° C. (benzene).

Analysis: Calculated for $C_6H_5Cl_2NO_3S$: C, 29.77;H, 2.08;N, 5.77: Found: C, 29.78;H, 2.05;N, 5.76.

EXAMPLE 117

Sulfamic acid 2,3-dichlorophenyl ester.

This compound was prepared according to the procedure of Example 84. Thus, a mixture of 16.3 g (0.10 mole) of 2,3-dichlorophenol and 9.1 ml (0.105 mole) of chlorosulfonyl isocyanate in 75 ml of toluene gave 17.4 g (72%) of the title compound as an off-white solid, mp 116°-117° C. (benzene).

Analysis: Calculated for $C_6H_5Cl_2NO_3S$: C, 29.77;H, 2.08;N, 5.77: Found: C, 29.88;H, 2.03;N, 5.77.

EXAMPLE 118

Sulfamic acid 4-cyanophenyl ester.

This compound was prepared by the procedure of Example 84 from a solution of 11.9 g (0.10 mole) of 4-cyanophenol (Aldrich Chemical Co.) and 9.1 ml (0.105 mole) of chlorosulfonyl isocyanate in 75 ml of toluene. The solid product was recrystallized from benzene-acetonitrile to give 10.1 g (51%) of white solid, mp 154°-156° C.

Analysis: Calculated for $C_7H_6N_2O_3S$: C, 42.42;H, 3.05;N, 14.13: Found: C, 42.36;H, 2.99;N, 14.10.

EXAMPLE 119

Sulfamic acid 4-methoxyphenyl ester.

This compound was prepared according to the procedure used in Example 84. Thus, a solution of 12.4 g (0.1 mole) of 4-methoxyphenol (Aldrich) and 14.8 g (0.105 mole) of chlorosulfonyl isocyanate (95%, Aldrich) in 100 ml of toluene gave a viscous, oily residue. The oil was purified by high pressure liquid chromatography (Waters Associates Prep LC/System 500A, PrepPAK 500/silica, methylene chloride; flow rate 200 ml/min). Fractions containing the product were combined and the solvent evaporated under reduced pressure to yield 9.6 g of a viscous oil that solidified upon standing. The solid was recrystallized from benzene-petroleum ether (30°-60° C.) to give 7.9 g (39%) of the title compound as a white solid, mp 62°-64° C.

Analysis: Calculated for $C_7H_9NO_4S$: C, 41.37;H, 4.46;N, 6.89: Found: C, 41.49;H, 4.47;N, 7.05.

EXAMPLE 120

Sulfamic acid 3(4-methyl-1H-imidazol-1-yl)phenyl ester hydrochloride.

Following the procedure of Example 82, the title compound was prepared from 8.7 g (0.05 mole) of 3(4-methyl-1H-imidazol-1-yl)phenol in 66% yield, mp 202°-204° C. (methanol-isopropyl ether).

Analysis: Calculated for $C_{10}H_{11}N_3O_3S.HCl$: C, 41.46;H, 4.18;N, 14.50: Found: C, 41.35;H, 4.22;N, 14.35.

EXAMPLE 121

Sulfamic acid 2-methoxyphenyl ester.

This compound was prepared according to the procedure of Example 69. Thus, a solution of 12.4 g (0.1 mole) of 2-methoxyphenol (Guaiacol; Aldrich), 40 ml (0.45 mole) of chlorosulfonyl isocyanate (98%; Aldrich), 7.4 g (0.41 mole) of water, and 59.0 g (0.46 mole) of diisopropylethylamine (99%, Aldrich) in 200 ml of acetonitrile and 100 ml of methylene chloride gave 9.0 g of a viscous oil. The oil was purified by high pressure liquid chromatography (Waters Associates Prep LC/System 500A; PrePAK 500 silica; methylene chloride; flow rate 150 ml/min). Fractions containing the product were combined and the solvents evaporated under reduced pressure to give 4.3 g (21%) of a viscous oil that solidified upon standing. The solid was recrystallized from benzene-petroleum ether (30°-60° C.) to give the title compound as white needles, mp 83°-85° C.

Analysis: Calculated for $C_7H_9NO_4S$: C, 41.37;H, 4.46;N, 6.89: Found: C, 41.30;H, 4.47;N, 6.84.

EXAMPLE 122

(S)-(−)-Sulfamic acid 2-[(aminosulfonyl)oxy]-3-(2-methoxyphenoxy)propyl ester.

A slurry of 5.94 g (0.03 mole) of R-(−)-glycerol guaiacolate (Preparation 33) in 35 ml of methylene chloride was treated by simultaneous addition of a solution of sulfamoyl chloride (0.083 mole) in acetonitrile (15 ml) and diisopropylethylamine (10.75 g, 0.083 mole) in methylene chloride (10 ml) over a 45 min period. The reaction was complete in 1.5 hr. The reaction mixture was washed twice with 100 ml portions of water and the organic layer was chromatographed on silica gel, eluting with 10% methanol in methylene chloride. The desired fractions were combined and concentrated to give 5.6 g (51%) of the title compound as a white powder, mp 136.0°-138.0° C., $[\alpha]_D^{22}$ −4.75° (c=2 in MeOH).

Analysis: Calculated for $C_{10}H_{16}N_2O_8S_2$: C, 33.70;H, 4.53;N, 7.86: Found: C, 33.48;H, 4.62;N, 7.77.

EXAMPLE 123

(R)-(+)-Sulfamic acid 2-[(aminosulfonyl)oxy]-3-(2-methoxyphenoxy)propyl ester.

This compound was prepared by the procedure used in Example 122. A combination of 5.94 g (0.03 mole) of S-(+)glycerol guaiacolate, 0.083 mole of sulfamoyl chloride, and 10.8 g (0.083 mole) of diisopropylethylamine gave 4.5 g (41%) of the title compound as a white powder, mp 137.5°-139.0° C. $[\alpha]_D^{22}$ +4.80° (C=2 in MeOH).

Analysis: Calculated for $C_{10}H_{16}N_2O_8S_2$: C, 33.70;H, 4.53;N, 7.86: Found: C, 33.66;H, 4.69;N, 7.76.

EXAMPLE 124

Sulfamic acid 2,6-dichlorophenyl ester.

This compound was prepared according to the procedure of Example 84 from a mixture of 16.3 g (0.10 mole) of 2,6-dichlorophenol and 9.1 ml (0.105 mole) of chlorosulfonyl isocyanate in 75 ml of toluene to obtain 17.3 g (71%) of the title compound after recrystallization from benzene, mp 114.5°-116° C.

Analysis: Calculated for $C_6H_5Cl_2NO_3S$: C, 29.77;H, 2.08;N, 5.77: Found: C, 29.62;H, 2.05;N, 5.81.

EXAMPLE 125

Sulfamic acid 3-methylphenyl ester.

A solution of 0.25 mole of sulfamoyl chloride in 60 ml of acetonitrile was prepared according to the procedure of Example 20. The solution was chilled (ice-water bath) and treated dropwise with a solution of 10.8 g (0.10 mole) of 3-methylphenol and 29.7 g (0.23 mole) of diisopropylethylamine in 100 ml of acetonitrile at such a rate that the temperature did not exceed 15° C. The solution was stirred at ambient temperature overnight and then diluted with 200 ml of ethyl acetate and 50 ml of water. The layers were separated and the organic layers washed successively with two 50 ml portions of water, 50 ml of 2N hydrochloric acid solution, 50 ml of water, brine, and dried (sodium sulfate) and concentrated to give a brown gum. The gum was purified by column chromatography (400 g silica gel eluted with methylene chloride). The appropriate fractions were combined and concentrated to give a solid residue which was recrystallized from benzene to yield 9.2 g (48%) of the title compound as white plates, mp 84°-85° C. (reported mp 88° C., Chem. Ber. 105, 2791-2799 (1972)).

Analysis: Calculated for $C_7H_9NO_3S$: C, 44.91; H, 4.84; N, 7.48; Found: C,44.77; H, 4.88; N, 7.53.

EXAMPLE 126

Sulfamic acid 3(4-phenyl-1H-imidazol-1-yl)phenyl ester hydrochloride.

Using the same procedure of Example 82, 9.36 g (0.04 mole) of 3(4-phenyl-1H-imidazol-1-yl)phenol was converted to the title compound in 60% yield, mp 209°-211° C.

Analysis: Calculated for $C_{15}H_{13}N_3O_3S.HCl$: C, 51.21; H, 4.01; N, 11.94; Found: C, 51.17; H, 3.99; N, 11.82.

EXAMPLE 127

Sulfamic acid 3-fluorophenyl ester.

To a cooled (ice bath) solution of 11.2 g (0.1 mole) of 3-fluorophenol (98%, Aldrich) in 75 ml of toluene was added 9.1 ml (14.8 g, 0.105 mol) of chlorosulfonyl isocyanate, and the solution heated at reflux overnight. The solution was cooled and cautiously treated dropwise with water until carbon dioxide evolution ceased. An oil separated and ethyl acetate was added to dissolve this oil. The layers were separated and the organic layer was washed with water, dried (sodium sulfate) and concentrated to give an oil which gradually crystallized. The solid was purified by column chromatography on 400 g of silica gel eluted with methylene chloride. The appropriate fractions were combined and concentrated to yield 9.2 g (48%) of the title compound which was recrystallized from benzene to give a white solid, mp 53°-55° C.

Analysis: Calculated for $C_6H_6FNO_3S$: C, 37.70; H, 3.16; N, 7.33; Found: C, 37.70; H, 3.08; N, 7.35.

EXAMPLE 128

Sulfamic acid 3,5-bis(trifluoromethyl)phenyl ester.

This compound was prepared using the procedure of Example 84 from a mixture of 9.8 g (0.043 mole) of 3,5-bis(trifluoromethyl)phenol and 3.9 ml (0.095 mole) of chlorosulfonyl isocyanate in 50 ml of toluene. The solid product was recrystallized from benzene to yield 6.4 g (48%) of a pale yellow solid; mp 118°-120° C.

Analysis: Calculated for $C_8H_5F_6NO_3S$: C, 31.08; H, 1.63; N, 4.53; Found: C, 31.11; H, 1.52; N, 4.60.

EXAMPLE 129

Sulfamic acid 3,5-difluorophenyl ester.

Using the procedure of Example 84, the title compound was prepared using a mixture of 9.9 g (0.076 mole) of 3,5-difluorophenol and 7.0 ml (0.08 mole) of chlorosulfonyl isocyanate in 50 ml of toluene. The solid product was recrystallized from benzene to yield 11.7 g (74%) of white solid, mp 85°-88° C.

Analysis: Calculated for $C_6H_5F_2NO_3S$: C, 34.45; H, 2.41; N, 6.70; Found: C, 34.53; H, 2.34; N, 6.79.

EXAMPLE 130

Sulfamic acid 4-fluorophenyl ester.

Using the procedure of Example 84, a mixture of 11.2 g (0.1 mole) of 4-flurophenol and 9.1 ml (0.105 mole) of chlorosulfonyl isocyanate in 50 ml of toluene gave, after recrystallization from benzene, 15.0 g (79%) of the title compound as a white solid, mp 82.5°-85.5° C.

Analysis: Calculated for $C_6H_6FNO_3S$: C, 37.70; H 3.16; N, 7.33; Found: C, 37.83; H, 3.11; N, 7.37.

EXAMPLE 131

Sulfamic acid 2-[3(1H-imidazol-1-yl)phenoxy]ethyl ester hydrochloride.

A solution of sulfamoyl chloride (0.0275 mole) in 60 ml of acetonitrile was treated dropwise with a solution of 5.1 g (0.025 mole) of 2-[3(1H-imidazol-1-yl)phenoxy]ethanol in 100 ml of acetonitrile. The mixture was stirred at ambient temperature under nitrogen for 20 hr. The mixture was concentrated under vacuum, and the residue was partitioned between ethyl acetate and dilute potassium carbonate solution. The organic fraction was again concentrated under vacuum to a crystalline residue. This residue was dissolved in warm 95% ethanol and treated with 1 equivalent of anhydrous hydrogen chloride. The solution was chilled and the precipitate was collected and dried to give 4.0 g (50%) of the title compound as a pinkish powder, mp 149.0°-150.0° C.

Analysis: Calculated for $C_{11}H_{13}N_3O_4S \cdot HCl$: C, 41.32; H, 4.41; N, 13.14; Found: C, 41.25; H, 4.50; N, 12.92.

EXAMPLE 132

Sulfamic acid 3-(2-methoxyphenoxy)propyl ester.

A solution of 13.0 g (0.071 mole) of 3-(2-methoxyphenoxy)-1-propanol (prepared in 68% yield from guaiacol (43.2 g, 0.35 mole), 3-bromo-1-propanol (89.3 g, 0.61 mole) and potassium carbonate (112.0 g, 0.81 mole) in 1 l of acetone and 9.0 g (0.089 mole) of triethylamine in 50 ml of methylene chloride was added dropwise (20 min.) to a stirred, cooled (ice-acetone bath) solution of 22 ml (0.0786 mole) of sulfamoyl chloride (3.57M solution in acetonitrile, Preparation 20) in 30 ml methylene chloride at such a rate the temperature was maintained at $\leq 12°$ C. The reaction mixture was stirred at ambient temperature for 3 hr. The solvents were evaporated under reduced pressure and the viscous residue was triturated with 300 ml of ethyl acetate and the solids removed by filtration. The filtrate was washed with three 300 ml portions of water, dried (magnesium sulfate) and the solvent evaporated under reduced pressure to yield 11.7 g (63%) of a colorless, viscous oil that solidified upon standing. The solid was recrystallized from methylene choride-petroleum ether (30°-60° C.) to give 6.9 g (37%) of the title compound as a white solid, mp 80°-83° C.

Analysis: Calculated for $C_{10}H_{15}NO_5S$: C, 45.97; H, 5.79; N, 5.36; Found: C, 45.85; H, 5.85; N, 5.28.

EXAMPLE 133

Methylsulfamic acid 2-methoxyphenyl ester.

A solution of 12.4 g (0.1 mole) of 2-methoxyphenol (guaiacol; Aldrich) and 13.1 g (0.1 mole) of methylsulfamoyl chloride (Preparation 20) in 150 ml of toluene was stirred and treated at reflux for 2 hr. The solvent was evaporated under reduced pressure and the only residue was purified by high pressure liquid chromatography (Waters Associates Prep LC/System 500A, Pre-PAK 500A silica, ethyl acetate-hexanes, 1:2; flow rate 150 ml/min). Fractions containing the product were combined and the solvents evaporated under reduced pressure to yield an oil that solidified upon standing. The solid was recrystallized from benzene-petroleum ether (30°-60° C.) to give 14.3 g (66%) of the title compound as a white solid, mp 68°-71° C.

Analysis: Calculated for $C_8H_{11}NO_4S$: C, 44.23; H, 5.10; N, 6.45; Found: C, 44.09; H, 5.12; N, 6.41.

EXAMPLE 134

Sulfamic acid 1,1-dimethyl-2-phenoxy ethyl ester.

To a chilled (ice-water bath) solution of 30 ml (0.11 mole) of 3.57M sulfamoyl chloride solution (Preparation 20) in 50 ml of acetonitrile was added dropwise a solution of 0.10 mole of 1,1'-dimethyl-2-phenoxyethanol and 0.229 mole of triethylamine in 20 ml of acetonitrile at such a rate as to maintain a temperature less than 15° C. The mixture was then stirred for 3 hr at ambient temperature, filtered, and concentrated to an oil that was purified by preparative high pressure liquid chromatography.

EXAMPLE 135

Sulfamic acid 2-[4-[(1H-imidazol-1-yl)phenoxy]ethyl ester hydrochloride].

A stirred mixture of 8.0 g (0.050 mole) of 4(1H-imidazol-1-yl)phenol, 13.5 ml (0.20 mole) of 2-chloroethanol and 28 g (0.2 mole) of potassium carbonate in 200 ml of methyl ethyl ketone was heated at reflux, filtered, and concentrated to obtain 5.1 g of 2-[4-(1H-imidazol-1-yl)phenoxy]ethanol (50%). This alcohol (0.25 mole) and 5.2 g (0.030 mole) of sulfamic acid phenyl ester (Example 39) in 100 ml of dioxane was heated at reflux for 20 minutes, concentrated and the residual solid triturated in acetone. The triturant was acidified with an anhydrous solution of hydrogen chloride in isopropyl alcohol and the solid hydrochloride collected by filtration. The product was recrystallized from isopropyl alcohol-isopropyl ether to yield 4.26 g of solid, mp 156°-157° C.

Analysis: Calculated for $C_{11}H_{13}N_3O_4S \cdot HCl$: C, 41.32; H, 4.41; N, 13.14; Found: C, 41.60; H, 4.62; N, 12.87.

EXAMPLE 136

Methylsulamic acid 3-(2-hydroxyphenoxy)-2-[[(methylamino) sulfonyl]oxy]propyl ester (a) Methylsulfamic acid 2-[[(methylamino)sulfonyl]oxy]-3-[2-(phenylmethoxy)phenoxy]propyl ester.

To a solution of 21.4 g (0.165 mol) of methylsulfamoyl chloride in 100 ml of $CH_2Cl_2$ was added dropwise a solution of 20.6 g (0.075 mol) of 3-[2-(phenylmethoxy)phenoxy]-1,2-propanediol (J. Pharm. Sci. 52:995–998, 1963) and 21.3 g (0.165 mole) of diisopropylethylamine in 250 ml of methylene chloride, and the solution was stirred at ambient temperature overnight. The solution was washed successively with 150 ml of water, twice with 150 ml of 2N hydrochloric acid, 150 ml of water, 150 ml of dilute sodium bicarbonate solution, and 150 ml of brine, dried ($Na_2SO_4$), and concentrated to give a solid residue. The solid was recrystallized from 2-propanol (charcoal) to yield 19.2 g (56%) of white solid, mp 95°-97.5° C.

Analysis: Calculated for $C_{18}H_{24}N_2O_8S_2$: C, 46.95; H, 5.25; N, 6.08; Found: C, 47.00; H, 5.40; N, 6.04.

(b) Title Compound

A solution of 9.2 g (0.02 mole) of the compound of part a in 250 ml of ethyl acetate was hydrogenated in a Parr apparatus over 0.25 teaspoon of 5% Pd/C at 50° C. overnight. No hydrogen was used so the catalyst was removed by filtration, fresh catalyst added, and the mixture hydrogenated at 60° C. overnight. Again, no hydrogen was used so the catalyst was removed, and 0.25 teaspoon of 10% Pd/C was added and the mixture hydrogenated at 60°. Hydrogen uptake ceased after 1 hr. The mixture was cooled, filtered, and the filtrate concentrated to give a gum. This gum was purified by column chromatography (150 g of silica gel eluted with 0–10% acetone in methylene chloride). The appropriate fractions were combined and concentrated to give a gum which eventually crystallized. The solid was triturated with petroleum ether (30°-60° C.), collected by filtration, and dried to yield 6.8 g (92%) of title compound white solid, mp 87°-90° C.

Analysis: Calculated for $C_{11}H_{18}N_2O_8S_2$: C, 35.67; H, 4.90; N, 7.56; Found: C, 35.64; H, 4.96; N, 7.61.

EXAMPLE 137

(S)-(−)-Methylsulfamic acid 3-(2-methoxyphenoxy)-2-[[(methylamino)sulfonyl]-oxy]propyl ester.

A slurry of 6.6 g (0.033 mole) of R-(−)glyceryl guaiacolate in 40 ml of methylene chloride was treated with simultaneous addition of solutions of methylsulfamoyl chloride (9.3 g, 0.072 mole) in 13 ml of methylene chloride and diisopropylethylamine (9.3 g, 0.072 mole) in 9 ml of methylene chloride over a period of 0.5 hr. The solution was stirred for an additional 2 hr, then chromatographed on silica gel, eluting with 3% THF in methylene chloride. Concentration of the desired fractions gave an oil which crystallized on standing. The solid mass of crystals was recrystallized from a combination of n-propanol and isopropyl ether to give 10.2 g (80%) of the title compound as a white powder, mp 50.0–51.5° C., $[\alpha]^{22}D = -5.3°$ (c=1, MeOH).

Analysis: Calculated for $C_{12}H_{20}N_2O_8S_2$: C, 37.49; H, 5.24; N, 7.29; Found: C, 37.55; H, 5.34; N, 7.28.

EXAMPLE 138

(R)-(+)-Methylsulfamic acid 3-(2-methoxyphenoxy)-2-[[(methylamino)sulfonyl]-oxy]propyl ester.

This compound was prepared by the procedure of Example 137. A mixture of 3.96 g (0.02 mole) of S-(+)-glyceryl guaiacolate, 5.70 g (0.033 mole) of methylsulfamoyl chloride, and 5.7 g (0.044 mole) of diisopropylethylamine gave, after chromatography and recrystallization, 5.0 g (65%) of white powder, mp 50.5°-52.0° C., $[\alpha]^{22}D = +5.3°$ (c=1, MeOH).

Analysis: Calculated for $C_{12}H_{20}N_2O_8S_2$: C, 37.49; H, 5.24; N, 7.29; Found: C, 37.46; H, 5.32; N, 7.27.

EXAMPLE 139

Sulfamic acid 3-[4-(1H-imidazol-1-yl)phenoxy]propyl ester.

A solution of 9.0 g (0.041 mole) of 3-[4-(1H-imidazol-1-yl)phenoxy]propanol in 150 ml of acetonitrile was treated with a solution of one equivalent of sulfamoyl chloride in 13 ml of acetonitrile. The mixture was stirred for 20 hr. The reaction mixture was concentrated under vacuum and the residue was dissolved in water. The aqueous solution was filtered and the filtrate was basified to pH 8 with potassium carbonate. The mixture was extracted with ethyl acetate. The organic fraction was concentrated under a stream of nitrogen and the precipitate was collected and dried to give 5.2 g (43%) of tan powder, mp 105.0°-106.0° C.

Analysis: Calculated for $C_{12}H_{15}N_3O_4S$: C, 48.48; H, 5.09; N, 14.13; Found: C, 48.73; H, 5.12; N, 13.95.

EXAMPLE 140

Sulfamic acid 2-[3-(2-methyl-1H-imidazol-1-yl)phenoxy]ethyl ester.

A mixture of 17.4 g (0.10 mole) of 3-(2-methyl-1H-imidazol-1-yl)phenol, 40.2 g (0.50 mole) of chloroethanol and 70 g (0.5 mole) of potassium carbonate in 100 ml of methyl ethyl ketone was heated at reflux for 30 hr. The reaction mixture was filtered and the filtrate was concentrated. The residue was partitioned between ethyl acetate and dilute potassium carbonate solution. The organic layer was concentrated and chromatographed on silica gel to give 7 g of desired product of approximately 90% purity. This intermediate was sulfamoylated by treatment in 150 ml of acetonitrile with 1.3 equivalents of sulfamoyl chloride in 13 ml of acetonitrile and 1 g of diisopropylethyl amine. When HPLC indicated all starting material was consumed, the reaction mixture was quenched with water, then concentrated to a syrup. The syrup was partitioned between ethyl acetate and dilute potassium carbonate solution. The organic layer was concentrated and chromatographed on silica gel. The fractions containing desired product were combined and concentrated. The syrup (3.0 g) was dissolved in 40 ml of 2-propanol and treated with 1 equivalent of anhydrous hydrogen chloride. The precipitate was collected and dried to give 2.8 g (9.4%) of an off-white powder. This material was recrystallized from 95% ethanol to give 1.9 g of tan-yellow, monohydrochloride crystals, mp 184°–186° C.

Analysis: Calculated for $C_{12}H_{15}N_3O_4S \cdot HCl$: C, 43.18; H, 4.83; N, 12.59; Found: C, 43.36; H, 4.90; N, 12.41.

EXAMPLE 141

Sulfamic acid 2-[4-(1H-1,2,4-triazol-1-yl)phenoxy]ethyl ester.

A solution of 8.2 g (0.04 mole) of 2-[4-(1H-1,2,4-triazol-1-yl)phenoxyl]ethanol in 100 ml of acetonitrile was treated with a solution of 1.3 equivalents of sulfamoyl chloride in 19 ml of acetonitrile. One equivalent, 5.2 g (0.04 mole) of diisopropylethylamine was also added in one portion. The mixture was stirred for 2 hr. The precipitate was collected and partitioned between ethyl acetate and a dilute potassium carbonate solution. The organic layer was separated and concentrated to a white powder. The powder was triturated with ethyl ether, collected and dried to give 6.3 g (55%) of white powder, mp 134°–136° C.

Analysis: Calculated for $C_{10}H_{12}N_4O_4S$: C, 42.25; H, 4.26; N, 19.71; Found: C, 42.39; H, 4.31; N, 19.41.

EXAMPLE 142

Sulfamic acid 2-[3-(4-methyl-1H-imidazol-1-yl)phenoxy]ethyl ester.

By the same procedure Example 111, 2-[3-(4-methyl-1H-imidazol-1-yl)phenoxy]ethanol monohydrochloride was first converted to its free base and then to the monohydrochloride in 51% overall yield, mp 169°–170° C.

Analysis: Calculated for $C_{12}H_{0.5}N_3O_4S \cdot HCl$: C, 43.18; H, 4.83; N, 12.59; Found: C, 42.74; H, 4.87; N, 12.38.

EXAMPLE 143

Sulfamic acid 3-(2-methyl-1H-imidazol-1-yl)phenyl ester.

A slurry of 8.7 g (0.05 mole) of 3-(2-methyl-1H-imidazol-1-yl)phenol in 150 ml of acetonitrile was treated with a solution of 0.05 mole of sulfamoyl chloride in 20 ml of acetonitrile. The mixture dissolved and slowly deposited off-white crystals over the period of 24 hr. The precipitate was collected and triturated with hot absolute ethanol. The slurry was cooled and the precipitate was collected and dried to give 4.0 g (32%) of off-white powder, monohydrochloride, mp 197°–200° C.

Analysis: Calculated for $C_{10}H_{11}N_3O_3S \cdot HCl$: C, 41.46; H, 4.18; N, 14.50; Found: C, 41.28; H, 4.22; N, 14.57.

EXAMPLE 144

Sulfamic acid 2-[3-(diethylamino)phenoxy]ethyl ester.

2-(3-Nitrophenoxy)ethanol (13.7 g, 0.075 mole), acetaldehyde (30 ml, 0.52 mole), and 5% Pd-C (1.5 g) in 100 ml methanol and 20 ml ethanol was hydrogenated on a Parr hydrogenator for 3.5 hr whereupon the pressure drop had ceased. The mixture was filtered, and the filtrate concentrated to an oil (18.4 g). This oil was chromatographed on 350 g silica gel eluted with 5% MeOH/$CH_2Cl_2$ to give 8.45 g of an almost colorless oil. $^1H$ NMR supported the structure of 2-(m-diethylaminophenoxy)ethanol of which 7.45 g (0.036 mole) was converted to the title compound by reacting with the sulfamoyl chloride generated by mixing chlorosulfonylisocyanate (0.09 mole) and formic acid (0.09 mole) in acetonitrile as described in Preparation 19. The product free base was isolated by acid-base transfer extractions. The oily free base solidified upon cooling. It was recrystallized twice from toluene and dried under vacuum overnight at room temperature, mp 105°–6° C.

analysis: Calculated for $C_{12}H_{20}N_2O_2S$: C, 49.98; H, 6.99; N, 9.71; Found: C, 49.86; H, 7.09; N, 9.72.

EXAMPLE 145

Sulfamic acid 3-(2-hydroxyethyl)-2-(3-phenoxyphenyl)-4-thiazolidinone ester.

a. 3-(2-hydroxyethyl)-2-(3-phenoxyphenyl)-4-thiazolidinone

A mixture of 15.3 g (0.077 mole) of 3-phenoxybenzaldehyde (Fluka), 4.8 g (0.078 mole) of ethanolamine (99%, Aldrich) and 7.5 g (0.077 mole) of mercaptoacetic acid (95%, Aldrich) in 150 ml of benzene was stirred and heated at reflux temperature overnight utilizing a Dean-Stark trap to remove water. The reaction mixture was poured into a solution of 300 ml of water and 20 ml of concentrated ammonium hydroxide solution. The layers were separated and the organic layer was washed twice with 100 ml portions of 2N hydrochloric acid, twice with 100 ml portions of water, dried (magnesium sulfate) and the solvent evaporated under reduced pressure to give 23.6 g (97%) of the alcohol which was used without further purification.

b. Preparation of the title compound

This compound was prepared by the procedure of Example 28. Thus, 20.0 g (0.063 mole) of 3-(2-hydroxyethyl)-2-(3-phenoxyphenyl)-4-thiazolidinone, 22 ml (247.7 mole) of chlorosulfonylisocyanate (98%, Aldrich), 25.6 g (0.254 mole) of triethylamine, and 4.0 g (0.222 mole) of water in 250 ml of acetonitrile gave 16.0 g of a viscous oil. The oil was purified by chromatography (4.5×90 cm glass column; 500 g of silica gel; methylene chloride, then acetone). Desired fractions were combined and the solvents were evaporated under reduced pressure to give 10.2 g of an oily residue. The oil was triturated with methylene chloride-edthyl ether and the resulting solid was collected by filtration. The solid was recrystallized from methylene chloride-ethyl ether to give 6.1 g (24%) of the title compound as a white solid, mp 108°–111° C.

Analysis: Calculated for $C_{17}H_{18}N_2O_5S_2$: C, 51.76; H, 4.60; N, 7.10; Found: C, 51.90; H, 4.66; N, 7.04.

EXAMPLE 146

Sulfamic acid 2-(methoxycarbonyl)propyl ester.

A mixture of 5.9 g (0.05 mole) of (S)-(+)methyl 3-hydroxy-2-methylpropionate, 9.5 g (0.055 mole) of phenyl sulfamate, 25 ml of toluene and 0.5 g of pyridine was heated at reflux for 2 hr. The reaction solution was concentrated under vacuum, and the residue was chromatographed, using silica gel and eluting with 2% methanol in methylene chloride. The desired fractions were concentrated under vacuum to give 3.9 g (40%) of a pale yellow oil.

Analysis: Calculated for $C_5H_{11}NO_5S$: C, 30.45; H, 5.62; N, 7.10; Found: C, 30.23; H, 5.84; N, 6.95.

EXAMPLE 147

Sulfamic acid (4-chlorophenoxy)-1,3-propanediyl ester.

To a cooled (ice bath) solution of 7.8 ml (12.7 g, 0.09 mole) of chlorosulfonyl isocyanate in 50 ml of acetonitrile was added portionwise a solution of 3.9 g (0.09 mole; a factor of 0.935 was used to compensate for 4% $H_2O$ present) of 96% formic acid in 20 ml acetonitrile at such a rate that the temperature did not exceed 12° C. After the addition was complete, the solution was stirred at ambient temperature for 3 hr, cooled to 10° C., and treated dropwise with a solution of 8.1 g (0.04 mole) of 2-(4-chlorophenoxy)-1,3-propanediol and 13.9 ml (10.3 g, 0.08 mole) of diisopropylethylamine in 75 ml of acetonitrile at such a rate that the temperature did not exceed 15° C. The solution was stirred at ambient temperature overnight and then concentrated. The residue was dissolved in 200 ml of methylene chloride and 50 ml of ethyl acetate, and washed successively with 50 ml portions of water, 2N hydrochloric acid solution (twice), water and dilute sodium bicarbonate, dried (sodium sulfate), and concentrated to give a gum as residue. The gum was purified by column chromatography on 320 g of silica gel using a gradient elution of 0–35% acetone in benzene. The appropriate fractions were combined and concentrated to give a solid. The solid was recrystallized from benzene-acetonitrile to yield 6.7 g (47%) of white solid, mp 133°–134° C.

Analysis: Calculated for $C_9H_{13}Cl_N{_2}O_7S_2$: C, 29.96; H, 3.63; N, 7.76; Found: C. 30.00; H, 3.67; N. 7.76.

EXAMPLE 148

Methylsulfamic acid 2-(4-chlorophenoxy)-1,3-propanediyl ester.

To a solution of 11.7 g (0.09 mole) of freshly distilled methylsulfamoyl chloride in 50 ml of methylene chloride was added dropwise a solution of 8.1 g (0.04 mole) of 2-(4-chlorophenoxy)-1,3-propanediol and 15.6 ml (11.6 g, 0.09 mole) of diisopropylethylamine in 100 ml of methylene chloride. The solution was stirred at ambient temperature for 24 hr and then washed successively with 50 ml portions of water, 2N hydrochloric acid solution (twice), water, dilute aqueous sodium bicarbonate and brine, dried (sodium sulfate), and concentrated to give a gum as residue. The gum was purified by column chromatography on 360 g of silica gel using a gradient elution with 0–20% acetone in benzene. The appropriate fractions were combined and concentrated to yield 13.8 g (88%) of the title compound as a clear gum.

Analysis: Calculated for $C_{11}H_{17}ClN_2O_7S_2$: C, 33.98; H, 4.41; N, 7.20; Found: C, 33.51; H, 4.40; N, 7.31.

EXAMPLE 149

Dimethylsulfamic acid 2-[4-(1H-imidazol-1-yl)phenoxy]ethyl ester.

To a solution of 15.0 g (0.074 mol) of 2-[4-(1H-imidazol-1-yl)phenoxy]ethanol in 100 mL of N,N-dimethylformamide (DMF) was added 3.8 g (0.1 mol) of sodium hydride (60% oil dispersion) portionwise and the mixture was stirred at ambient temperature for 3 h. To this mixture was added 13.7 g (0.1 mol) of dimethylsulfamoyl chloride and the mixture was stirred at ambient temperature overnight. The reaction mixture was poured into 1.2 L of water and its pH was adjusted to 10 with sodium carbonate. The mixture was extracted with three 400-mL portions of ethyl acetate. The combined organic layers were washed twice with 400-mL portions of water, dried (MgSO$_4$), and the solvent was evaporated under reduced pressure to give a viscous residue. The residue was purified by high pressure liquid chromatography (Waters Associates Prep LC/System 500 A; PrepPAK 500 silica; ethyl acetate; flow rate 150 mL/min). Fractions containing the product were combined and the solvent was evaporated under reduced pressure to give the title compound, a viscous oil. The oil was converted to the hydrochloride (2-propanol; ethereal HCl) and the white solid was collected by filtration to yield 5.9 g (26%), mp 120°–123° C.

Analysis: Calc. for $C_{13}H_{17}N_3O_4S$•HCl•$H_2O$: C, 42.68; H, 5.51; N, 11.49; Found: C, 42.84; H, 5.41; N, 11.49.

EXAMPLE 150

Sulfamic acid 4-iodophenyl ester.

This compound was prepared according to the procedure of Example 56. A mixture of 22.0 g (0.1 mole) of 4-iodophenol (Aldrich) and 9.1 ml (14.8 g, 0.105 mole) of chlorosulfonyl isocyanate in 100 ml of toluene gave 23.8 g (80%) of the title compound as a white solid, mp 146°–147° C.

Analysis: Calculated for $C_6H_6INO_3S$: C, 24.10; H, 2.02; N, 4.68; Found: C, 24.07; H, 1.95; N, 4.67.

EXAMPLE 151

Sulfamic acid 3-[2-[(aminosulfonyl)oxy]ethoxy]phenyl ester.

To a stirred solution of 0.59 mole of sulfamoyl chloride[1] in 100 ml of acetonitrile was added dropwise simultaneously 85.3 g (0.66 mole) of diisopropylethylamine (Hunig's base, Aldrich) and a solution of 15.7 g (0.1 mole) of O-(2-hydroxyethyl)resorcinol (98%; Lancaster Synthesis, Windham, N.H. 03087) in 100 ml of acetonitrile (temp. ≦15° C.; 20 min). The reaction mixture was stirred at ambient temperature for 3 hr, the solvent evaporated under reduced pressure and the residue was partitioned between ethyl acetate and water (300 ml each). The organic layer was washed with four 300 ml portions of water (pH neutral to pH paper), dried (sodium sulfate), and the solvent evaporated under reduced pressure to give 17.6 g of a viscous residue. The residue was purified by high pressure liquid chromatography (Waters Associates Prep LC/System 500 A; PrepPAK® 500 silica, methylene chloride-acetone, 10:1, flow rate 150 ml/min.[2] Desired fractions were combined and the solvents evaporated under reduced pressure to give 7.9 g (25%) of an oil that solidified upon standing. The solid was recrystallized from ethyl acetate-benzene to give 4.6 g (15%) of white solid, mp 142°–144° C.

[1] The sulfamoyl chloride was prepared from 52 ml (0.59 mole) of chlorosulfonyl isocyanate (98%, Aldrich) and 10.4 g (0.58 mole) of water in 100 ml of acetonitrile and was used as such.
[2] The residue yielded 3.0 g (12%) of 3-(2-chloroethoxy)phenol sulfamate ester (Example 113).

Analysis: Calculated for $C_8H_{12}N_2O_7S_2$: C, 30.77; H, 3.87; N, 8.97; Found: C, 30.85; H, 3.95; N, 8.92.

EXAMPLE 152

Sulfamic acid 3-methoxyphenyl ester.

This compound was prepared according to the procedure used in Example 42. Thus, a solution of 12.4 g (0.1 mole) of 3-methoxyphenol (Aldrich), 31 ml (0.35 mole) of chlorosufonylisocyanate (98%, Aldrich), 5.7 g (0.32 mole) of water, and 35.9 g (0.36 mole) of triethylamine in 200 ml of acetonitrile gave 8.3 g of a brown, viscous oil. The oil was purified by high pressure liquid chromatography (Waters Associates Prep LC/System 500A; PrepPAK ® 500 silica; methylene chloride; flow rate 150 ml/min). Fractions containing the desired compound were combined and the solvents evaporated under reduced pressure to yield a viscous oil that solidified upon standing. The solid was recrystallized from benzene-petroleum ether (30°–60° C.) to give 3.5 g (17%) of a white solid, mp 59°–61° C.

Analysis: Calculated for $C_7H_9NO_4S$: C, 41.37; H, 4.46; N, 6.89; Found: C, 41.40; H, 4.48, N, 6.85.

EXAMPLE 153

Sulfamic acid 2-fluorophenyl ester.

This compound was prepared according to the procedure of Example 56. A mixture of 11.2 g (0.1 mole) of 2-fluorophenol and 9.1 ml (14.8 g, 0.105 mole) of chlorosulfonyl isocyanate in 50 ml of toluene gave 7.3 g (38%) of the title compound as a white solid, mp 63°–64° (benzene).

Analysis: Calculated for $C_6H_6FNO_3S$: C, 37.70; H, 3.16; N, 7.33; Found: C, 37.63; H, 3.08; N, 7.29.

EXAMPLE 154

Methylsulfamic acid 2-(2-methoxy)ethyl ester.

To a stirred solution of 12.2 g (0.094 mole) of methylsulfamoyl chloride in 100 ml of acetonitrile was added a solution of 12.6 g (0.075 mole) 2-(2-methoxyphenoxy)ethanol and 9.7 g (0.096 mole) of triethylamine (temp. $\leqq 15°$ C.; 15 min). The reaction mixture was stirred at ambient temperature for 2 hr, the solids were removed by filtration, and the filtrate was evaporated under reduced pressure to yield a viscous residue. The residue was partitioned between ethyl ether (500 ml) and water (300 ml). The organic layer was washed twice with 300 ml portions of water, dried (magnesium sulfate) and the solvent evaporated under reduced pressure to yield a viscous oil. The oil was purified by high pressure liquid chromatography (Waters Associate Prep LC/System 500A; PrepPAK ® 500 silica; ethyl acetate-hexanes, 1:2). Fractions containing the desired compound were combined and the solvents evaporated under reduced pressure to give 8.2 g (42%) of a colorless, viscous oil.

Analysis: Calculated for $C_{10}H_{15}NO_5S$: C, 45.97; H, 5.79; N, k5.36; Found: C, 45.57; H, 5.96; N, 5.42.

EXAMPLE 155

Sulfamic acid 3-(2-chloroethoxy)phenyl ester.

This compound was isolated (12% yield; HPLC) as a solid by-product in the preparation of the compound of Example 105. The solid was recrystallized from benzene-petroleum ether (30°–60° C.) to yield a white solid, mp 94°–96° C.

Analysis: Calculated for $C_8H_{10}ClNO_4S$: C, 38.18; H, 4.01; N, 5.57; Found: C, 38.30; H, 4.04; N, 5.53.

EXAMPLE 156

Methylsulfamic acid 2-phenoxyethyl ester.

This compound was prepared according to the procedure used in Example 112. Thus, a mixture of 14.8 g (0.1 mole) of 2-phenoxyethanol (Matheson, Coleman, and Bell), 15.6 g (0.12 mole) of methylsulfamoyl chloride and 12.3 g (0.12 mole) of triethylamine in 150 ml of acetonitrile gave a viscous oil that solidified upon standing. The solid was recrystallized from benzene-petroleum ether (30°–60° C.) to yield 15.4 g (67%) of shiny, white flakes, mp 66°–68° C.

Analysis: Calculated for $C_9H_{13}NO_4S$: C, 46.74; H, 5.67; N, 6.06; Found: C, 46.68; H, 5.75; N, 6.07.

EXAMPLE 157

Sulfamic acid 3-(2-ethoxyphenoxy)-1,2-propanediyl ester.

To a cold (ice bath) solution of 14.8 ml (24.0 g, 0.17 mole) of chlorosulfonyl isocyanate in 75 ml of acetonitrile at 10° C. was added dropwise a solution of 7.3 g (0.17 mole) of 96% formic acid in 25 ml of acetonitrile at such a rate that the temperature did not exceed 15° C. After the addition was complete the mixture was stirred at ambient temperature for 6 hr until gas evolution ceased. The reaction mixture was cooled to 10° C. and treated dropwise with a solution of 15.9 g (0.075 mol) of 3-(2-ethoxyphenoxy)-1,2-propanediol and 26 ml (19.3 g, 0.15 mole) of diisopropylethylamine in 150 ml of acetonitrile while maintaining the temperature at 10°–15° C. The solution was stirred overnight at ambient temperature and then additional diisopropylethylamine was added dropwise until the pH of the solution remained basic for 15 min. The mixture was concentrated under reduced pressure and the residue was dissolved in 250 ml of methylene chloride. The organic layer was washed successively with 50 ml portions of water, 2N hydrochloric acid solution, water, dilute sodium bicarbonate solution, and brine, dried (sodium sulfate), and concentrated to give ~30 g of gum as residue. The gum was purified on 600 g of silica gel eluted with 0–15% acetone in methylene chloride. Appropriate fractions were combined and concentrated to yield 9.1 g (33%) of a white solid, mp 113°–115° (benzene-acetonitrile).

Analysis: Calculated for $C_{11}H_{18}N_2O_8S_2$: C, 35.67; H, 4.90; N, 7.56; Found: C, 35.66; H, 4.98; N, 7.53.

EXAMPLE 158

Sulfamic acid 2-[3-(phenylmethoxy)phenoxy]ethyl ester.

This compound was prepared according to the procedure used in Example 101. Thus, a mixture of 14.7 g (0.06 mole) of 2-(3-benzyloxyphenoxy)ethanol, 17 ml (0.066 mole) of sulfamoyl chloride (3.9M solution in acetonitrile) and 7.0 g (0.069 mole) of triethylamine in 150 ml of acetonitrile gave a viscous, oily residue. The oil was triturated with benzene-petroleum ether (30°–60° C.) and the solid was collected by filtration. The solid was recrystallized from chloroform to yield 8.6 g (44%) of a white solid, mp 107°–109° C.

Analysis: Calculated for $C_{15}H_{17}NO_5S$: C, 55.72; H, 5.30; N, 4.33; Found: C, 55.39; H, 5.26; N, 4.27.

EXAMPLE 159

Methylsulfamic acid 3-[(2-phenylmethoxy)phenoxy]-1,2-propanediyl ester.

To a solution of 21.4 g (0.165 mole) of methylsulfamoyl chloride in 100 ml of methylene chloride was added dropwise a solution of 20.6 g (0.075 mole) of 3-[2-(phenylmethoxy)phenoxy]-1,2-propanediol and 21.3 g (0.165 mole) of diisopropylethylamine in 250 ml of methylene chloride, and the solution was stirred at ambient temperature overnight. The solution was washed successively with 150 ml of water, twice with 150 ml of 2N hydrochloric acid solution, 150 ml of water, 150 ml of dilute sodium bicarbonate solution, and 150 ml of brine, dried (sodium sulfate), and concentrated to give a solid residue. The solid was recrystallized from 2-propanol (charcoal) to yield 19.2 g (56%) of a white solid, mp 95°–97.5° C.

Analysis: Calculated for $C_{18}H_{24}N_2O_8S_2$: C, 46.95; H, 5.25; N, 6.08; Found: C, 47.00; H, 5.40; N, 6.04.

EXAMPLE 160

Sulfamic acid 1,3-phenylene ester.

A solution of 11.0 g (0.1 mole) of resorcinol and 54.4 g (0.54 mole) of triethylamine in 100 ml of acetonitrile was added to a stirred, cooled (acetone-ice bath, ≦12° C.) solution of 150 ml (0.59 mole) of sulfamoyl chloride (3.9M solution in acetonitrile) over a 25 min period, and the mixture was stirred at ambient temperature overnight. The reaction mixture was treated with water (200 ml) and ethyl acetate (400 ml). The organic layer was evaporated under reduced pressure and the residue was partitioned between ethyl acetate (400 ml) and water (300 ml). The organic layer was washed with five 300-ml portions of water (pH neutral to pH paper), dried (magnesium sulfate), and the solvent was evaporated under reduced pressure to give a viscous oil that solidified upon standing. The solid was recrystallized from ethyl acetate-petroleum ether (30°-60° C.) to yield 3.5 g (13%) of white solid, mp 104°-106° C.

Analysis: Calculated for $C_6H_8N_2O_6S_2$: C, 26.86; H, 3.01; N, 10.44; Found: C, 27.09; H, 3.05; N, 10.26.

EXAMPLE 161

Methylsulfamic acid 3-(2-ethoxyphenoxy)-1,2-propanediyl ester.

To a solution of 21.4 g (0.165 mole) of methylsulfamoyl chloride in 100 ml of methylene chloride was added dropwise a solution of 15.9 g (0.075 mole) of 3-(2-ethoxyphenoxy)-1,2-propanediol and 21.3 g (0.165 mole) of diisopropylethylamine in 200 ml of methylene chloride, and the mixture was stirred at ambient temperature overnight. The solution was washed successively twice with 150 ml portions of 2N hydrochloric acid solution, once with a dilute sodium bicarbonate solution and once with brine, dried (sodium sulfate), and concentrated to give ~34 g of gum residue. The gum was purified by column chromatography in 600 g of silica gel eluted with 0-5% acetone in methylene chloride. The appropriate fractions were combined and concentrated to give a gum which gradually crystallized over several days. The solid was triturated with petroleum ether, collected by filtration, and dried to yield 25.0 g (84%) of a white solid, mp 55°-58° C.

Analysis: Calculated for $C_{13}H_{22}N_2O_8S_2$: C, 39.19; H, 5.57; N, 7.03; Found: C, 38.79; H, 5.68; N, 7.19.

EXAMPLE 162

Sulfamic acid 4-(2-methyl-1H-imidazol-1-yl)phenyl ester monohydrochloride.

To a chilled solution of acetonitrile (50 ml) and chlorosulfonyl isocyanate (12.16 g, 0.086 mole) was added benzyl alcohol (9.29 g, 0.086 mole) while maintaining the temperature between 10°-15° C. The reaction stirred at room temperature 1.5 hr and 4-(2-methyl-1H-imidazol-1-yl)phenol (10.0 g, 0.057 mole) added in small portions) while maintaining the temperature below 20° C. The reaction was stirred overnight and its progress checked by thin layer chromatography (8:1:1 ethyl acetate/methanol/ammonium hydroxide). Once the reaction had gone to completion, isopropyl alcohol (3.42 g, 0.057 mole) was added and reaction stirred an additional hour. The solution was concentrated and the residue dissolved in methanol (150 ml) and the solution subjected to catalytic hydrogenation using 5% palladium on carbon catalyst. The solution was filtered and the filtrate concentrated, replacing the methanol with isopropyl alcohol. White crystals precipitated and were collected and dried (9.8 g, 59.5%, mp 197°-200° C.).

Analysis: Calculated for $C_{10}H_{11}N_3O_3S \cdot HCl$: C, 41.46; H, 4.18; N, 14.50; Found: C, 41.19; H, 4.23; N, 14.29.

EXAMPLE 163

Sulfamic acid 2-[4-[2-[(aminosulfonyl)oxy]ethoxy]phenoxy]ethyl ester.

A mixture of 19.8 g (0.1 mole) of hydroquinone bis (2-hydroxyethyl)ether (98%, Aldrich) and 41.4 g (0.41 mole) of triethylamine in 350 ml of acetonitrile was added to a cooled (acetone-ice bath, temp≦15° C.) solution of 130 ml of sulfamoyl chloride solution (3.14M solution in acetonitrile) and 100 ml of acetonitrile. The mixture was mechanically stirred at ambient temperature overnight. The solvent was evaporated under reduced pressure and the residue was partitioned between 400 ml of water and 800 ml of ethyl acetate. The aqueous layer was extracted with two 400 ml portions of ethyl acetate and the combined ethyl acetate extracts (1.61) were washed with two 400 ml portions of water, dried (magnesium sulfate) and the solvent evaporated under reduced pressure to give a viscous residue which was triturated with 100 ml of methylene chloride and let stand at ambient temperature for two days. The resulting solid was collected by filtration and then washed with water until the filtrate was neutral to pH paper and dried (air). The solid was recrystallized from acetonitrile to yield 9.9 g (29%) of a white solid containing a small amount of acetonitrile, mp 162°-164° C.

Analysis: Calculated for $C_{10}H_{16}N_2O_8S_2$: C, 33.70; H, 4.53; N, 7.86; Found: C, 34.30; H, 4.62, N, 8.03.

Analysis: Calc. for $C_{10}H_{16}N_2O_8S_2 \cdot 0.07CH_3CN$: C, 33.90; H, 4.55; N, 8.07.

EXAMPLE 164

Sulfamic acid 2-[4-(phenylmethoxy)phenoxy]ethyl ester.

To a stirred suspension of 30.0 g (0.12 mole) of 4-(benzyloxy)phenoxyethanol in 150 ml of acetonitrile was added simultaneously 59 ml (0.18 mole) of sulfamoyl chloride solution (3.14M solution in acetonitrile) and 19.5 g (0.19 mole) of triethylamine. The resulting clear solution was stirred at ambient temperature for 5 hr and then poured into 2L of water. The resulting solid was collected by filtration and the filter cake was washed with 1.5L of water and dried (air). The solid was recrystallized from chloroform to yield 31.1 g (78%) of a white solid, mp 125°-128° C.

Analysis: Calculated for $C_{15}H_{17}NO_5S$: C, 55.72; H, 5.30; N, 4.33; Found: C, 55.45; H, 5.27; N, 4.35.

EXAMPLE 165

Dimethylsulfamic acid 3-chlorophenyl ester

A solution of 25.7 g (0.2 mole) of 3-chlorophenol and 34.9 g (0.24 mole) of dimethylsulfamoyl chloride (Aldrich) in 150 ml of toluene was stirred and heated at reflux for 16 h, cooled and treated with 300 ml of 15% sodium hydroxide solution. The layers were separated and the organic layer was washed with two 200 ml portions of 15% sodium hydroxide solution, 300 ml of water and dried (magnesium sulfate). The solvent was evaporated under reduced pressure and the brown viscous oil was purified by chromatography (4.5×90 in glass column, 530 g of silica gel, ethyl acetate-hexanes, 1:6). Fractions containing the desired product were combined and the solvents were evaporated under reduced pressure to yield 10.5 g (47%) of the title compound as a light yellow liquid.

Analysis: Calculated for $C_8H_{10}ClNO_3S$: C, 40.77; H, 4.28; N, 5.94; Found: C, 40.01; H, 4.29; N, 5.91.

EXAMPLE 166

Dimethylsulfamic acid 2-methoxyphenyl ester.

A solution of 24.8 g (0.2 mole) of guaiacol (Aldrich) and 34.9 g (0.27 mole) of diisopropylethylamine (Hunig's base, Aldrich) in 200 ml of toluene was added to a solution of 29 ml (0.27 mole) of dimethylsulfamoyl chloride (Aldrich) in 75 ml of toluene and the stirred reaction mixture was heated at reflux for 12 hr. The reaction mixture was successively washed with four 300 ml portions of 6N hydrochloric acid solution, 400 ml of water, three 200 ml portions of 20% sodium hydroxide solution, 400 ml of water and dried (magnesium sulfate). The solvent was evaporated under reduced pressure to give a brown, viscous oil that solidified upon standing. The solid was recrystallized from ethyl ether-petroleum ether and was collected by filtration. The filtrate was evaporated under reduced pressure and the viscous, brown oil was purified by chromatography (4.5×90 cm glass column, 5.30 g of silica gel, ethyl acetate-hexanes, 1:8). Fractions containing the desired compound were combined and the solvents evaporated under reduced pressure to yield 2.5 g (5%) of the title compound as a light yellow liquid.

Analysis: Calculated for $C_9H_{13}NO_4S$: C, 46.74; H, 5.67; N, 6.06; Found: C, 46.76; H, 5.73; N, 6.04.

EXAMPLE 167

Sulfamic acid 2-[3-[2-[(aminosulfonyl)oxy]ethoxy]phenoxy]ethyl ester.

To a suspension of 25.0 g (0.13 mole) of resorcinol-bis($\beta$-hydroxyethyl)ether (Lancaster Synthesis, Windham, N.H. 03087) in 150 ml of acetonitrile was added simultaneously 170 ml (0.53 mole) of sulfamoyl chloride solution (3.14M solution in acetonitrile) and 54.1 g (0.54 mole) of triethylamine (temperature $\leq 15°$ C.) and the reaction mixture was stirred at ambient temperature overnight. The reaction mixture was treated with 200 ml of water and 300 ml of ethyl acetate, the layers were separated, and the organic layer was washed with two 200 ml portions of water. The organic solvents were evaporated under reduced pressure and the solid residue was treated with 500 ml of ethyl acetate and 200 ml of water. The mixture was filtered[1] and the filtrate layers were separated. The organic layer was washed with five 200 ml portions of water (filtrate pH neutral to pH paper) and dried (magnesium sulfate). The solvent was evaporated under reduced pressure and the solid residue was dissolved in 300 ml of ethyl acetate and filtered through celite. The filtrate was evaporated under reduced pressure and the solid residue was recrystallized from ethyl acetate to yield 19.6 g (44%) of an off-white solid, mp 147°-149° C.

Analysis: Calculated for $C_{10}H_{16}N_2O_8S_2$: C, 33.70; H, 4.53; N, 7.86; Found: C, 34.06; H, 4.65; N, 7.83. [1]The filter cake (14.0 g, 31%) was shown by $^1H$ NMR to be mainly the desired product. Total yield 33.6 g (75%).

EXAMPLE 168

Sulfamic acid 2-(4-hydroxyphenoxy)ethyl ester.

To a solution of 25.8 g (0.08 mole) of sulfamic acid 2-[4-(phenylmethoxy)phenoxy]ethyl ester in 150 ml of tetrahydrofuran was added 0.5 teaspoon of 10% palladium on carbon catalyst and the mixture was hydrogenated in a Parr bottle at 40° C. overnight. The catalyst was removed and a fresh 0.5 teaspoon of 10% palladium on carbon catalyst was added and the mixture was hydrogenated at 40° C. for 3 hr whereby hydrogen uptake ceased. The catalyst was removed by filtration through Celite ® and the filtrate was evaporated under reduced pressure to give a viscous oil that solidified upon standing. The solid was recrystallized from ethyl acetate-chloroform to yield 18.0 g (97%) of a shiny, white solid, mp 92°-93° C.

Analysis: Calculated for $C_8H_{11}NO_5S$: C, 41.20; H, 4.75; N, 6.01; Found: C, 41.17; H, 4.81; N, 6.03.

EXAMPLE 169

Sulfamic acid 2-(3-hydroxyphenoxy)ethyl ester.

To a solution of 17.1 g (0.053 mole) of sulfamic acid 2-[3-(phenylmethoxy)phenoxy]ethyl ester in 250 ml of tetrahydrofuran was added 0.5 teaspoon of 5% palladium on carbon catalyst and the mixture was hydrogenated in a Parr bottle at 40° C. for 2 hr. The catalyst was removed and a fresh 0.5 teaspoon of 5% palladium on carbon catalyst was added and the mixture was hydrogenated at 40° C. for 19 hr, whereby hydrogen uptake ceased. The catalyst was removed by filtration through Celite ® and the solvent was evaporated under reduced pressure to yield 12.3 g of a brown, viscous oil that solidified after standing for five weeks at ambient temperature. The solid was triturated with ethyl ether-petroleum ether into a paste. The solvents were decanted and the paste was dried to yield 8.9 g (72%) a white solid, mp 56°-60° C.

Analysis: Calculated for $C_8H_{11}NO_5S$: C, 41.20; H, 4.75; N, 6.01; Found: C, 41.25; H, 4.80; N, 5.92.

PHARMACOLOGY

Chronic Arthritis Test Procedure

The test utilized to evidence antiarthritic properties of the compounds of Formula I is an adjuvant-induced arthritis test model in rats. Adjuvant arthritis was induced in adult, female Lewis rats as described by Walz et al. J. Pharmac. Exp. Ther. 178:223-231 (1971). Briefly, arthritis was induced in the rats by injection of 0.05 ml of a 1.5% suspension of killed *Mycobacterium Butyricum* into the right rear foot pad of each rat. Eighteen days later, those rats having a left hind paw volume (measured by mercury displacement up to a reference tatoo mark placed on the leg on Day 0) of 2.4 ml or greater were randomly assigned to treatment groups. The test, reference and control articles (as solutions or suspensions in 0.5% Tween 80) were given by gavage, beginning on Day 18 after adjuvant administration and for 5 days a week (Monday through Friday) through Day 49. Paw volumes were recorded on days 18, 29 and 50 after adjuvant injection. On Day 50, the rats were killed (carbon dioxide) and the uninjected hind limb was x-rayed and scored for bone damage on an arbitrary 1 (no damage) to 10 (maximum damage) scale.

Data collected for hind paw volumes and bone damage were analyzed by the Dunnett's t-test [Dunnett, C. W., J. Amer. Stat. Assoc., 50:1096-1121 (1955)], comparing a positive control group with several treated groups.

The compound of Example 3, one of the more active compounds of Formula I, showed bone damage scores of 5.4-5.9 over the dosage range of 1 mg/kg to 100 mg/kg compared to the controls which scored 8 to 9. The reduction in bone damage is considered to be significant. Reduction in paw edema in this dosage range was from 0.41 ml to 0.94 ml and was considered to be significant.

OSTEOPOROSIS

In order to determine the effectiveness of Formula I compounds in the treatment and/or prevention of osteoporosis in mammalian species an in vitro experimental procedure was utilized to measure bone resorption. The procedure utilized was as follows.

Bone resorption in vitro was measured essentially as outlined by Hall and Kenny (Pharmacology 30:339-347, 1985), except however, seventeen (17) dayold chick embryo calvaria were utilized instead of mice calvaria. Resorption is defined as the amount of calcium (mg/ml) in the medium of vehicle-treated cultures. The effects of the Formula I test compounds were determined by monitoring the effect on calcium concentrations in presence of drug relative to control calcium concentrations at a particular PTH (parathyroid hormone) concentration. The % inhibition of resorption induced by parathyroid hormone by Formula I compounds was calculated as follows:

$$\% \text{ Inhibition} = \frac{Ca(PTH) - Ca(PTH + \text{Formula I compound})}{Ca(PTH)}$$

where
Ca (PTH)=Ca (PTH)−Ca (Vehicle medium), and
Ca (PTH+Formula I compound)=Ca (PTH+Formula I compound)−Ca (Vehicle medium)
The following results contained in Table II were obtained in the above testing procedure for one of the preferred compounds of the present invention, i.e., Example No. 3, such results being representative of effectiveness in the treatment and/or prevention of osteoporosis.

| PTH [M] | % Inhibition of Resorption Induced by PTH by the compound of Example 3 | | | |
|---|---|---|---|---|
| | $10^{-4}$ M | $10^{-5}$ M | $10^{-6}$ M | $10^{-7}$ M |
| $10^{-7}$ | 10 | 21 | 21 | — |
| $10^{-8}$ | 40.5 | 37 | 29 | 23 |
| $10^{-9}$ | 66.5 | 86 | 100 | — |
| $10^{-10}$ | 100 | 100 | 100 | — |

Pharmaceutical Compositions

The invention further provides pharmaceutical compositions for administration to a living animal body comprising, as active ingredients, at least one of the compounds according to the invention in association with a pharmaceutical carrier or excipient. The compounds are thus presented in a therapeutic composition suitable for oral, rectal or parenteral administration. Thus, for example, compositions for oral administration are preferably solids and can take the form of capsules, tablets or coated tablets containing carriers conveniently used in the pharmaceutical art. Suitable tableting carriers or excipients include lactose, potato and maize starches, talc, gelatin and stearic and silicic acids, magnesium stearate and polyvinyl pyrrolidone.

For parenteral administration, the carrier or excipient can be a sterile, parenterally acceptable liquid, e.g., water, or a parenterally acceptable oil; e.g., arachis oil, contained in ampoules.

In compositions for rectal administration the carrier can comprise a suppository base, e.g., cocoa butter, or a glyceride.

Advantageously, the compositions are formulated as dosage units, each unit being adapted to supply a fixed dose of active ingredients. Tablets, coated tablets, capsules, ampoules and suppositories are examples of preferred dosage forms according to the invention. It is only necessary that the active ingredient constitute an effective amount; i.e., such that a suitable effective dosage will be obtained consistent with the dosage form employed. The exact individual dosages, as well as daily dosages, will, of course, be determined according to standard medical principles under the direction of a physician or veterinarian. Generally the oral effective dose to either prevent or treat chronic arthritic conditions, would consist of unit dosages containing an amount of compound equivalent to about 1 to about 20 mg/kg of body weight and thus are contemplated. Based on all of the above considerations, a choice in a range of unit oral dosages for humans of about 10 to about 1000 mg is contemplated, preferably about 10 to 600 mg. Daily dosages of about 30 to 2400 mg are contemplated for humans and obviously several unit dosage forms may be administered at about the same time. However, the scope of the invention is not to be limited by these contemplations due to the uncertainty in transpositions discussed above.

Examples of unit dosage compositions are as follows:

| Capsules | |
|---|---|
| Ingredients | Per Cap. |
| 1. Active ingredient | 10.0 mg |
| 2. Lactose | 146.0 mg |
| 3. Magnesium Stearate | 4.0 mg |
| | 160.0 mg |

Procedure
Step 1. Blend ingredients 1, 2 and 3.
Step 2. Pass blend from Step 1 through a No. 30 mesh screen (0.59 mm) and blend again.
Step 3. Fill powder blend from Step 2 into No. 1 hard gelatin capsules.

| Ingredients | Mg./Tab. |
|---|---|
| Tablets (10 mg) | |
| 1. Active Ingredient | 10.0 mg |
| 2. Corn starch | 20.0 mg |
| 3. Alginic acid | 20.0 mg |
| 4. Sodium alginate | 20.0 mg |
| 5. Magnesium stearate | 1.3 mg |
| | 71.3 mg |
| Tablets (50 mg) | |
| 1. Active Ingredient | 50.0 mg |
| 2. Milo starch | 20.0 mg |
| 3. Corn starch | 38.0 mg |
| 4. Lactose | 90.0 mg |
| 5. Magnesium stearate | 2.0 mg |
| | 200.0 mg |

Procedure
Step 1. Blend ingredients 1, 2 and 3 and 4.
Step 2. Add sufficient water portion wise to the blend from Step 1 with careful stirring after each addition. Such additions of water and stirring continue until the mass is of a consistency to permit its conversion to wet granules.

Step 3. The wet mass prepared in Step 2 is converted to granules by passing it through an oscillating granulator, using a #8-mesh (2.36 mm) screen.

Step 4. The wet granules prepared in Step 3 are dried in an oven at 140° F.

Step 5. Dried granules from Step 4 are passed through an oscillating granulator, using a No. 10-mesh (2.00 mm) screen.

Step 6. Lubricate the dry granules from Step 5 by blending with ingredient No. 5.

Step 7. The lubricated granules from Step 6 are compressed on a suitable tablet press.

| Intravenous Injection | |
|---|---|
| Ingredients | Per ml. |
| 1. Active Ingredient | 10.0 mg |
| 2. Isotonic pH 4.0 buffer solution q.s. to | 1.0 ml |

Procedure

Step 1. Dissolve the active ingredient in the buffer solution.

Step 2. Aseptically filter the solution from Step 1.

Step 3. The sterile solution is now aseptically filled into sterile ampuls.

Step 4. The ampuls are sealed under aseptic conditions.

| Intramuscular Injection | |
|---|---|
| Ingredients | Per ml. |
| 1. Active ingredients | 50.0 mg |
| 2. Isotonic pH 4.0 buffer solution q.s. to | 5.0 ml |

Procedure

Step 1. Dissolve the active ingredient in the buffer solution.

Step 2. Aseptically filter the solution from Step 1.

Step 3. The sterile solution is now aseptically filled into sterile ampuls.

Step 4. The ampuls are sealed under aseptic conditions.

| Suppositories | |
|---|---|
| Ingredients | Per Supp. |
| 1. Active ingredient | 500.0 mg |
| 2. Polyethylene Glycol 1000 | 1350.0 mg |
| 3. Polyethylene Glycol 4000 | 450.0 mg |
| | 2300.0 mg |

Procedure

Step 1. Melt ingredients 2 and 3 together and stir until uniform.

Step 2. Dissolve 1 in the molten mass from Step 1 and stir until uniform.

Step 3. Pour the molten mass from Step 2 into suppository molds and allow to cool.

Step 4. Remove the suppositories from molds and wrap.

Various modifications and equivalents will be apparent to one skilled in the art and may be made in the compounds, method, and compositions of the present invention without departing from the spirit or scope thereof, and it is therefore to be understood that the invention is to be limited only the scope of the appended claims.

What is claimed is:

1. A compound selected from the group having the formula:

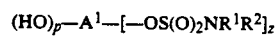

wherein $A^1$ is substituted on one or more carbon atoms by an aminosulfonyloxy radical, said $A^1$ being selected from the group consisting of:
  aryloxyalkyl,
  arylalkyl, with a proviso that the alkyl moiety is substituted by more than one aminosulfonyloxy radical;
  aryloxycarbonylalkyl,
  arylcarbonylalkyl,
  and arylalkanoic acid;
where in the above groups under the definition of $A^1$ an alkyl moiety is present, said alkyl moiety must be substituted by at least one aminosulfonyloxy group and as further defined above; and where the aryl moiety is:

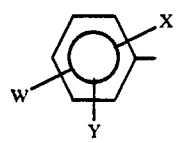

where X is selected from 1H-imidazol-1-yl, 2-(or 4-)loweralkyl-1H-imidazol-1-yl, and 4-phenyl-1H-imidazol-1-yl;
Y is selected from hydrogen, halogen, loweralkoxy, hydroxy or loweralkyl;
W is selected from hydrogen, loweralkoxy or loweralkyl;
p is the number of unreacted hydroxyl groups, including zero;
z is the number of $-OSO_2NR^1R^2$ groups and is always at least one;
$R^1$ = hydrogen or loweralkyl;
$R^2$ = hydrogen, loweralkyl, $-CO_2R^1$, or $-CO_2-M^+$ wherein M is a pharmaceutically acceptable metal cation;
an optical isomer, or a pharmaceutically acceptable salt thereof when one can be formed.

2. A compound according to claim 1 wherein $A^1$ is aryloxyalkyl.

3. A compound according to claim 2 which is 2-[4-(1H-imidazol-1-yl)phenoxy]ethanol sulfamic acid ester or a pharmaceutically acceptable salt thereof.

4. A compound according to claim 2 which is methylsulfamic acid 2-[4-(1H-imidazol-1-yl)phenoxy]ethyl ester or a pharmaceutically acceptable salt thereof.

5. A compound according to claim 2 which is 2-[4-(1H-imidazol-1-yl)phenoxy]ethanol dimethylsulfamic acid or a pharmaceutically acceptable salt thereof.

6. A compound according to claim 2 which is 2-[4-(2-methyl-1H-imidazol-1-yl)phenoxy]ethyl sulfamate ester.

7. A pharmaceutical composition for treatment of chronic arthritis or osteoporosis in a mammal comprised of a pharmaceutical carrier and a therapeutically effective amount of a compound according to the formula:

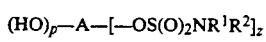

wherein A is substituted on one or more carbon atoms by an aminosulfonyloxy radical, said A being selected from the group consisting of:
aryl,
aryl-alkyl,
arylalkanoic acid,
aryloxy-alkyl,
(aryl)(loweralkyl)aminoalkyl,
aryl-thio alkyl,
aryl-sulfinyl-alkyl,
aryl-sulfonyl-alkyl,
arylaminocarbonylalkyl,
aryloxycarbonylalkyl,
2-pyrrolidinone-1-alkyl,
arylcarbonylalkyl,
arylalkanoic acid,
arylcarboxyalkyl,
arylhalogen substituted alkyl, and
arylalkyloxyalkyl;
where aryl is:

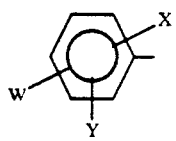

and X is selected from 1H-imidazol-1-yl, 2-(or 4-)loweralkyl-1H-imidazol-1-yl, and 4-phenyl-1H-imidazol-1-yl;
Y is selected from hydrogen, halo, loweralkoxy, hydroxy or loweralkyl;
W is selected from hydrogen, loweralkoxy or loweralkyl;
p=number of unreacted hydroxyl groups, including zero;
z=number of —OS(O)$_2$NR$^1$R$^2$ groups and is always at least one;
n=p+z=1-8;
R$^1$=H or loweralkyl;
R$^2$=H, loweralkyl, —CO$_2$R$^1$, or —CO$_2$—M$^+$ wherein M is a pharmaceutically acceptable metal cation;
an optical isomer, or a pharmaceutically acceptable salt thereof when one can be formed.

8. A method for treating chronic arthritis in a mammal, comprising administering to said mammal an effective antiarthritic amount of a compound having the formula:

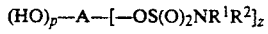
(HO)$_p$—A—[—OS(O)$_2$NR$^1$R$^2$]$_z$ wherein A is substituted on one or more carbon atoms by an aminosulfonyloxy radical, said A being selected from the group consisting of:
aryl,
aryl-alkyl,
arylalkanoic acid,
aryloxy-alkyl,
(aryl)(loweralkyl)aminoalkyl,
aryl-thio alkyl,
aryl-sulfinyl-alkyl,
aryl-sulfonyl-alkyl,
arylaminocarbonylalkyl,
aryloxycarbonylalkyl,
2-pyrrolidinone-1-alkyl,
arylcarbonylalkyl,
arylalkanoic acid,
arylcarboxyalkyl,
arylhalogen substituted alkyl, and
arylalkyloxyalkyl;
where aryl is:

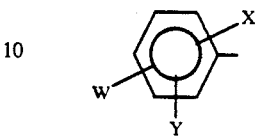

and X is selected from 1H-imidazol-1-yl, 2-(or 4-)loweralkyl-1H-imidazol-1-yl, and 4-phenyl-1H-imidazol-1-yl;
Y is selected from hydrogen, halo, loweralkoxy, hydroxy or loweralkyl; W is selected from hydrogen, loweralkoxy or loweralkyl;
p=number of unreacted hydroxyl groups, including zero;
z=number of —OS(O)$_2$NR$^1$R$^2$ groups and is always at least one;
n=p+z=1-8;
R$^1$=H or loweralkyl;
R$^2$=H, loweralkyl, —CO$_2$R$^1$, or —CO$_2$—M$^+$ wherein M is a pharmaceutically acceptable metal cation;
an optical isomer, or a pharmaceutically acceptable salt thereof when one can be formed.

9. A method for treating osteoporosis in a mammal, comprising administering to said mammal an effective antiarthritic amount of a compound having the formula:

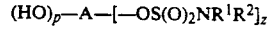
(HO)$_p$—A—[—OS(O)$_2$NR$^1$R$^2$]$_z$ wherein A is substituted on one or more carbon atoms by an aminosulfonyloxy radical, said A being selected from the group consisting of:
aryl,
aryl-alkyl,
arylalkanoic acid,
aryloxy-alkyl,
(aryl)(loweralkyl)aminoalkyl,
aryl-thio alkyl,
aryl-sulfinyl-alkyl,
aryl-sulfonyl-alkyl,
arylaminocarbonylalkyl,
aryloxycarbonylalkyl,
2-pyrrolidinone-1-alkyl,
arylcarbonylalkyl,
arylalkanoic acid,
arylcarboxyalkyl,
arylhalogen substituted alkyl, and
arylalkyloxyalkyl;
where aryl is:

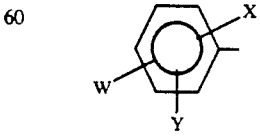

and X is selected from 1H-imidazol-1-yl, 2-(or 4-)loweralkyl-1H-imidazol-1-yl, and 4-phenyl-1H-imidazol-1-yl;

Y is selected from hydrogen, halo, loweralkoxy, hydroxy or loweralkyl;

W is selected from hydrogen, loweralkoxy or loweralkyl;

p = number of unreacted hydroxyl groups, including zero;

z = number of $-OS(O)_2NR^1R^2$ groups and is always at least one;

n = p + z = 1-8;

$R^1$ = H or loweralkyl;

$R^2$ = H, loweralkyl, $-CO_2R^1$, or $-CO_2-M^+$ wherein M is a pharmaceutically acceptable metal cation;

an optical isomer, or a pharmaceutically acceptable salt thereof when one can be formed.

* * * * *